(12) United States Patent
Barrow et al.

(10) Patent No.: US 7,875,636 B2
(45) Date of Patent: Jan. 25, 2011

(54) PYRIDYL AMIDE T-TYPE CALCIUM CHANNEL ANTAGONISTS

(75) Inventors: James C. Barrow, Arnold, MD (US); Thomas S. Reger, Lansdale, PA (US); Zhi-Qiang Yang, Schwenksville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 124 days.

(21) Appl. No.: 12/226,117

(22) PCT Filed: Apr. 11, 2007

(86) PCT No.: PCT/US2007/008977
§ 371 (c)(1),
(2), (4) Date: Oct. 8, 2008

(87) PCT Pub. No.: WO2007/120729
PCT Pub. Date: Oct. 25, 2007

(65) Prior Publication Data
US 2009/0275550 A1  Nov. 5, 2009

Related U.S. Application Data

(60) Provisional application No. 60/791,372, filed on Apr. 12, 2006.

(51) Int. Cl.
- A61K 31/445 (2006.01)
- A61K 31/415 (2006.01)
- C07D 213/72 (2006.01)
- C07D 213/00 (2006.01)

(52) U.S. Cl. .................. 514/351; 514/357; 546/300; 546/337

(58) Field of Classification Search ............... 546/337, 546/300, 329; 514/357, 351
See application file for complete search history.

(56) References Cited

U.S. PATENT DOCUMENTS

| | | | |
|---|---|---|---|
| 2,798,075 A | 7/1957 | Rey-Bellet et al. | |
| 3,594,382 A | 7/1971 | Florin et al. | |
| 3,679,698 A | 7/1972 | Beaman et al. | |
| 5,607,976 A | 3/1997 | Englert et al. | |
| 5,693,650 A | 12/1997 | Muller et al. | |
| 5,747,505 A | 5/1998 | Connell et al. | |
| 5,925,646 A | 7/1999 | Connell et al. | |
| 6,521,663 B2 | 2/2003 | Pan et al. | |
| 6,610,701 B2 * | 8/2003 | Barrow et al. | 514/300 |
| 6,703,392 B2 | 3/2004 | Aissaoui et al. | |
| 6,897,207 B2 | 5/2005 | Cox et al. | |
| 6,900,231 B2 | 5/2005 | Pan et al. | |
| 6,989,402 B1 | 1/2006 | Hangeland et al. | |
| 7,192,950 B2 | 3/2007 | Aissaoui et al. | |
| 7,288,571 B2 | 10/2007 | Hangeland et al. | |
| 2002/0183519 A1 | 12/2002 | Nar et al. | |
| 2002/0193398 A1 | 12/2002 | Barrow et al. | |
| 2003/0100554 A1 | 5/2003 | Jones et al. | |
| 2003/0199523 A1 | 10/2003 | Snutch | |
| 2006/0074076 A1 | 4/2006 | Termin et al. | |
| 2007/0043038 A1 | 2/2007 | Starck et al. | |
| 2007/0173504 A1 | 7/2007 | Pacofsky et al. | |
| 2008/0039472 A1 | 2/2008 | Lacrampe et al. | |
| 2008/0167287 A1 | 7/2008 | Zhuo et al. | |
| 2008/0318976 A1 | 12/2008 | Wood et al. | |

FOREIGN PATENT DOCUMENTS

| | | |
|---|---|---|
| EP | 1 760 072 | 3/2007 |
| EP | 1 762 218 | 3/2007 |
| GB | 782 067 | 8/1957 |
| GB | 1 403 264 | 8/1975 |
| WO | WO0039077 | 7/2000 |
| WO | WO0111966 | 2/2001 |
| WO | WO0168609 | 9/2001 |
| WO | WO02051838 | 7/2002 |
| WO | WO03000688 | 1/2003 |
| WO | WO2006032631 | 3/2006 |
| WO | WO2006115652 | 11/2006 |
| WO | WO2007073505 | 6/2007 |
| WO | WO2008064157 | 5/2008 |
| WO | WO2009054982 | 4/2009 |
| WO | WO2009054983 | 4/2009 |
| WO | WO2009054984 | 4/2009 |

OTHER PUBLICATIONS

G. Primofiore et al., "Refinement of the Benzodiazepine Receptor Site Topology by Structure-Activity Relationships of New N-(Heteroarylmethyl) Indol-3-Y lglyoxylamides", J. of Medicinal Chemistry, vol. 49, No. 8, pp. 2489-2495, XP002457568, 2006.

(Continued)

Primary Examiner—Janet L Andres
Assistant Examiner—Binta M Robinson
(74) Attorney, Agent, or Firm—J. Eric Thies; Gerard M. Devlin

(57) ABSTRACT

The present invention is directed to pyridyl amide compounds which are antagonists of T-type calcium channels, and which are useful in the treatment or prevention of disorders and diseases in which T-type calcium channels are involved. The invention is also directed to pharmaceutical compositions comprising these compounds and the use of these compounds and compositions in the prevention or treatment of such diseases in which T-type calcium channels are involved.

15 Claims, No Drawings

OTHER PUBLICATIONS

P. G. Nantermet et al., "P2 Pyridine N-Oxide Thrombin Inhibitors: A Novle Peptidomimetic Scaffold", Biorganic & Medicinal Chemistry Letters, vol. 15, No. 11, pp. 2771-2775, XP004906893, 2005.

Hanessian et al., "Phenolic P2/P3 Core Motif as Thrombin Inhibitors-Desing, Synthesis, and X-Ray Co-Crystal Structure", Biorganic & Medicinal Chemistry Letters, vol. 16, No. 4, pp. 1032-1036, XP005237642, 2006.

Data Beilstein, Beilstein Institute for Organic Chemistry, Frankfurt -Main, DE: BRN 6741916, XP002457570, 1983.

Y. Katsura et al., "Thiazoline or Thiazine Derivatives as Nitric Oxide Formation Inhibitors", Database Accession No. 1998:239552, XP002457571, 1998.

Howell et al., "Synthesis and Characterization of 3-Thiophene Carboxamides Containing a Pyridine Ring: Structure, Electrochemistry, and Complexation", vol. 358, No. 13, pp. 3711-3723, XP005065590, 2005.

G. Blay et al., "Catalytic Asymmetric Addition of Dimethyizinc to Alpha-Ketoesters, Using Mandelamides as Ligands", Database Accession No. 2006:207062, XP002457572, 2006.

G. Blay et al., "Enantioselective Additon of Dimethylzinc to Aldehydes Catalyzed by N-Substituted Mandelamide -Ti (IV) Complexes", vol. 16, No. 11, pp. 1953-1958, XP00492366, 2005.

W. L. Albrecht et al., "3-Substituted Imidazoa1, 5-Alphaupyridines" J. of Heterocyclic Chemistry, vol. 16, No. 7. pp. 1349-1351, XP001106066, 1979.

K. Winterfield et al., "Synthesis of 3-Substittued 2-Azainolizines", vol. 75, No. 22, pp. 1101-1102, XP002457569, 1963.

B. Lee et al., "Copper (II) Complexes with Novel Chiral Amidate Ligands", Database Accession No. 2002:100958, 2002.

E. Widy-Tyszkiewicz et al., "Pharmacological Studies on 2-and 4-Pyridylmethylamides of Acetyltropic Acid (PAT-2 and PAT-4)", Database Accession No. 1975:601828, 1975.

N. Nonoyama et al., "Cobalt (II), Nickel (II), and Copper (II) Complexes of Potentially Terdentate N-(2'-Picolyl)-2-PYridylacetamide", Database Accession No. 1975:557164, 1975.

V. Uebele et al., "Positive Allosteric Interaction of Structurally Diverse T-Type Calcium Channel Antagonists", Cell Biochem Biophys, pp. vol. 55, pp. 81-93, 2009.

V. Uebele et al., "T-Type Calcium Channels Regulate Cortical Plasticity In-Vivo NR-D-08-7049", Neurophysiology, vol. 20, pp. 257-262, 2009.

International Search Report, PCT/US2007/008977,Nov. 15, 2007.

International Preliminary Report on Patentability, PCT/US2007/008977, Oct. 23, 2008.

Database Registry, "Benzeneacetamide, 4-[[3-[(4-fluorophenyl)methly]-1,2,4-thiadiazol-5-y]oxy]-N-(2-pyridinylmethyl)", Registry No. 855509-20-5:, XP002513628, Jul. 15, 2005.

Database Registry, "4-[[3-[[(3-methoxyphenyl)methyl]-1,2,4-thiadiazol-5-yl]oxy]-N-(2-pyridinylmethyl)-"Registry No. 854170-18-6:, XP002513629, Jul. 8, 2005.

Database Registry, "4-(1,4-dihydro-4-oxo-2-thioxo-3(2H)-quinazolinyl)-N-(2-pyridinylmethyl)", Registry No. 689763-76-6, XP002513630, Jun. 6, 2004.

Database Registry, "4-(2-methyl-3H-Imidazo(4,5-b)pyridin-3-yl)-N-(2-pyridinylmethyl)", Registry No. 931970-35-3, XP002513623, Apr. 23, 2007.

Database Registry, "4-(1,4-Dihydro-2,4-Dioxo-3(2H)-quinazoliny1)-N-(2-pyridinylmethyl", Registry No. 896376-19-5, XP00251624, Jul. 27, 2006.

Database Registry, "Benzeneacetamide, 4-[(2-ethyl-3H-imidazo[4,5-b]pyridin-3-yl)-N-(2-pyridinylmethyl)", Registry No. 894181-12-5, XP002513625, Jul. 18, 2006.

Database Registry, "Benzeneacetamide, 4-(2-oxo-1-pyrrolidinyl)-N-(2-pyridinylmethyl)", Registry No. 931630-57-8, XP002513626, Apr. 22, 2007.

* cited by examiner

PYRIDYL AMIDE T-TYPE CALCIUM CHANNEL ANTAGONISTS

CROSS REFERENCE TO RELATED APPLICATIONS

This application is a U.S. National Phase application under 35 U.S.C. §371 of PCT Application No. PCT/US2007/008977 filed Apr. 11, 2007, which claims priority under 35 U.S.C. §119 from U.S. Application No. 60/791,372, filed Apr. 12, 2006.

BACKGROUND OF THE INVENTION

Plasma membrane calcium channels are members of a diverse superfamily of voltage gated channel proteins. Calcium channels are membrane-spanning, multi-subunit proteins that allow controlled entry of Ca2+ ions into cells from the extracellular fluid. Excitable cells throughout the animal kingdom, and at least some bacterial, fungal and plant cells, possess one or more types of calcium channel. Nearly all "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels.

Multiple types of calcium channels have been identified in mammalian cells from various tissues, including skeletal muscle, cardiac muscle, lung, smooth muscle and brain. A major type of this family are the L-type calcium channels, whose function is inhibited by the familiar classes of calcium channel blockers (dihydropyridines such as nifedipine, phenylalkylamines such as verapamil, and benzothiazepines such as diltiazem). Additional classes of plasma membrane calcium channels are referred to as T, N, P, Q and R.

The "T-type" (or "low voltage-activated") calcium channels are so named because their openings are of briefer duration (T=transient) than the longer (L=long-lasting) openings of the L-type calcium channels. The L, N, P and Q-type channels activate at more positive potentials (high voltage activated) and display diverse kinetics and voltage-dependent properties. There are three subtypes of T-type calcium channels that have been molecularly, pharmacologically, and electrophysiologically identified from various warm blooded animals including rat [J Biol. Chem. 276(6) 3999-4011 (2001); Eur J Neurosci 11(12):4171-8 (1999); reviewed in Cell Mol Life Sci 56(7-8):660-9 (1999)]. These subtypes have been termed α1G, α1H, and α1I. The molecular properties of these channels demonstrate that the amino acid sequences are between 60-70% identical. The electrophysiological characterization of these individual subtypes has revealed differences in their voltage-dependent activation, inactivation, deactivation and steady-state inactivation levels and their selectivities to various ions such as barium (J Biol. Chem. 276(6) 3999-4011 (2001)). Pharmacologically, these subtypes also have differing sensitivities to blockade by ionic nickel. These channel subtypes are also expressed in various forms due to their ability to undergo various splicing events during their assembly (J Biol. Chem. 276(6) 3999-4011 (2001)).

T-type calcium channels have been implicated in pathologies related to various diseases and disorders, including epilepsy, essential tremor, pain, neuropathic pain, schizophrenia, Parkinson's disease, depression, anxiety, sleep disorders, sleep disturbances, psychosis, schizophrenia, cardiac arrhythmia, hypertension, pain, cancer, diabetes, infertility and sexual dysfunction (J Neuroscience, 14, 5485 (1994); Drugs Future 30(6), 573-580 (2005); EMBO J, 24, 315-324 (2005); Drug Discovery Today, 11, 5/6, 245-253 (2006)). The known therapeutic regimens for such treating such diseases and disorders suffer from numerous problems. Accordingly, a more physiological way to treat these diseases and disorders would be highly desirable.

SUMMARY OF THE INVENTION

The present invention is directed to pyridyl amide compounds which are antagonists of T-type calcium channels, and which are useful in the treatment or prevention of neurological and psychiatric disorders and diseases in which T-type calcium channels are involved. The invention is also directed to pharmaceutical compositions comprising these compounds and the use of these compounds and compositions in the prevention or treatment of such diseases in which T-type calcium channels are involved.

DETAILED DESCRIPTION OF THE INVENTION

The present invention is directed to compounds of the formula I:

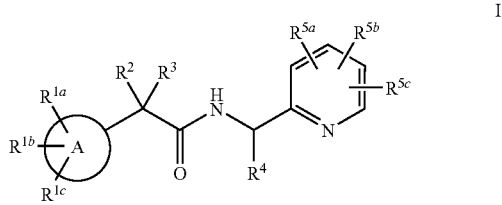

wherein:
A is selected from the group consisting of phenyl, napthyl and heteroaryl;
$R^{1a}$, $R^{1b}$ and $R^{1c}$ may be absent if the valency of A does not permit such substitution and are independently selected from the group consisting of:
(1) hydrogen,
(2) halogen,
(3) hydroxyl,
(4) —$O_n$-phenyl or —$O_n$-napthyl, where n is 0 or 1 (wherein if n is 0, a bond is present) and where the phenyl or napthyl is unsubstituted or substituted with one or more substituents selected from $R^{13}$,
(5) —$O_n$-heterocycle, where n is 0 or 1 (wherein if n is 0, a bond is present) and where the heterocycle is unsubstituted or substituted with one or more substituents selected from $R^{13}$,
(6) —$O_n$—$C_{1-6}$alkyl, where n is 0 or 1 (wherein if n is 0, a bond is present) and where the alkyl is unsubstituted or substituted with one or more substituents selected from $R^{13}$,
(7) —$O_n$—$C_{3-6}$cycloalkyl, where n is 0 or 1 (wherein if n is 0, a bond is present) and where the cycloalkyl is unsubstituted or substituted with one or more substituents selected from $R^{13}$,
(8) —$C_{2-4}$alkenyl, where the alkenyl is unsubstituted or substituted with one or more substituents selected from $R^{13}$,
(9) —$NR^{10}R^{11}$, wherein $R^{10}$ and $R^{11}$ are independently selected from the group consisting of:
  (a) hydrogen,
  (b) $C_{1-6}$alkyl, which is unsubstituted or substituted with $R^{13}$, (c) $C_{3-6}$alkenyl, which is unsubstituted or substituted with $R^{13}$,
(d) cycloalkyl which is unsubstituted or substituted with $R^{13}$,
(e) phenyl, which is unsubstituted or substituted with $R^{13}$, and
(f) heterocycle, which is unsubstituted or substituted with $R^{13}$,
or $R^{10}$ and $R^{11}$ taken together with the nitrogen atom to which they are attached form a pyrrolidine, piperidine, azetidine or morpholine ring, which is unsubstituted or substituted with $R^{13}$,
(10) —S(O)$_2$—NR$^{10}$R$^{11}$,
(11) —S(O)$_q$—R$^{12}$, where q is 0, 1 or 2 and where $R^{12}$ is selected from the definitions of $R^{10}$ and $R^{11}$,
(12) —CO$_2$H,
(13) —CO$_2$—R$^{12}$,
(14) —CN, and
(15) —NO$_2$;
or $R^{1a}$ and $R^{1b}$ taken together form a cyclopentyl, cyclohexyl, dihydrofuranyl or dihydropyranyl ring, which is unsubstituted or substituted with one or more substituents selected from —CH$_3$, (=CH$_2$), keto, and hydroxyl;
$R^2$ and $R^3$ are independently selected from the group consisting of:
(1) hydrogen,
(2) hydroxyl,
(3) halogen
(4) $C_{1-6}$alkyl, which is unsubstituted or substituted with one or more substituents selected from $R^{13}$,
(5) $C_{3-6}$cycloalkyl, which is unsubstituted or substituted with one or more substituents selected from $R^{13}$,
(6) —O—$C_{1-6}$alkyl, which is unsubstituted or substituted with one or more substituents selected from $R^{13}$,
(7) —O—$C_{3-6}$cycloalkyl, which is unsubstituted or substituted with one or more substituents selected from $R^{13}$,
or $R^2$ and $R^3$ and the carbon atom to which they are attached form a keto group,
or $R^2$ and $R^3$ and the carbon atom to which they are attached form a $C_{3-6}$cycloalkyl ring, which is unsubstituted or substituted with $R^{13}$;
$R^4$ is selected from the group consisting of:
(1) hydrogen,
(2) $C_{1-6}$alkyl, which is unsubstituted or substituted with one or more substituents selected from $R^{13}$,
(3) $C_{3-6}$cycloalkyl, which is unsubstituted or substituted with one or more substituents selected from $R^{13}$,
(4) $C_{2-6}$alkenyl, which is unsubstituted or substituted with one or more substituents selected from $R^{13}$,
(5) $C_{2-6}$alkynyl, which is unsubstituted or substituted with one or more substituents selected from $R^{13}$,
(6) phenyl, which is unsubstituted or substituted with one or more substituents selected from $R^{13}$,
(7) —(C=O)—NR$^{10}$R$^{11}$, and
(8) —(C=O)—O—$C_{1-6}$alkyl, which is unsubstituted or substituted with one or more substituents selected from $R^{13}$,
$R^{5a}$, $R^{5b}$ and $R^{5c}$ are independently selected from the group consisting of:
(1) hydrogen,
(2) halogen,
(3) hydroxyl,
(4) —O$_n$—$C_{1-6}$alkyl, where n is 0 or 1 (wherein if n is 0, a bond is present) and where the alkyl is unsubstituted or substituted with one or more substituents selected from $R^{13}$,
(5) —O$_n$—$C_{3-6}$cycloalkyl, where n is 0 or 1 (wherein if n is 0, a bond is present) and where the cycloalkyl is unsubstituted or substituted with one or more substituents selected from $R^{13}$,
(6) —$C_{2-4}$alkenyl, where the alkenyl is unsubstituted or substituted with one or more substituents selected from $R^{13}$,
(7) —O$_n$-phenyl or —O$_n$-napthyl, where n is 0 or 1 (wherein if n is 0, a bond is present) and where the phenyl or napthyl is unsubstituted or substituted with one or more substituents selected from $R^{13}$,
(8) —O$_n$-heterocycle, where n is 0 or 1 (wherein if n is 0, a bond is present) and where the heterocycle is unsubstituted or substituted with one or more substituents selected from $R^{13}$,
(9) —(C=O)—NR$^{10}$R$^{11}$,
(10) —NR$^{10}$R$^{11}$,
(11) —S(O)$_2$—NR$^{10}$R$^{11}$,
(12) —NR$^{10}$—S(O)$_2$R$^{11}$,
(13) —S(O)$_q$—R$^{12}$, where q is 0, 1 or 2 and where $R^{12}$ is selected from the definitions of $R^{10}$ and $R^{11}$,
(14) —CO$_2$H,
(15) —CN,
(16) —NO$_2$;
(17) or $R^{5a}$ and $R^{5b}$ taken together form a pyrrolyl or imidazolyl ring, which is unsubstituted or substituted with —CH$_3$, (=CH$_2$), keto, or hydroxyl;
$R^{13}$ is selected from the group consisting of:
(1) halogen,
(2) hydroxyl,
(3) —(C=O)$_m$—O$_n$—$C_{1-6}$alkyl, where m is 0 or 1 and n is 0 or 1 (wherein if m is 0 or n is 0, a bond is present, and wherein if m is 0 and n is 0, a single bond is present) where the alkyl is unsubstituted or substituted with one or more substituents selected from $R^{14}$,
(4) —O$_n$—($C_{1-3}$)perfluoroalkyl,
(5) —(C=O)$_m$—O$_n$—$C_{3-6}$cycloalkyl, where the cycloalkyl is unsubstituted or substituted with one or more substituents selected from $R^{14}$,
(6) —(C=O)$_m$—$C_{2-4}$alkenyl, where the alkenyl is unsubstituted or substituted with one or more substituents selected from $R^{14}$,
(7) —(C=O)$_m$—O$_n$-phenyl or —(C=O)$_m$—O$_n$-napthyl, where the phenyl or napthyl is unsubstituted or substituted with one or more substituents selected from $R^{14}$,
(8) —(C=O)$_m$—O$_n$-heterocycle, where the heterocycle is unsubstituted or substituted with one or more substituents selected from $R^{14}$,
(9) —(C=O)—NR$^{10}$R$^{11}$,
(10) —NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;
$R^{14}$ is selected from the group consisting of:
(1) hydroxyl,
(2) halogen,
(3) $C_{1-6}$alkyl,
(4) —$C_{3-6}$cycloalkyl,
(5) —O—$C_{1-6}$alkyl,
(6) —O(C=O)—$C_{1-6}$alkyl,
(7) —NH—$C_{1-6}$alkyl,
(8) phenyl,
(9) heterocycle,
(10) —CO$_2$H, and
(11) —CN;
or a pharmaceutically acceptable salt thereof.

An embodiment of the present invention includes compounds of the formula Ib:

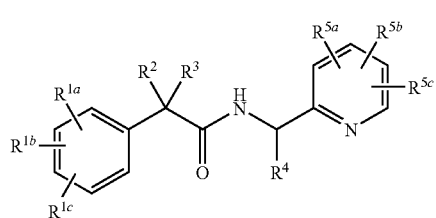

wherein $R^{1a}$, $R^{1b}$, $R^{1c}$, $R^2$, $R^3$, $R^4$, $R^{5a}$, $R^{5b}$ and $R^{5c}$ are defined herein; or a pharmaceutically acceptable salt thereof.

An embodiment of the present invention includes compounds of the formula Ic:

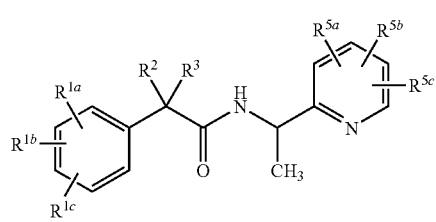

wherein $R^{1a}$, $R^{1b}$, $R^{1c}$, $R^2$, $R^3$, $R^{5a}$, $R^{5b}$ and $R^{5c}$ are defined herein; or a pharmaceutically acceptable salt thereof.

An embodiment of the present invention includes compounds of the formula Ic':

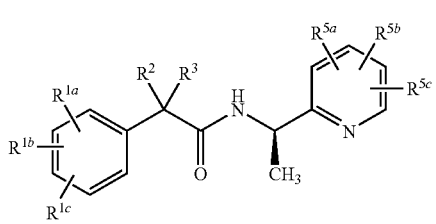

wherein $R^{1a}$, $R^{1b}$, $R^{1c}$, $R^2$, $R^3$, $R^{5a}$, $R^{5b}$ and $R^{5c}$ are defined herein; or a pharmaceutically acceptable salt thereof.

An embodiment of the present invention includes compounds of the formula Id:

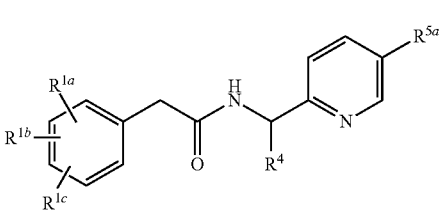

wherein $R^{1a}$, $R^{1b}$, $R^{1c}$, $R^4$ and $R^{5a}$ are defined herein; or a pharmaceutically acceptable salt thereof.

An embodiment of the present invention includes compounds of the formula Ie:

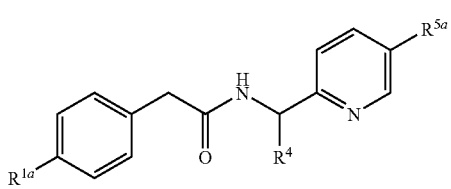

wherein $R^{1a}$, $R^4$ and $R^{5a}$ are defined herein; or a pharmaceutically acceptable salt thereof.

An embodiment of the present invention includes compounds of the formula Ie':

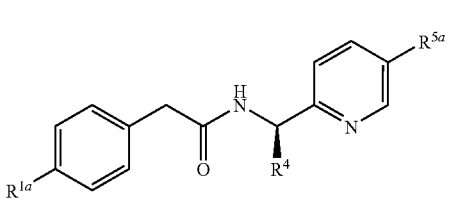

wherein $R^{1a}$, $R^4$ and $R^{5a}$ are defined herein; or a pharmaceutically acceptable salt thereof.

An embodiment of the present invention includes compounds of the formula Ie":

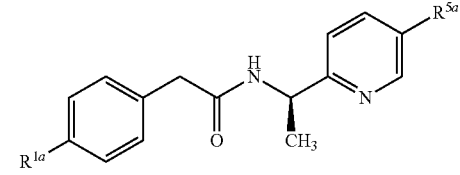

wherein $R^{1a}$ and $R^{5a}$ are defined herein; or a pharmaceutically acceptable salt thereof.

An embodiment of the present invention includes compounds wherein:
A is selected from the group consisting of phenyl and heteroaryl.

An embodiment of the present invention includes compounds wherein A is selected from the group consisting of:
(1) phenyl,
(2) oxazolyl,
(3) isoxazolyl,
(4) thiazolyl,
(5) thiadiazolyl,
(6) triazolyl,
(7) pyrazolyl,
(8) pyridyl, and
(9) pyrimidinyl.

Within this embodiment, the present invention includes compounds wherein A is phenyl. Also within this embodiment, the present invention includes compounds wherein A is thiazolyl. Also within this embodiment, the present invention includes compounds wherein A is pyridyl.

An embodiment of the present invention includes compounds wherein:

$R^{1a}$, $R^{1b}$ and $R^{1c}$ may be absent if the valency of A does not permit such substitution and are independently selected from the group consisting of:
(1) hydrogen,
(2) halogen,
(3) hydroxyl,
(4) phenyl or napthyl, which is unsubstituted or substituted with halogen, hydroxyl, $C_{1-6}$alkyl, —O—$C_{1-6}$alkyl, —SH, —S—$C_{1-16}$alkyl, —$NO_2$, —$CO_2$—$R^{10}$, —CN, or —$NR^{10}R^{11}$,
(5) —O-phenyl, which is unsubstituted or substituted with halogen, hydroxyl, $C_{1-6}$alkyl, —O—$C_{1-6}$alkyl, —SH, —S—$C_{1-6}$alkyl, —$NO_2$, —$CO_2$—$R^{10}$, —CN, or —$NR^{10}R^{11}$,
(6) $C_{1-6}$alkyl, which is unsubstituted or substituted with halogen, hydroxyl, phenyl or —O—$C_{1-6}$alkyl,
(7) —O—$C_{1-6}$alkyl, which is unsubstituted or substituted with halogen, hydroxyl, phenyl or —O—$C_{1-6}$alkyl,
(8) $C_{3-6}$cycloalkyl, which is unsubstituted or substituted with halogen, hydroxyl or phenyl,
(9) $C_{2-4}$alkenyl, which is unsubstituted or substituted with $C_{3-6}$cycloalkyl or phenyl,
(10) heterocycle, which is unsubstituted or substituted with halogen, hydroxyl, $C_{1-6}$alkyl, —O—$C_{1-6}$alkyl, —SH, —S—$C_{1-6}$alkyl, —$NO_2$, —$CO_2H$, —CN, or —$NR^{10}R^{11}$,
(11) —$NR^{10}R^{11}$, wherein $R^{10}$ and $R^{11}$ are independently selected from hydrogen and $C_{1-6}$alkyl,
(12) —$S(O)_2$—$NR^{10}R^{11}$,
(13) —$S(O)_q$—$R^{12}$, where q is 0, 1 or 2 and where $R^{12}$ is $C_{1-6}$alkyl, $C_{3-6}$cycloalkyl, or phenyl which is unsubstituted or substituted with halogen, hydroxyl, phenyl or —O—$C_{1-6}$alkyl,
(14) —$CO_2H$,
(15) —$CO_2$—$R^{12}$,
(16) —CN, and
(17) —$NO_2$;
or $R^{1a}$ and $R^{1b}$ taken together form a cyclopentyl, cyclohexyl, dihydrofuranyl or dihydropyranyl ring, which is unsubstituted or substituted with —$CH_3$, (=$CH_2$), keto, or hydroxyl.

An embodiment of the present invention includes compounds wherein $R^{1a}$, $R^{1b}$ and $R^{1c}$ are independently selected from the group consisting of:
(1) hydrogen,
(2) halogen,
(3) phenyl or napthyl, which is unsubstituted or substituted with halogen, hydroxyl, $C_{1-6}$alkyl, —O—$C_{1-6}$alkyl, $C_{3-6}$cycloalkyl, —SH, —S—$C_{1-16}$alkyl, —$NO_2$, —$CO_2H$, or —CN,
(4) —O-phenyl, which is unsubstituted or substituted with halogen, hydroxyl, $C_{1-6}$alkyl, —O—$C_{1-6}$alkyl, —SH, —S—$C_{1-6}$allyl, —$NO_2$, —$CO_2H$, or —CN,
(5) $C_{1-6}$alkyl, which is unsubstituted or substituted with halogen, hydroxyl, phenyl or —O—$C_{1-6}$alkyl,
(6) $C_{3-6}$cycloalkyl, which is unsubstituted or substituted with halogen, hydroxyl, phenyl or —O—$C_{1-6}$alkyl,
(7) $C_{2-4}$alkenyl, which is unsubstituted or substituted with $C_{3-6}$cycloalkyl or phenyl,
(8) —$NR^{10}R^{11}$, wherein $R^{10}$ and $R^{11}$ are independently selected from hydrogen and $C_{1-6}$alkyl,
(9) isoxazolyl, which is unsubstituted or substituted with $C_{1-6}$alkyl,
(10) imidazolyl, which is unsubstituted or substituted with $C_{1-6}$alkyl,
(11) morpholinyl, which is unsubstituted or substituted with $C_{1-6}$alkyl,
(12) oxazolyl, which is unsubstituted or substituted with $C_{1-6}$alkyl,
(13) pyrazolyl, which is unsubstituted or substituted with $C_{1-6}$alkyl,
(14) pyrrolidinyl, which is unsubstituted or substituted with halogen,
(15) tetrazolyl, which is unsubstituted or substituted with $C_{1-6}$alkyl,
(16) thienyl, which is unsubstituted or substituted with $C_{1-6}$alkyl,
(17) benzothienyl, which is unsubstituted or substituted with $C_{1-6}$alkyl,
(18) thiophenyl, which is unsubstituted or substituted with $C_{1-6}$alkyl,
(19) triazolyl, which is unsubstituted or substituted with $C_{1-6}$alkyl,
(20) —$NO_2$, and
(21) —CN,
or $R^{1a}$ and $R^{1b}$ taken together form a cyclopentyl, cyclohexyl, dihydrofuranyl or dihydropyranyl ring, which is unsubstituted or substituted with —$CH_3$, (=$CH_2$), keto, or hydroxyl.

Within this embodiment, the present invention includes compounds wherein $R^{1c}$ is hydrogen, and $R^{1a}$ and $R^{1b}$ are selected from the group consisting of:
(1) halogen,
(2) phenyl or napthyl, which is unsubstituted or substituted with halogen, hydroxyl, $C_{1-6}$alkyl, —O—$C_{1-6}$alkyl, $C_{3-6}$cycloalkyl, —SH, —S—$C_{1-6}$alkyl, —$NO_2$, —$CO_2$—$C_{1-6}$alkyl, or —CN,
(3) —O-phenyl, which is unsubstituted or substituted with halogen, hydroxyl, $C_{1-6}$alkyl, —O—$C_{1-6}$alkyl, —SH, —S—$C_{1-6}$alkyl, —$NO_2$, —$CO_2$—$C_{1-6}$alkyl, or —CN,
(4) $C_{1-6}$alkyl, which is unsubstituted or substituted with halogen, hydroxyl, phenyl or —O—$C_{1-6}$alkyl,
(5) $C_{3-6}$cycloalkyl, which is unsubstituted or substituted with halogen, hydroxyl, phenyl or —O—$C_{1-6}$alkyl,
(6) $C_{2-4}$alkenyl, which is unsubstituted or substituted with $C_{3-6}$cycloalkyl or phenyl,
(7) —$NR^{10}R^{11}$, wherein $R^{10}$ and $R^{11}$ are independently selected from hydrogen and $C_{1-6}$alkyl,
(8) isoxazolyl, which is unsubstituted or substituted with $C_{1-6}$alkyl,
(9) imidazolyl, which is unsubstituted or substituted with $C_{1-6}$alkyl,
(10) morpholinyl, which is unsubstituted or substituted with $C_{1-6}$alkyl,
(11) oxazolyl, which is unsubstituted or substituted with $C_{1-6}$alkyl,
(12) pyrazolyl, which is unsubstituted or substituted with $C_{1-6}$alkyl,
(13) pyrrolidinyl, which is unsubstituted or substituted with halogen,
(14) tetrazolyl, which is unsubstituted or substituted with $C_{1-6}$alkyl,
(15) thienyl, which is unsubstituted or substituted with $C_{1-6}$alkyl,
(16) benzothienyl, which is unsubstituted or substituted with $C_{1-6}$alkyl,
(17) thiophenyl, which is unsubstituted or substituted with $C_{1-6}$alkyl, and
(18) triazolyl, which is unsubstituted or substituted with $C_{1-6}$alkyl, or $R^{1a}$ and $R^{1b}$ taken together form a cyclopentyl, cyclohexyl, dihydrofuranyl or dihydropyranyl ring, which is unsubstituted or substituted with —$CH_3$, (=$CH_2$), keto, or hydroxyl.

Within this embodiment, the present invention includes compounds wherein A is phenyl, $R^{1b}$ is hydrogen, $R^{1c}$ is hydrogen and $R^{1a}$ is independently selected from the group consisting of:
(1) halogen,
(2) phenyl, which is unsubstituted or substituted with halogen, hydroxyl, $C_{1-6}$alkyl, —O—$C_{1-6}$alkyl, $C_{3-6}$cycloalkyl, or —$NO_2$,
(3) —O-phenyl, which is unsubstituted or substituted with halogen, hydroxyl, $C_{1-6}$alkyl or —O—$C_{1-6}$alkyl,
(4) $C_{1-6}$alkyl, which is unsubstituted or substituted with halogen, hydroxyl or phenyl,
(5) $C_{3-6}$cycloalkyl, which is unsubstituted or substituted with halogen, hydroxyl or phenyl, and
(6) $C_{2-4}$alkenyl, which is unsubstituted or substituted with $C_{3-6}$cycloalkyl or phenyl.

Within this embodiment, the present invention includes compounds wherein A is phenyl, $R^{1b}$ is hydrogen, $R^{1c}$ is hydrogen and $R^{1a}$ is independently selected from the group consisting of:
(1) isoxazolyl, which is unsubstituted or substituted with $C_{1-6}$alkyl,
(2) imidazolyl, which is unsubstituted or substituted with $C_{1-6}$alkyl,
(3) morpholinyl, which is unsubstituted or substituted with $C_{1-6}$alkyl,
(4) oxazolyl, which is unsubstituted or substituted with $C_{1-6}$alkyl,
(5) pyrazolyl, which is unsubstituted or substituted with $C_{1-6}$alkyl,
(6) pyrrolidinyl, which is unsubstituted or substituted with halogen,
(7) tetrazolyl, which is unsubstituted or substituted with $C_{1-6}$alkyl,
(8) thienyl, which is unsubstituted or substituted with $C_{1-6}$alkyl,
(9) benzothienyl, which is unsubstituted or substituted with $C_{1-6}$alkyl,
(10) thiophenyl, which is unsubstituted or substituted with $C_{1-6}$alkyl, and
(11) triazolyl, which is unsubstituted or substituted with $C_{1-6}$alkyl.

Within this embodiment, the present invention includes compounds wherein A is phenyl, $R^{1a}$ is phenyl which is unsubstituted or substituted with one or more halogen, $R^{1b}$ is hydrogen and $R^{1c}$ is hydrogen.

Within this embodiment, the present invention includes compounds wherein A is phenyl, $R^{1a}$ is 4-phenyl, $R^{1b}$ is hydrogen and $R^{1c}$ is hydrogen.

Within this embodiment, the present invention includes compounds wherein A is phenyl, $R^{1a}$ is $C_{1-6}$alkyl, $R^{1b}$ is hydrogen and $R^{1c}$ is hydrogen.

Within this embodiment, the present invention includes compounds wherein A is phenyl, $R^{1a}$ is isopropyl or tert-butyl, $R^{1b}$ is hydrogen and $R^{1c}$ is hydrogen.

Within this embodiment, the present invention includes compounds wherein A is phenyl, $R^{1a}$ is located at the 4-position of the phenyl, $R^{1b}$ is hydrogen and $R^{1c}$ is hydrogen.

An embodiment of the present invention includes compounds wherein $R^{1a}$ is other than —$CO_2CH_3$.

An embodiment of the present invention includes compounds wherein $R^2$ and $R^3$ are independently selected from the group consisting of:
(1) hydrogen,
(2) halogen,
(3) $C_{1-6}$alkyl, which is unsubstituted or substituted with halo, $C_{3-6}$cycloalkyl or phenyl, and
(4) $C_{3-6}$cycloalkyl, which is unsubstituted or substituted with halo, $C_{3-6}$cycloalkyl or phenyl.

Within this embodiment, the present invention includes compounds wherein $R^2$ and $R^3$ are independently selected from the group consisting of:
(1) hydrogen,
(2) fluoro,
(3) $C_{1-6}$alkyl, which is unsubstituted or substituted with halogen or $C_{3-6}$cycloalkyl, and
(4) $C_{3-6}$cycloalkyl.

Within this embodiment, the present invention includes compounds wherein $R^2$ is hydrogen and $R^3$ is hydrogen. Within this embodiment, the present invention includes compounds wherein $R^2$ is fluoro and $R^3$ is fluoro. Within this embodiment, the present invention includes compounds wherein $R^2$ is methyl and $R^3$ is hydrogen. Within this embodiment, the present invention includes compounds wherein $R^2$ is cyclopropyl and $R^3$ is hydrogen.

An embodiment of the present invention includes compounds wherein $R^4$ is other than hydrogen.

Within this embodiment, the present invention includes compounds wherein $R^4$ is in the (R) orientation.

An embodiment of the present invention includes compounds wherein $R^4$ is selected from the group consisting of:
(1) $C_{1-6}$alkyl, which is unsubstituted or substituted with halogen, hydroxyl, —O—$C_{1-6}$alkyl, $C_{3-6}$cycloalkyl, phenyl, or —$NR^{10}R^{11}$, wherein $R^{10}$ and $R^{11}$ are independently selected from the group consisting of hydrogen, and $C_{1-6}$alkyl, which is unsubstituted or substituted with halogen, hydroxyl or phenyl,
(2) —$C_{3-6}$cycloalkyl, which is unsubstituted or substituted with halogen, $C_{1-6}$alkyl or phenyl,
(3) —$C_{2-6}$alkenyl,
(4) phenyl, which is unsubstituted or substituted with halogen, hydroxyl, $C_{1-6}$alkyl, —O—$C_{1-6}$alkyl or —$NO_2$,
(5) —(C=O)—$NR^{10}R^{11}$, and
(6) —(C=O)—O—$C_{1-6}$alkyl, which is unsubstituted or substituted with halogen, $C_{3-6}$cycloalkyl or phenyl.

An embodiment of the present invention includes compounds wherein $R^4$ is selected from the group consisting of:
(1) $C_{1-6}$alkyl, which is unsubstituted or substituted with halogen, hydroxyl, or —O—$C_{1-6}$alkyl, and
(2) —$C_{2-6}$alkenyl,
(3) —$C_{3-6}$cycloalkyl.

Within this embodiment, the present invention includes compounds wherein $R^4$ is selected from the group consisting of:
(1) $CH_3$,
(2) $CH_2OH$,
(3) $CH_2OCH_3$,
(4) $CH_2CH_3$,
(5) CH=$CH_2$,
(6) $CH_2CH_2OH$,
(7) $CH_2CH$=$CH_2$,
(8) $CH_2CH_2F$,
(9) $CH_2CF_2$,
(10) $CH_2$-phenyl,
(12) $CH_2$-cyclopropyl,
(13) $CH_2$-cyclobutyl,
(14) cyclopropyl,
(15) cyclobutyl,
(16) $CH_2CH_2CH_3$, and
(17) —(C=O)—O—$CH_3$.

Within this embodiment, the present invention includes compounds wherein $R^4$ is $CH_3$, $CH_2CH_3$, $CH_2OH$, $CH_2CH_2OH$ or cyclopropyl.

Within this embodiment, the present invention includes compounds wherein $R^4$ is $CH_3$.

Within this embodiment, the present invention includes compounds wherein $R^4$ is (R)—$CH_3$.

An embodiment of the present invention includes compounds wherein $R^{5a}$, $R^{5b}$ and $R^{5c}$ are independently selected from the group consisting of:
(1) hydrogen,
(2) halogen,
(3) hydroxyl,
(4) $C_{1-6}$alkyl, which is unsubstituted or substituted with halogen, hydroxyl, phenyl, —O—$C_{1-6}$alkyl, —O—(CO)$C_{1-6}$alkyl or $C_{3-6}$cycloalkyl, and
(5) —$C_{2-4}$alkenyl.

An embodiment of the present invention includes compounds wherein $R^{5a}$, $R^{5b}$ and $R^{5c}$ are independently selected from the group consisting of:
(1) hydrogen,
(2) —O—$C_{1-6}$alkyl, which is unsubstituted or substituted with halogen, hydroxyl, phenyl, —O—$C_{1-6}$alkyl, or $C_{3-6}$cycloalkyl,
(3) $C_{3-6}$cycloalkyl, which is unsubstituted or substituted with halogen, hydroxyl or phenyl,
(4) —NH—$C_{1-6}$alyl, which is unsubstituted or substituted with halogen, hydroxyl, phenyl, —O—$C_{1-6}$alkyl, —O—(CO)$C_{1-6}$alkyl, or $C_{3-6}$cycloalkyl,
(5) —N($C_{1-6}$alkyl)$_2$, which each alkyl independently is unsubstituted or substituted with halogen, hydroxyl, phenyl, —O—$C_{1-6}$alkyl, —O—(CO)$C_{1-6}$alkyl, or $C_{3-6}$cycloakyl,
(6) phenyl, which is unsubstituted or substituted with halogen, hydroxyl, $C_{1-6}$alkyl, —O—$C_{1-6}$alkyl or —$NO_2$,
(7) —O-phenyl, which is unsubstituted or substituted with halogen, hydroxyl, $C_{1-6}$alkyl,
—O—$C_{1-6}$alkyl or —$NO_2$,
(8) —$S(O)_2$—NH—$C_{1-6}$alkyl,
(9) —$S(O)_2$—N($C_{1-6}$alkyl)$_2$, and
(10) —$S(O)_2$—$C_{1-6}$alkyl.

An embodiment of the present invention includes compounds wherein $R^{5a}$, $R^{5b}$ and $R^{5c}$ are independently selected from the group consisting of:
(1) hydrogen,
(2) heterocycle, which is unsubstituted or substituted with halogen, hydroxyl, keto, $C_{1-6}$alkyl or —O—$C_{1-6}$alkyl,
(3) —O-heterocycle, which is unsubstituted or substituted with halogen, hydroxyl, keto, $C_{1-6}$alkyl or —O—$C_{1-6}$alkyl, and
(4) —NH-heterocycle, which is unsubstituted or substituted with halogen, hydroxyl, keto, $C_{1-6}$alkyl or —O—$C_{1-6}$alkyl.

An embodiment of the present invention includes compounds wherein $R^{5b}$ is hydrogen, $R^{5c}$ is hydrogen and $R^{5a}$ is independently selected from the group consisting of:
(1) hydrogen,
(2) fluoro,
(3) chloro,
(4) bromo,
(5) hydroxyl,
(6) —$CH_3$,
(7) —$CH_2OH$,
(8) —$CH_2CH_3$,
(9) —$CH_2$=$CH_2$,
(10) —$CH_2CH_2CH_3$, and
(11) -cyclopropyl.

Within this embodiment, the present invention includes compounds wherein $R^{5b}$ is hydrogen, $R^{5c}$ is hydrogen and $R^{5a}$ is —O—$C_{1-6}$alkyl, which is unsubstituted or substituted with halogen, hydroxyl, phenyl, —O—$C_{1-6}$alkyl, or $C_{3-6}$cycloalkyl.

Within this embodiment, the present invention includes compounds wherein $R^{5b}$ is hydrogen, $R^{5c}$ is hydrogen and $R^{5a}$ is independently selected from the group consisting of:
(1) hydrogen,
(2) —$OCH_3$,
(3) —$OCH_2F$,
(4) —$OCH_2$-cyclopropyl,
(5) —$OCH_2$-phenyl,
(6) —$OCH_2CH_3$,
(7) —$OCH_2CF_3$,
(8) —$OCH_2CH_2CH_3$,
(9) —$OCH_2(C$=$O)OCH_2CH_3$,
(10) —$OCH_2(C$=$O)NHCH_2CH_3$,
(11) —$OSO_2CH_3$, and
(12) —$O(C$=$O)OCH_3$.

Within this embodiment, the present invention includes compounds wherein $R^{5b}$ is hydrogen, $R^{5c}$ is hydrogen and $R^{5a}$ is —$OCH_2CF_3$.

Within this embodiment, the present invention includes compounds wherein $R^{5b}$ is hydrogen, $R^{5c}$ is hydrogen and $R^{5a}$ is independently selected from the group consisting of:
(1) hydrogen,
(2) —$NHCH_2CF_3$,
(3) —$NHCH_2C(CH_3)_3$,
(4) —$NHCH_2CH_2C(CH_3)_3$,
(5) —$NHCH(CH_3)CH_2CH_3$,
(6) —NH-cyclopropyl, and
(7) —$NHCH_2$-cyclopropyl.

Within this embodiment, the present invention includes compounds wherein $R^{5b}$ is hydrogen, $R^{5c}$ is hydrogen and $R^{5a}$ is independently selected from the group consisting of:
(1) hydrogen,
(2) pyridyl,
(3) —O-pyridyl,
(4) —NH-pyridyl,
(5) imidazolyl,
(6) oxazolyl,
(7) pyrrolyl,
(8) pyrrolidinyl, which is unsubstituted or substituted with $C_{1-6}$alkyl, keto or halo,
(9) morpholinyl, which is unsubstituted or substituted with $C_{1-6}$alkyl,
(10) thiomorpholinyl, which is unsubstituted or substituted with $C_{1-6}$alkyl, and
(11) piperazinyl, which is unsubstituted or substituted with $C_{1-6}$alkyl.

Within this embodiment, the present invention includes compounds wherein $R^{5b}$ is hydrogen and $R^{5c}$ is hydrogen.

Within this embodiment, the present invention includes compounds wherein $R^{5a}$ is located at the 5-position of the pyridyl, $R^{5b}$ is hydrogen and $R^{5c}$ is hydrogen.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. Similarly, $C_{2-6}$alkenyl is defined to identify the group as having 2, 3, 4, 5 or 6 carbons which incorporates at least one double bond, which may be in a E- or a Z-arrangement. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof and S-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonizing T-type calcium channel activity in a patient such as a mammal in need of such inhibition comprising the administration of an effective amount of the compound. The present invention is directed to the use of the compounds disclosed herein as antagonists of T-type calcium channels activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing T-type calcium channel activity or treating the disorders and diseases noted herein in humans and animals.

The subject treated in the present methods is generally a mammal, in particular, a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as T-type calcium channel antagonists may be readily determined without undue experimentation by methodology well known in the art, including the "FLIPR $Ca^{2+}$ Flux Assay" and the "T-type Calcium ($Ca^{2+}$) Antagonist Voltage-Clamp Assay" [described by Xia, et al., Assay and Drug Development Tech., 1(5), 637-645 (2003)]. In a typical experiment ion channel function from HEK 293 cells expressing the T-type channel alpha-1G, H, or I (CaV 3.1, 3.2, 3.3) is recorded to determine the activity of compounds in blocking the calcium current mediated by the T-type channel alpha-1G, H, or I (CaV 3.1, 3.2, 3.3). In this T-type calcium ($Ca^{2+}$) antagonist voltage-clamp assay calcium currents are elicited from the resting state of the human alpha-1G, H, or I (CaV 3.1, 3.2, 3.3) calcium channel as follows. Sequence information for T-type (Low-voltage activated) calcium channels are fully disclosed in e.g., U.S. Pat. Nos. 5,618,720, 5,686,241, 5,710,250, 5,726,035, 5,792,846, 5,846,757, 5,851,824, 5,874,236, 5,876,958, 6,013,474, 6,057,114, 6,096,514, WO 99/28342, and J. Neuroscience, 19(6): 1912-1921 (1999). Cells expressing the T-type channels were grown in growth media which comprised: DMEM, 10% Tet-system approved FBS (Clontech Laboratories Inc.), 100 microgram/ml Penicillin/Streptomycin, 2 mM L-Glutamine, 150 microgram/ml Zeocin, 5 microgram/ml Blasticidin. T-channel expression was induced by exposing the cells to 2 mM Tetracycline for 24 hrs. Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. Trypsinization buffer was 0.05% Trypsin, 0.53 mM EDTA. The extracellular recording solution consists of (mM): 130 mM NaCl, 4 mM KCl, 1 mM MgCl2, 2 mM CaCl2, 20 mM HEPES, 30 Glucose, pH 7.4. The internal solution consists of (mM): 125 CsCl, 10 TEA-Cl, 10 HEPES, 8 NaCl, 0.06 CaCl2, 0.6 EGTA, 4 ATP-Mg, 0.3 GTP; 135 mM CsMeSO3, 1 MgCl2, 10 CsCl, 5 EGTA, 10 HEPES, pH 7.4; or 135 mM CsCl, 2 MgCl2, 3 MGATP, 2 Na2ATP, 1 Na2GTP, 5 EGTA, 10 HEPES, pH 7.4. Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell Ca2+ current response. Voltage protocols: (1) –80 mV holding potential every 20 seconds pulse to –20 mV for 70 msec duration; the effectiveness of the drug in inhibiting the current mediated by the channel is measured directly from measuring the reduction in peak current amplitude initiated by the voltage shift from –80 mV to –20 mV; (2). –100 mV holding potential every 15 seconds pulse to –20 mV for 70 msec duration; the effectiveness of the drug in inhibiting the current mediated by the channel is measured directly from measuring the reduction in peak current amplitude initiated by the shift in potential from –100 mV to –20 mV. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed on. Once steady state inhibition at a given compound concentration is reached, a higher concentration of compound is applied. % inhibition of the peak inward control Ca2+ current during the depolarizing step to –20 mV is plotted as a function of compound concentration.

The intrinsic T-type calcium channel antagonist activity of a compound which may be used in the present invention may be determined by these assays. In particular, the compounds of the following examples had activity in antagonizing the T-type calcium channel in the aforementioned assays, generally with an $IC_{50}$ of less than about 10 μM. Some of the compounds within the present invention had activity in antagonizing the T-type calcium channel in the aforementioned assays with an $IC_{50}$ of less than about 1 μM. Such a result is indicative of the intrinsic activity of the compounds in use as antagonists of T-type calcium channel activity.

With respect to other compounds disclosed in the art, the present compounds exhibit unexpected properties, such as with respect to duration of action and/or metabolism, such as increased metabolic stability, enhanced oral bioavailability or absorption, and/or decreased drug-drug interactions.

T-type calcium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with calcium channels, including one or more of the following conditions or diseases: movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); heart disease, abnormal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoci onus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); attention deficit/hyperactivity disorder (ADHD); conduct disorder; migraine (including migraine headache); urinary incontinence; overactive bladder (OAB); urge urinary incontinence (UUI); lower urinary tract symptoms (LUTS); substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute pain, chronic pain, severe pain, intractable pain, inflammatory pain, chronic inflammatory pain, diabetic neuropathy, chronic neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in an embodiment the present invention provides methods for: treating, controlling, ameliorating or reducing the risk of epilepsy, including absence epilepsy; treating or controlling Parkinson's disease; treating essential tremor; treating or controlling pain, including neuropathic pain; enhancing the quality of sleep; augmenting sleep maintenance; increasing REM sleep; increasing slow wave sleep; decreasing fragmentation of sleep patterns; treating insomnia; enhancing cognition; increasing memory retention; treating or controlling depression; treating or controlling psychosis; or treating, controlling, ameliorating or reducing the risk of schizophrenia, in a mammalian patient in need thereof which comprises administering to the patient a therapeutically effective amount of the compound of the present invention. The subject compounds are further useful in a method for the prevention, treatment, control, amelioration, or reducation of risk of the diseases, disorders and conditions noted herein.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of T-type calcium channel. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient-per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be employed in combination with an anti-seizure agent such as carbamazepine, clonazepam, divalproex, ethosuximide, felbamate, fosphenyloin, gabapentin, lamotrigine, levetiracetam, lorazepam, midazolam, oxcarbazepine, phenobarbital, phenyloin, primidone, tiagabine, topiramate, valproate, vigabatrin or zonisamide. In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, trifluoperazine or valproic acid.

In another embodiment, the compounds of the present invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compounds of the present invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the compounds of the present invention may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. In another embodiment, the subject compound may be employed in combination with an L-type calcium channel antagonist, such as amlodipine. In another embodiment, the subject compound may be employed in combination with an NK-1 receptor antagonists, a beta-3 agonist, a 5-alpha reductase inhibitor (such as fmasteride or dutasteride), a M3 muscarinic receptor antagonist (such as darifenacin, fesoterodine, oxybutynin, solifenacin, tolterodine or trosipium) or duloxetine.

In another embodiment, the compounds of the present invention may be administered in combination with compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, other T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepamn, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the compounds of the present invention may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the compounds of the present invention may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; or neuronal nicotinic agonists.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyllithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; $Et_3N$: triethylamine; DCM: dichloromethane; DCE: dichloroethane; DME: dimethoxyethane; DEA: diethylamine; DAST: diethylaminosulfur trifluoride; EtMgBr: ethylamgnesium bromide; BSA: bovine serum albumin; TFA: trifluoracetic acid; DMF: N,N-dimethylformamide; $SOCl_2$: thionyl chloride; CDI: carbonyl diimidazole; rt: room temperature; HPLC: high performance liquid chromatography. The compounds of the present invention can be prepared in a variety of fashions.

In some cases the final product may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

SCHEME 1

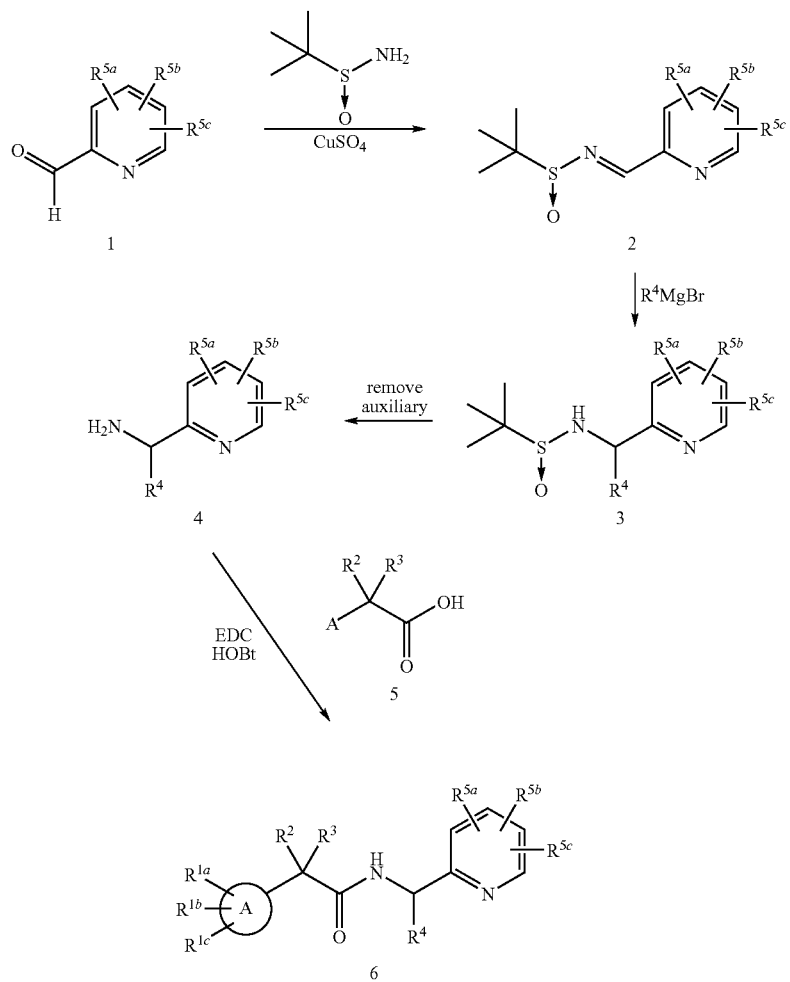

Compounds of the invention may be prepared as outlined in Scheme 1. An appropriately substituted 2-formylpyridine 1 is condensed with tert-butane sulfinamide and addition of an organometallic reagent introduces the $R^4$ substituent. Removal of the auxiliary provides amines 4 which can be coupled to a variety of carboxylic acid derivatives 5 to afford compounds of the formula 6. Compound of the formula 6 can be further modified by manipulation of the substituent groups by general methods known in the art, including (but not limited to) cross coupling, oxidation, reduction, dealkylation, alkylation, acylation and the like.

SCHEME 2

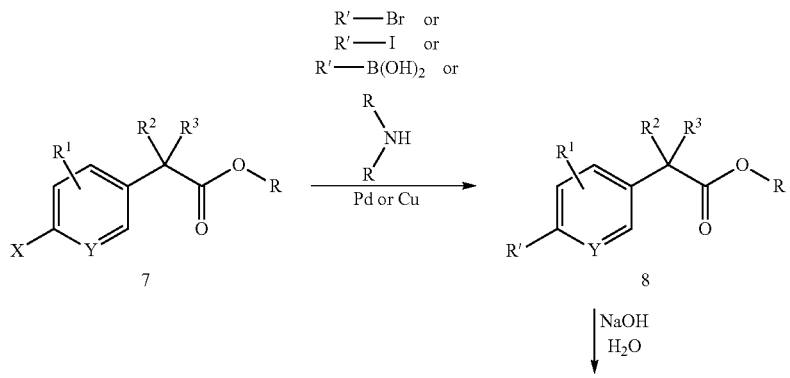

-continued

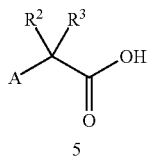

Intermediate carboxylic acid derivatives of formula 5 may be prepared as shown in Scheme 2. Thermal or metal mediated (e.g. palladium or copper) coupling of appropriately substituted halides, amines, and boronic acids with appropriately substituted esters 7 give esters of the formula 8 which can be hydrolyzed to the desired acids 5.

EXAMPLE 1

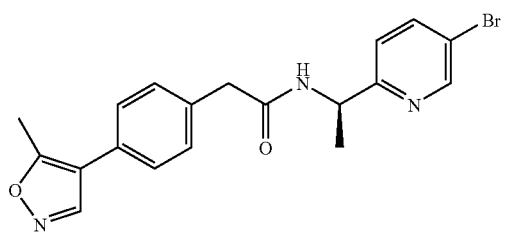

N-[(1R)-1-(5-bromopyridin-2-ylethyl]-2-[4-(5-methylisoxazol-4-yl)phenyl]acetamide 2-(acetoxymethyl)-5-bromopyridine: To a solution of 2-methyl-5-bromopyridine (40 g, 0.23 mol) in dichloromethane (500 ml) was added M-CPBA (64 g, 0.25 mol) in batches at 0° C. After stirring for 16 h at room temperature, the mixture was washed with sat. aq. $NaHCO_3$, aq. $NaHSO_3$ and brine successively. The organic layer was dried over $MgSO_4$ and then concentrated to give 35 g, (79.2%) of 2-acetoxymethyl-5-bromopyridine as a yellow solid. A mixture of 35 g (0.19 mol) 2-acetoxymethyl-5-bromopyridine and $Ac_2O$ (160 ml) was heated to reflux for 1 hour. To this mixture was cautiously added 150 mL EtOH (until the excess AC20 was converted to EtOAc and AcOH). After concentration, the residue was neutralized with aq. $KHCO_3$ and extracted with $CH_2Cl_2$. The extract was dried over $MgSO_4$ and purified by silica gel chromatography to give 2-(acetoxymethyl)-5-bromopyridine. $^1$H-NMR (400 MHz, $CDCl_3$) δ 8.65 (d, J=2.4 Hz, 1H), 7.82 (q, $J_1$=8.4 Hz, $J_2$=2.4 Hz, 1H), 7.25 (q, $J_1$=7.8 Hz, $J_2$=0.6 Hz, 1H), 5.17 (s, 2H), 2.16 (s, 3H) m/z: 231.15 $(M^{+1})$ 2-hydroxymethyl-5-bromopyridine A solution of 40 g (170 mmol) 2-(acetoxymethyl)-5-bromopyridine in conc. HCl (200 ml) was heated to reflux for 1 hour. The solution was concentrated in vacuo and the residue was neutralized with aq. $KHCO_3$ and extracted with $CH_2Cl_2$. Concentration of the extract afforded 2-hydroxymethyl-5-bromopyridine. $^1$H-NMR (400 MHz, DMSO) δ 8.57 (d, J=2.4 Hz, 1H), 8.00 (m, 1H), 7.42 (q, $J_1$=8.4 Hz, $J_2$=0.6 Hz, 1H), 5.49 (t, J=5.4 Hz, 1H), 4.50 (d, J=4.8 Hz, 2H) m/z: 189.12 $(M^{+1})$ (R)—N-[(1E)-(5-bromopyridin-2-yl)methylene]-2-methylpropane-2-sulfinamide To a 0° C. solution of 2-hydroxymethyl-5-bromopyridine (20 g, 0.106 mol) in $CHCl_3$ (450 ml) was added active $MnO_2$ (50 g, 0.57 mol) and the reaction mixture was then refluxed for 2 h. The reaction mixture was filtered, and the filter cake was washed with boiling $CHCl_3$ three times. The filtrate was washed with brine, dried over $MgSO_4$, and filtered. To the filtrate was added 13.3 g (0.1 μmol) (R) t-butanesulfinamide and 35 g (0.22 mol) $CuSO_4$ and the resulting mixture stirred at room temperature for 16 hours then filtered and concentrated in vacuo. The residue was purified by silica gel chromatography to afford (R)—N-[(1E)-(5-bromopyridin-2-yl)methylene]-2-methylpropane-2-sulfinamide m/z: 290.29 (M+1).

(1R)-1-(5-bromopyridin-2-yl)ethanamine

To a −78° C. solution of (R)—N-[(1E)-(5-bromopyridin-2-yl)methylene]-2-methylpropane-2-sulfinamide (16 g, 55.4 mmol) in THF (300 ml) was added a solution of methylmagnesium bromide in THF (3 M, 65 ml, 0.19 mol). After stirring for 45 min at −78° C., the reaction was quenched by the addition of saturated aq. ammonium chloride and the resulting mixture was extracted with ethyl acetate. The combined organic layers were washed with brine, dried over $MgSO_4$, filtered, and concentrated to afford 16 g of oil. To this oil was added to a solution of HCl in MeOH (200 ml), and the mixture was stirred at room temperature for 30 min. The resulting mixture was concentrated in vacuo. To the residue was added fresh ethanol, and the mixture was concentrated again. Crystallization from EtOH and ether provided 1(1R)-1-(5-bromopyridin-2-yl)ethanamine $^1$H-NMR (400 MHz, DMSO) δ 8.74 (d, J=2.4 Hz, 1H), 8.59 (s, 3H), 8.14 (q, $J_1$=8.4 Hz, $J_2$=2.4 Hz, 1H), 7.55 (d, J=8.1 Hz, 1H), 4.49 (m, 1H), 1.47 (d, J=6.9 Hz, 3H) m/z: 201.89 $(M^{+1})$

[4-(5-methylisoxazol-4-yl)phenyl]acetic acid

To a solution of 0.50 g (1.91 mmol) 2-[4-(4,4,5,5-tetramethyl-1,3,2-dioxaboro-1an-2-yl)phenylacetic acid in 1.90 ml $CH_3CN$ and 1.90 ml water was added 0.48 g (2.29 mmol) 4-iodo-5-methyl-isoxazole, 0.08 g (0.12 mmol) TXPTS, 0.01 g (0.05 mmol) Palladium (II) acetate, and 0.54 mL (3.82 mmol) diisopropylamine. After 20 min in the microwave at 120° C., the reaction mixture was cooled, acidified to a pH of 1 with 1N HCl, extracted with $CH_2Cl_2$, and washed with brine. The organic layer was dried over $NaSO_4$, filtered and concentrated in vacuo and afforded 0.57 g of ([4-(5-methyl-isoxazol-4-yl)phenyl]acetic acid that was used without further purification. $^1$H NMR ($CDCl_3$, 400 MHz) 7.50-7.47 (m, 2H); 7.39-7.33 (m, 3H); 7.32-7.26 (m, 1H); 3.70 (s, 2H). Electrospray mass spec M+H=218.1.

N-[(1R)-1-(5-bromopyridin-2-yl)ethyl]-2-[4-(5-methylisoxazol-4-yl)phenyl]acetamide To a solution of 0.20 g (0.921 mmol) [4-(5-methylisoxazol-4-yl)phenyl]acetic acid in 2.00 ml DMF was added 0.22 g (0.92 mmol) (1R)-1-(5-bromopyridin-2-yl)ethanamine hydrochloride salt, 0.16 g (1.20 mmol) HOAT, 0.23 g (1.20 mmol) EDC, and 0.48 mL (2.76 mmol) DIEA. After 1.5 h at room temperature, the reaction mixture was diluted with $CH_2Cl_2$, washed three times with water, and washed with brine. The organic layer was dried over $NaSO_4$, filtered and concentrated in vacuo. Purification by flash chromatography (1×14 cm silica gel, linear gradient 38-85% EtOAc:hexane) afforded N-[(1R)-1-(5-bromopyridin-2-yl)ethyl]-2-[4-(5-methylisoxazol-4-yl)phenyl]acetamide. $^1$H NMR ($CDCl_3$, 400 MHz) 8.53 (d, 1H, J=2.11 Hz); 8.35 (s, 1H); 7.76 (dd, 1H, J=2.38 Hz, 8.33 Hz); 7.35 (s, 4H); 7.13 (d, 1H, J=8.24 Hz); 6.73 (br d, 1H, J=6.32 Hz); 5.11 (m, 1H); 3.61 (s, 2H); 2.58 (s, 3H); 1.42 (d, 3H, J=6.87). Electrospray mass spec M+H=402.0.

EXAMPLE 2

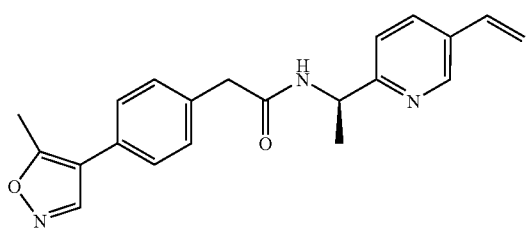

2-[4-(5-methylisoxazol-4-yl)phenyl]-N-[(1R)-1-(5-vinylpyridin-2-yl)ethyl]acetamide To a solution of 0.18 g (0.46 mmol) N-[(1R)-1-(5-bromopyridin-2-yl)ethyl]-2-[4-(5-methylisoxazol-4-yl)phenyl]acetamide in 0.50 ml $CH_3CN$ and 0.50 ml water was added 0.07 g (0.46 mmol) 2-vinyl-4,4,5,5-tetramethyl-1,3,2-dioxaborolane, 0.02 g (0.03 mmol) TXPTS, 0.003 g (0.01 mmol) Palladium (II) acetate, and 0.13 mL (0.92 mmol) diisopropylamine. After 20 min in the microwave at 120° C., the reaction mixture was cooled, extracted with $CH_2Cl_2$, and washed with brine. The organic layer was dried over $NaSO_4$, filtered, and concentrated in vacuo. Purification by flash chromatography (1×14 cm silica gel, linear gradient 40-85% EtOAc:hexane) afforded 2-[4-(5-methylisoxazol-4-yl)phenyl]-N-[(1R)-1-(5-vinylpyridin-2-yl)ethyl]acetamide. Electrospray mass spec M+H=348.1.

EXAMPLE 3

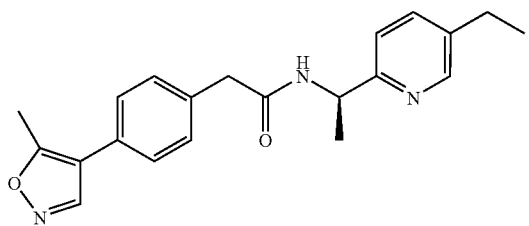

N-[(1R)-1-(5-ethylpyridin-2-yl)ethyl]-2-[4-(5-methylisoxazol-4-yl)phenyl]acetamide To a solution of 0.11 g (0.32 mmol) 2-[4-(5-methylisoxazol-4-yl)phenyl]-N-[(1R)-1-(5-vinylpyridin-2-yl)ethyl]acetamide in 1.30 ml EtOAc was added 0.010 g of 10% palladium on carbon. The reaction flask was equipped with a hydrogen balloon. After 24 h at room temperature, the reaction mixture was filter through celite, washed three times with methanol, and concentrated in vacuo. Purification by automated flash chromatography (40 g silica gel cartridge 20-100% EtAOc/hex over 15 min) afforded N-[(1R)-1-(5-ethylpyridin-2-yl)ethyl]-2-[4-(5-methylisoxazol-4-yl)phenyl]acetamide $^1$H NMR ($CDCl_3$, 400 MHz) 8.35 (s, 1H); 8.31 (d, 1H, J=1.56 hz); 7.47 (dd, 1H, J=2.19 Hz, 7.96 Hz); 7.36 (d, 4H, J=2.29 Hz); 7.13 (d, 1H, J=7.88 Hz); 6.97 (br d, 1H J=7.88 Hz); 5.10 (m, 1H); 3.62 (s, 2H); 2.63 (q, 2H, J=7.60 Hz, 15.11 Hz); 2.57 (s, 3H); 1.43 (d, 3H, J=6.69); 1.24 (t, 3H, J=7.60). HRMS (ES) exact mass calcd for $C_{21}H_{23}N_3O_2$: 350.1864, Found: 350.1856.

EXAMPLE 4

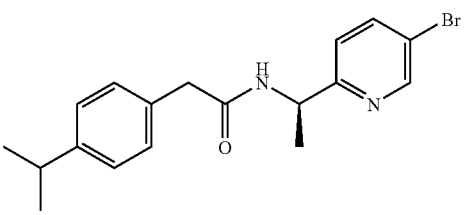

N-[(1R)-1-(5-bromopyridin-2-ylethyl]-2-(4-isopropylphenyl)acetamide

To a suspension of 4-isopropylphenylacetic acid (0.356 g, 2.000 mmol), (1R)-1-(5-bromopyridin-2-yl)ethanamine hydrochloride (0.475 g, 2.000 mmol), 1-(3-dimethylaminopropyl)-3-ethylcarbodiimide hydrochloride (0.383 g, 2.000 mmol), and 1-hydroxy-7-azabenzotriazole (0.272 g, 2.000 mmol) in 15.0 ml of $CH_2Cl_2$ was added slowly triethylamine (0.836 ml, 6.000 mmol). The resulting solution was stirred at room temperature for 3 hours. The reaction mixture was washed with saturated sodium bicarbonate solution and brine. Organics were extracted with $CH_2Cl_2$, dried over $Na_2SO_4$, filtered and concentrated in vacuo. Purification by normal phase chromatography (0-80% EtOAc/Hex) gave N-[(1R)-1-(5-bromopyridin-2-yl)ethyl]-2-(4-isopropylphenyl)acetamide as a white solid. $^1$H NMR ($CDCl_3$, 400 MHz) δ 8.503 (d, J=2.20 Hz, 1H); 7.740 (dd, J=2.20 Hz, J=8.30 Hz, 1H); 7.207 (d, J=8.30 Hz, 2H); 7.182 (d, J=8.30 Hz, 2H); 7.102 (d, J=8.30 Hz, 1H); 6.591 (br d, J=7.08 Hz, 1H); 5.094 (dq, J=7.08 Hz, 1H); 3.571 (d, J=15.87 Hz, 1H); 3.536 (d, J=16.11 Hz, 1H); 2.907 (sept, J=6.83 Hz, 1H); 1.391 (d, J=6.59 Hz, 3H); 1.254 (d, J=6.83 Hz, 6H); MS (Electrospray): m/z 361.0 (M+H).

EXAMPLE 5

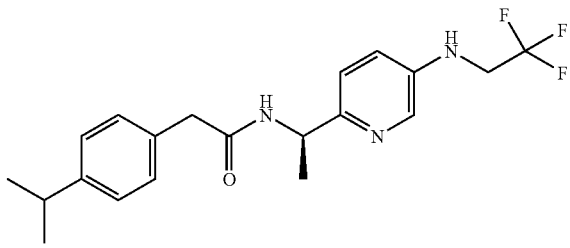

2-(4-isopropylphenyl)-N-((1R)-1-{5-[(2,2,2-trifluoroethyl)amino]pyridin-2-yl}ethyl)acetamide To a 10.0 ml microwave reaction tube was added N-[(1R)-1-(5-bromopyridin-2-yl)ethyl]-2-(4-isopropylphenyl)acetamide (0.100 g, 0.277 mmol), trifluoroethylamine (0.025 ml, 0.332 mmol), NaOtBu (0.042 g, 0.441 mmol), (+/−)-2,2'-bis(diphenylphosphino)-1,1'-binaphthyl (0.018 g, 0.029 mmol), tris(dibenzylideneacetone)dipalladium(0) (0.013 g, 0.015 mmol) and 2.5 ml of anhydrous toluene. $N_2$ was bubbled through the mixture while stirring for 5 minutes. Then it was heated at 120° C. for 15 minutes in a microwave reaction chamber. Cooled to room temperature, filtered and concentrated. The residue was purified using reverse phase HPLC to afford 2-(4-isopropylphenyl)-N-((1R)-1-{5-[(2,2,2-trifluoroethyl)amino]pyridin-2-yl}ethyl)acetamide as a white solid. $^1$H NMR (CDCl$_3$, 400 MHz) δ 8.291 (d, J=6.84 Hz, 1H); 8.174 (s, 1H); 7.516 (d, J=8.79 Hz, 1H); 7.357 (d, J=8.79 Hz, 1H); 7.167 (d, J=8.30 Hz, 2H); 7.141 (d, J=8.30 Hz, 2H); 5.823 (br s, 1H); 5.106 (dq, J=7.32 Hz, 1H); 3.692 (br d, J=7.57 Hz, 2H); 3.543 (d, J=14.90 Hz, 1H); 3.501 (d, J=15.14 Hz, 1H); 2.852 (sept, J=6.83 Hz, 1H); 1.563 (d, J=7.08 Hz, 3H); 1.199 (d, J=7.08 Hz, 6H); MS (Electrospray): m/z 380.1 (M+H).

EXAMPLE 6

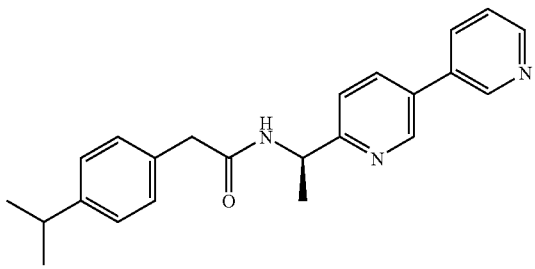

N-[(1R)-1-(3,3'-bipyridin-6-yl)ethyl]-2-(4-isopropylphenyl)acetamide

To a mixture of N-[(1R)-1-(5-bromopyridin-2-yl)ethyl]-2-(4-isopropylphenyl)-acetamide (40 mg, 0.11 mmol), tetrakis(triphenyl)phosphine)palladium (0) (1.3 mg, 0.01 mmol), sodium carbonate (22 mg, 0.20 mmol) in DME/water (4:1, 3.0 ml) was added 3-pyridyl boronic acid (19 mg, 0.16 mmol). The reaction was heated for ten minutes in the Smith Personal microwave system at 100° C. and then washed with brine. Organics were extracted with EtOAc and dried over Na$_2$SO$_4$, filtered and concentrated in vacuo to give a red oily solid. Reverse phase prep HPLC chromatography afforded the mono-trifluoroacetate salt of N-[(1R)-1-(3,3'-bipyridin-6-yl)ethyl]-2-(4-isopropylphenyl)acetamide as an oil. $^1$H NMR (CD$_3$OD, 400 MHz) δ 9.18 (s, 1H); 8.95 (s, 1H); 8.84 (d, J=4.80 Hz, 1H); 8.78 (dd, J=1.20 Hz and 6.40 Hz, 1H); 8.29 (dd, J=2.40 and 8.40 Hz, 1H); 8.06 (dd, J=5.20 and 8.20 Hz, 1H); 7.61 (d, J=8.40 Hz, 1H); 7.19 (m, 4H); 5.10 (q, J=6.80 Hz, 1H); 3.55 (s, 2H); 2.86 (m, 1H); 1.55 (d, J=7.20 Hz, 3H); 1.21 (d, J=6.80 Hz, 6H); HRMS (ES) exact mass calcd for C23, H25, N3O: 360.2071, Found: 360.2070

EXAMPLE 7

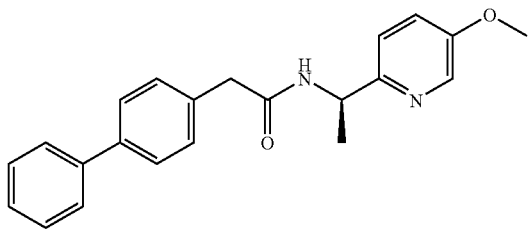

2-(1,1'-biphenyl-4-yl)-N-[(1R)-1-(5-methoxypyridin-2-yl)ethyl]acetamide 5-methoxy-2-methylpyridine To a suspension of potassium hydroxide (113 g, 2 mol) in DMSO (800 ml) was added 53.9 g, (0.49 mmol) 5-hydroxy-2-methylpyridine and the mixture stirred for 1 h. To this was added CH$_3$I (34 ml, 0.55 mol) and the reaction mixture was stirred for one hour, then poured into water (2400 ml) and extracted with ether (1000 ml×5). The combined organic layers were washed with water and brine, dried over Na$_2$SO$_4$ and concentrated in vacuo to provide 5-methoxy-2-methylpyridine as a yellow oil. $^1$H NMR: (400 MHz, CDCl$_3$) δ 8.19 (d, J=2.8 Hz, 1H), 7.14 (dd, J=8.8, 3.8 Hz, 1H), 7.08 (d, J=8.4 Hz, 1H), 3.83 (s, 3H), 2.65 (s, 3H). (5-methoxypyridin-2-yl)methanol: To a 0° C. solution of 10 g (72 mmol) 5-methoxy-2-methylpyridine in CHCl$_3$ (50 ml) was slowly added 20 g (93.9 mmol) mCPBA and the mixture was stirred at room temperature for 16 h. The mixture was neutralized with excess sat. NaHSO$_3$ solution. The aqueous layer was extracted with CHCl$_3$ three times. The combined organic layers were dried over MgSO$_4$ and evaporated to give 7 g of 5-methoxy-2-methyl-1-oxopyridine as a yellow solid. This was added slowly to hot (1000° C.)acetic anhydride (25 mL, 26 mmol) over 30 minutes and the mixture heated an additional 30 minutes, whereupon ethanol was added until the excess acetic anhydride was consumed. The mixture was cooled, concentrated, and neutralized with aqueous KHCO$_3$ solution. The aqueous layer was extracted with CH$_2$Cl$_2$, dried over MgSO$_4$, and concentrated in vacuo to afford 7.5 of (5-methoxypyridin-2-yl)methyl acetate as a dark oil. To this oil was added 25 mL of concentrated HCl and the mixture heated to reflux for 1 hour then concentrated in vacuo. The residue was treated with aqueous KHCO3 and extracted with CH$_2$Cl$_2$. The CH$_2$Cl$_2$ extract was dried over MgSO4, filtered, and concentrated in vacuo to give (5-methoxypyridin-2-yl)

methanol as an oil. ¹H NMR (400 MHz, DMSO-d₆) δ 7.65 (m, 2H), 6.45 (m, 1H), 4.75 (s, 2H), 3.25 (s, 3H).

5-methoxypyridine-2-carbaldehyde:

To a solution of 5.7 g (41 mmol) (5-methoxypyridin-2-yl)methanol in 100 mL CHCl₃ was added 15 g MnO₂ and the mixture heated to reflux for 2 hours, filtered, and washed with boiling CHCl₃. The filtrate was washed with brine, dried over MgSO₄, and concentrated in vacuo to afford 5-methoxypyridine-2-carbaldehyde as a white solid. ¹H NMR (400 MHz, CDCl₃) δ 9.99 (s, 1H), 8.44 (d, J=2.4 Hz, 1H), 7.97 (d, J=8.4 Hz, 1H), 7.3 (dd, J=8.4, 2.4 Hz, 1H), 3.95 (s, 2H).

(R)—N-[(1E)-(5-methoxypyridin-2-yl)methylene]-2-methylpropane-2-sulfinamide

To a solution of (R) t-butanesulfinamide (292 mg, 2.4 mmol) in CH₂Cl₂ (10 ml) was added anhydrous CuSO₄ (770 mg, 4.8 mmol) and 5-methoxypyridine-2-carbaldehyde (330 mg, 2.4 mmol). The mixture was stirred at room temperature for 16 h. The reaction mixture was filtered and the CuSO₄ cake was washed well with CH₂Cl₂ and concentrated in vacuo. Purification by flash chromatography afforded (R)—N-[(1E)-(5-methoxypyridin-2-yl)methylene]-2-methylpropane-2-sulfinamide (69.9%) as white solid. (300 MHz, CDCl₃) δ 8.64 (s, 1H), 8.42 (d, J=3 Hz, 1H), 7.97 (d, J=8.8 Hz, 1H), 7.27 (dd, J=8.8 Hz, 1H), 3.93 (s, 3H), 1.27 (s, 9H).

(R)[(1R)-1-(5-methoxypyridin-2-yl)ethyl]-2-methylpropane-2-sulfinamide

To a solution of (R)—N-[(1E)-(5-methoxypyridin-2-yl)methylene]-2-methylpropane-2-sulfinamide (1.2 g, 5 mmol) in THF (100 ml) at −78° C. was added a 3M solution of MeMgCl in THF (7.5 ml). After 45 min, the reaction was quenched by the addition of saturated aqueous solution of NH₄Cl. (100 ml) and extracted with EtOAc. The combined organic layers were washed with brine, dried over MgSO₄, filtered, and concentrated to afford (R)[(1R)-1-(5-methoxypyridin-2-yl)ethyl]-2-methylpropane-2-sulfinamide. (400 MHz, CDCl₃) δ 8.22 (d, J=2.4 Hz, 1H), 7.22-7.17 (m, 2H), 4.55 (m, 1H), 3.83 (s, 3H), 1.46 (d, J=6.0 Hz, 3H), 1.26 (s, 9H).

(1R)-1-(5-methoxypyridin-2-yl)ethanamine

To a solution of HCl in MeOH (10 ml) was added 1 g (3.7 mmol) (R)[(1R)-1-(5-methoxypyridin-2-yl)ethyl]-2-methylpropane-2-sulfinamide and the mixture was stirred at room temperature for 30 min. Diethyl ether was added dropwise and the resulting precipitate was filtered and recrystallized from EtOH and ether to afford (1R)-1-(5-methoxypyridin-2-yl)ethanamine as a white solid. ¹HNMR (400 MHz, DMSO-d₆) δ 8.50 (bs, 2H), 8.30 (d, J=1.6 Hz, 1H), 7.49-7.54 (m, 2H), 4.45 (dd, J=8.0, 2.0 Hz, 1H), 3.93 (s, 3H), 1.45 (d, J=6.8 Hz, 3H).

2-(1,1'-biphenyl-4-yl)-N-[(1R)-1-(5-methoxypyridin-2-yl)ethyl]acetamide

To a mixture of 4-biphenylacetic acid (2.00 g, 9.42 mmol), (1R)-1-(5-methoxypyridin-2-yl)ethanamine hydrochloride (1.96 g, 10.36 mmol), 1-hydroxy-7-azabenzotriazole (1.70 g, 12.49 mmol) and diisopropyl-ethyl amine (5.20 ml, 31.46 mmol) in DMF (55 ml) was added 1-(3-dimethylaminopropyl)-3-ethylcarbodiimide hydrochloride (2.40 g, 12.52 mmol) at room temperature. The reaction was stirred for 18 hours and then washed with saturated sodium bicarbonate solution and brine. Organics were extracted with EtOAc, dried over Na₂SO₄, filtered and concentrated in vacuo. Purification by normal phase chromatography (0-80% EtOAc/Hex) afforded 2-(1,1'-biphenyl-4-yl)-N-[(1R)-1-(5-methoxypyridin-2-yl)ethyl]acetamide as a yellow solid. 1H NMR (CDCl₃, 400 MHz) δ 8.16 (s, 1H); 7.58 (m, 4H); 7.44 (m, 2H); 7.34 (m, 3H); 7.14 (m, 2H); 6.78 (d, J=6.80 Hz, 1H); 5.10 (m, 1H); 3.83 (s, 3H); 3.63 (s, 2H); 1.41 (d, J=6.80 Hz, 3H). MS (Electrospray): m/z 347.1 (M+H).

EXAMPLE 8

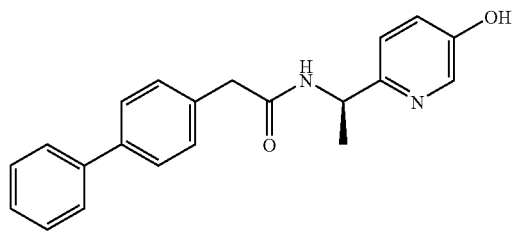

2-(1,1'-biphenyl-4-yl)-N-[(1R)-1-(5-hydroxypyridin-2-yl)ethyl]acetamide

To a mixture of 2-(1,1'-biphenyl-4-yl)-N-[(1R)-1-(5-methoxypyridin-2-yl)ethyl]acetamide (200 mg, 0.58 mmol) in DMSO (4.0 ml) was added sodium cyanide (141 mg, 2.89 mmol) and heated to 180° C. for one hour. An additional amount of sodium cyanide (207 mg, 4.22 mmol) was added and the mixture was further heated for another hour until no significant increase in desired product was observed by LC/MS. After cooling reaction to room temperature, the reaction was taken to neutral pH with the careful addition of 1.0 N HCl solution. Organics were extracted with EtOAc, dried over Na2SO4, filtered and concentrated in vacuo to give an oil. Normal phase chromatography (0-100% EtOAc/Hex) afforded 2-(1,1'-biphenyl-4-yl)-N-[(1R)-1-(5-hydroxypyridin-2-yl)ethyl]acetamide as an oil. ¹H NMR (CDCl₃, 400 MHz) δ 9.55 (brs, 1H); 8.07 (m, 1H); 7.50 (m, 4H); 7.41 (m, 2H); 7.28 (m, 3H); 7.00 (m, 2H); 6.82 (d, J=7.20 Hz, 1H); 5.03 (m, 1H); 3.57 (s, 2H); 1.37 (d, J=6.40 Hz, 3H); MS (Electrospray): m/z 333.1 (M⁺H).

EXAMPLE 9

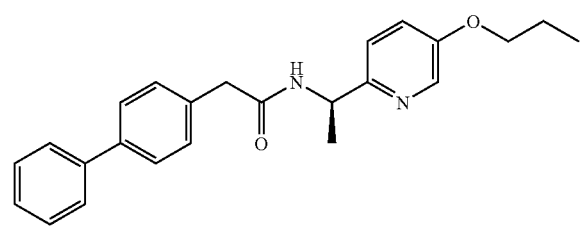

2-(1,1'-biphenyl-4-yl)-N-[(1R)-1-(5-propoxypyridin-2-yl)ethyl]acetamide

To a mixture of 2-(1,1'-biphenyl-4-yl)-N-[(1R)-1-(5-hydroxypyridin-2-yl)ethyl]acetamide (30 mg, 0.09 mmol) (Example 8), 1-bromopropane (0.02 ml, 0.22 mmol) in DMF (1.2 ml) was added potassium carbonate (37 mg, 0.27 mmol). The reaction was stirred at 40° C. for 18 hours and then filtered through a cotton plug to remove any precipitates, washing with DMSO (2 ml). The collected filtrate was purified using reverse phase prep HPLC chromatography to afford the mono-trifluoroacetate salt of 2-(1,1'-biphenyl-4-yl)-N-[(1R)-1-(5-propoxypyridin-2-yl)ethyl]acetamide as an oil. $^1$H NMR (CD$_3$OD, 400 MHz) δ 8.34 (s, 1H); 7.97 (dd, J=2.80 and 9.20 Hz, 1H); 7.74 (d, J=8.80 Hz, 1H); 7.56 (m, 4H); 7.40 (m, 2H); 7.33 (m, 3H); 5.07 (m, 1H); 4.11 (t, J=6.40 Hz, 2H); 3.61 (s, 2H); 1.84 (m, 2H); 1.57 (d, J=7.20 Hz, 3H); 1.05 (t, J=7.60 Hz, 3H). HRMS (ES) exact mass calcd for C$_{24}$H$_{26}$N$_2$O$_2$: 375.2067, Found: 375.2078.

EXAMPLE 10

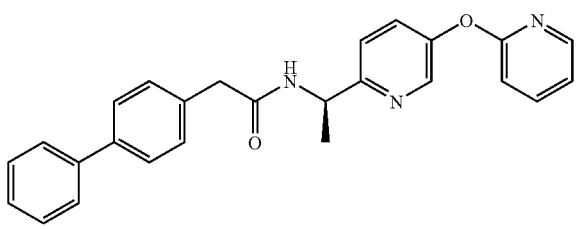

2-(1,1'-biphenyl-4-yl)-N-{(1R)-1-[5-(pyridine-2-yloxy)pyridine-2-yl]ethyl}acetamide To a mixture of 2-(1,1'-biphenyl-4-yl)-N-[(1R)-1-(5-hydroxypyridin-2-yl)ethyl]acetamide (40 mg, 0.12 mmol) and 2-fluoropyridine (31 µL, 0.36 mmol) in DMF (3.0 ml) was added cesium carbonate (137 mg, 0.42 mmol). The reaction was heated to 130° C. for 30 minutes. An additional amount of 2-fluoropyridine (31 µL, 0.36 mmol) was added and the mixture heated for one hour at 130° C. The reaction was cooled, washed with brine and extracted with EtOAc. The organic layer was dried over Na$_2$SO$_4$, filtered and concentrated in vacuo to give an oil. Reverse phase prep HPLC chromatography afforded the mono-trifluoroacetate salt of 2-(1,1'-biphenyl-4-yl)-N-{(1R)-1-[5-(pyridine-2-yloxy)pyridine-2-yl]ethyl}acetamide as a yellow oil. $^1$H NMR (CD$_3$OD, 400 MHz) δ 8.61 (s, 1H, 8.11 (dd, J=1.60 and 4.80 Hz, 1H); 8.01 (dd, J=2.80 and 8.80 Hz, 1H); 7.89 (m, 1H); 7.71 (d, J=8.80 Hz, 1H); 7.56 (m, 4H); 7.38 (m, 5H); 7.18 (m, 1H); 7.12 (d, J=8.40 Hz, 1H); 5.12 (m, 1H), 3.63 (s, 2H); 1.58 (d, J=7.20 Hz, 3H). HRMS (ES) exact mass calcd for C$_{26}$H$_{23}$N$_3$O$_2$: 410.1863, Found: 410.1873

EXAMPLE 11

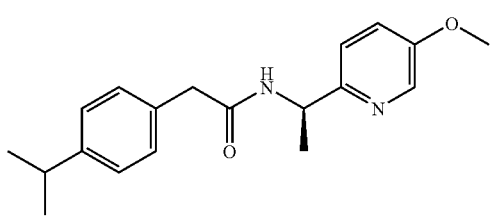

2-(4-isopropylphenyl)-N-[(1R)-1-(5-methoxypyridin-2-yl)ethyl]acetamide

To a suspension of 4-isopropylphenylacetic acid (2.5 g, 14.0 mmol), (1R)-1-(5-methoxypyridin-2-yl)ethylamine hydrochloride (3.2 g, 16.8 mmol), EDC (3.24 g, 16.9 mmol), and 1-hydroxy-7-azabenzotriazole (2.3 g, 16.8 mmol) in DMF (60 mL) was added N,N-diisopropylethylamine (5.2 mL, 29.6 mmol). The reaction mixture was stirred at room temperature for 2.5 h and then concentrated to 20 mL and diluted with CH$_2$Cl$_2$ (100 mL). The solution was washed with water (100 mL) and the aqueous layer was extracted with CH$_2$Cl$_2$ (2×75 mL). The combined organic layer was washed with water (100 mL), dried over MgSO$_4$, concentrated and purified by normal phase chromatography (10-100% EtOAc/Hexanes) to give of 2-(4-isopropylphenyl)-N-[(1R)-1-(5-methoxypyridin-2-yl)ethyl]acetamide as a pale yellow solid. $^1$H NMR (CDCl$_3$, 400 MHz) δ 8.14 (d, J=2.56 Hz, 1H), 7.20 (m, 4H), 7.13 (m, 2H), 6.69 (d, J=6.78 Hz, 1H), 5.08 (quint., J=6.96 Hz, 1H), 3.84 (s, 3H), 3.55 (s, 2H), 2.90 (sept., J=6.96 Hz, 1H), 1.39 (d, J=6.77 Hz, 3H), 1.25 (d, J=6.96 Hz, 6H); MS (Electrospray): m/z 313.4 (M+H).

EXAMPLE 12

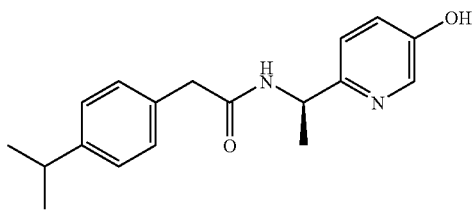

N-[(1R)-1-(5-hydroxypyridine-2-yl)ethyl]-2-(4-isopropylphenyl)acetamide 2-(4-Isopropylphenyl)-N-[(1R)-1-(5-methoxypyridin-2-yl)ethyl]acetamide (3.8 g, 12.2 mmol) (Example 11) was dissolved in DMSO (20 mL) and transferred to a sealed tube. To this solution was added NaCN (3.6 g, 73.0 mmol) and the mixture was stirred at 175° C. for 16 h. The mixture was cooled to room temperature and diluted with CH$_2$Cl$_2$ (200 mL) and water (100 mL). The pH of the aqueous layer was brought to neutral by the addition of 2N HCl and the layers were separated. The organic layer was washed with water (100 mL) and brine (100 mL), concentrated, and purified by normal phase chromatography (2-10% MeOH/CH$_2$Cl$_2$) to give N-[(1R)-1-(5-hydroxypyridine-2-yl)ethyl]-2-(4-isopropylphenyl)acetamide as a tan solid. $^1$H NMR (CDCl$_3$, 400 MHz) δ 8.06 (t, J=1.65 Hz, 1H), 7.17 (m, 4H), 7.02 (m, 2H), 6.67 (d, J=7.50 Hz, 1H), 5.03 (quint., J=6.96 Hz, 1H), 3.53 (d, J=2.20 Hz, 2H), 2.88 (sept., J=6.69 Hz, 1H), 1.38 (d, J=6.77 Hz, 3H), 1.23 (d, J=6.95 Hz, 6H); MS (Electrospray): m/z 299.3 (M+H).

EXAMPLE 13

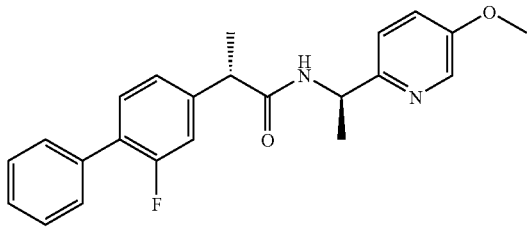

(2S)-2-(2-fluoro-1,1'-biphenyl-4-yl)-N-[(1R)-1-(5-methoxypyridin-2-yl)ethyl]propanamide To a solution of 0.70 g (2.87 mmol) (S)-(+)-2-fluoro-alpha-methyl-4-biphenylacetic acid in 6.00 ml DMF was added 0.60 g (3.15 mmol) (1R)-1-(5-methoxypyridin-2-yl)ethanaminium chloride, 0.51 g (3.73 mmol) HOAT, 0.71 g (3.73 mmol) EDC, and 1.50 mL (8.60 mmol) DIEA. After 2.00 h at room temperature, the reaction mixture was diluted with $CH_2Cl_2$, washed three times with water, and washed with brine. The organic layer was dried over $NaSO_4$, filtered and concentrated in vacuo. Purification by flash chromatography (1×14 cm silica gel, linear gradient 30-65% EtOAc:hexane) afforded (2S)-2-(2-fluoro-1,1'-biphenyl-4-yl)-N-[(1R)-1-(5-methoxypyridin-2-yl)ethyl]propanamide. $^1$H NMR (CDCl$_3$, 400 MHz) δ 8.19 (m, 1H); 7.56-7.54 (m, 2H); 7.46-7.34 (m, 4H); 7.20-7.14 (m, 4H); 6.78 (br d, 1H, J=7.33 Hz); 5.09 (m, 1H); 3.85 (s, 1H); 3.60 (q, 1H, J=7.15 Hz, 14.29 Hz); 1.53 (d, 3H, J=7.14); 1.37 (d, 3H, J=6.77 Hz). HRMS (ES) exact mass calcd for $C_{23}H_{23}FN_2O_2$: 379.1817, Found: 379.1817.

EXAMPLE 14

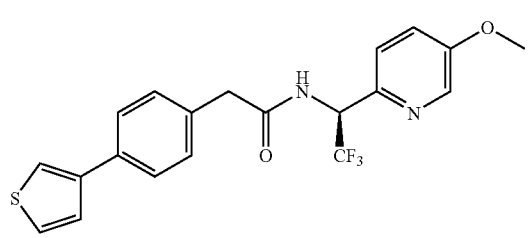

(R)[(1S)-1-(5-methoxypyridin-2-yl)-2,2,2-trifluoroethyl]-2-methylpropane-2-sulfinamide TMSCF$_3$ in THF (12 ml, 24 mmol) was added to a mixture of (R)—N-[(1E)-(5-methoxypyridin-2-yl)methylene]-2-methylpropane-2-sulfinamide (2.4 g, 10 mmol) and TBAT (10.8 g, 22 mmol) in THF (100 ml) at −55° C. The reaction mixture was stirred at −55° C. for 10 min and raised to −30° C. for 2 h. Saturated aqueous NH$_4$Cl was added and the reaction mixture was extracted with EtOAc. The combined organic layer was washed with brine, dried over Na$_2$SO$_4$, purified by silica gel chromatography to afford (R)[(1R)-1-(5-methoxypyridin-2-yl)-2,2,2-trifluoroethyl]-2-methylpropane-2-sulfinamide as oil. $^1$H NMR (400 MHz, CDCl$_3$) δ 8.28 (d, J=2.8 Hz, 1H), 7.32 (d, J=8.4 Hz, 1H), 7.22 (dd, J=8.4, 2.8 Hz), 5.68 (d, J=6.4 Hz, 1H), 3.87 (s, 3H), 1.31 (s, 9H).

2,2,2-trifluoro-1-(5-methoxypyridin-2-yl)ethanamine (R)[(1R)-1-(5-methoxypyridin-2-yl)-2,2,2-trifluoroethyl]-2-methylpropane-2-sulfinamide (0.9 g, 2.9 mmol) was added to HCl in MeOH (20 ml) and stirred at room temperature for 30 min, then the solvent was evaporated. Water and ether was added to the residue, then separated the organic layer. The remained aqueous layer was evaporated to give 0.67 g of 2,2,2-trifluoro-1-(5-methoxypyridin-2-yl)ethanamine hydrochloride. $^1$HNMR: (400 MHz, DMSO-d$_6$) δ 9.59 (br, 2H), 8.37 (s, 1H), 7.64 (d, J=8.8 Hz, 1H), 7.55 (d, J=8.8 Hz, 1H), 5.63 (m, 1H), 3.86 (s, 3H).

2-[4-(3-thienyl)phenyl]-N-[(1S)-2,2,2-trifluoro-1-(5-methoxypyridin-2-yl)ethyl]acetamide To a solution of 0.04 g (0.18 mmol) [4-(3-thienyl)phenyl]acetic acid in 0.75 mL DMF was added 0.06 g (0.2 mmol) 2,2,2-trifluoro-1-(5-methoxypyridin-2-yl)ethanamine hydrochloride, 0-1 mL (0.6 mmol) triethylamine, 0.03 g (0.2 mmol) HOAt, and 0.05 g (0.2 mmol) EDC and the mixture stirred for 1 hour at room temperature. Purification (no workup) by preparative reverse phase HPLC (linear gradient 5 to 95% CH$_3$CN/H$_2$O over 30 min, 0.05% added TFA, C18 SunFire 19×150 mm) afforded 2-[4-(3-thienyl)phenyl]-N-[(1S)-2,2,2-trifluoro-1-(5-methoxypyridin-2-yl)ethyl]acetamide high resolution mass spec calc for $C_{20}H_{17}F_3N_2O_2S$ 407.1036, found 407.1043. 1H NMR (400 MHz, CDCl$_3$) δ 8.20 (d, 1H, J=2.84 Hz); 7.58 (d, 2H, J=8.33 Hz); 7.46 (t, 1H, J=2.10); 7.39 (d, 2H, J=2.10 Hz); 7.30 (m, 3H); 7.22 (dd, 1H, J=2.93 and 8.60 Hz); 5.73 (dq, 1H, J=7.14 and 7.14 Hz); 3.86 (s, 3); 3.70 (s, 2H)

EXAMPLE 15

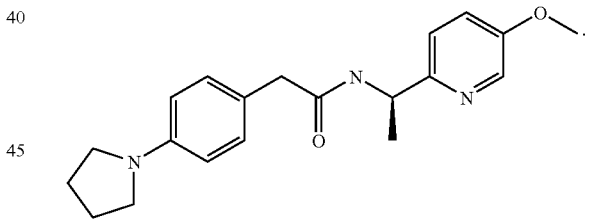

N-[(1R)-1-(5-methoxypyridin-2-yl)ethyl]-2-(4-pyrrolidin-1-ylphenyl)acetamide

To a suspension of (4-pyrrolidin-1-ylphenyl)acetic acid (U.S. Pat. No. 3,641,040) (0.50 g, 2.4 mmol), (1R)-1-(5-methoxypyridin-2-yl)ethylamine hydrochloride (0.57 g, 3.0 mmol), and HATU (1.2 g, 3.1 mmol) in DMF (3 mL) was added N,N-diisopropylethylamine (1.7 mL, 9.7 mmol) and the mixture was stirred at room temperature for 16 h. The solution was concentrated and the crude residue was partitioned between water and EtOAc. The organic layer was washed with brine and water, dried over MgSO$_4$, and purified by normal phase chromatography (10-100% EtOAc/hexanes) to give N-[(1R)-1-(5-methoxypyridin-2-yl)ethyl]-2-(4-pyrrolidin-1-ylphenyl)acetamide as a tan solid. $^1$H NMR (400 MHz, CDCl$_3$) δ 8.16 (m, 1H), 7.11 (m, 4H), 6.54 (m, 3H), 5.09 (m, 1H), 3.83 (s, 3H), 3.48 (d, J=3.2 Hz, 2H), 3.28 (t, J=6.4 Hz, 4H), 2.01 (m, 4H), 1.36 (d, J=6.4 Hz, 3H); MS (Electrospray): m/z 340.4 (M+H)

EXAMPLE 16

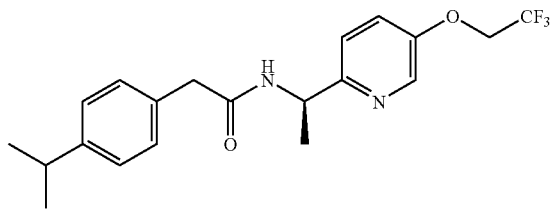

2-(4-isopropylphenyl)-N-[(1R)-1-(5-(2,2,2-trifluoroethoxy)pyridin-2-yl)ethyl]acetamide To a suspension of 2-methyl-5-hydroxypyridine (10.5 g, 96.0 mmol) and cesium carbonate (36.1 g, 111 mmol) in DMF (100 mL) was added 2,2,2-trifluoroethyl-trifluoromethanesulfonate (25.7 g, 111 mmol) dropwise over 30 min. The reaction was exothermic and the mixture, which turned to a dark brown color, was stirred for an additional 1 h. The mixture was diluted with water (200 mL) and extracted with EtOAc (200 mL). The organic layer was washed with water (100 mL) then dried over MgSO$_4$, filtered, and concentrated to give 2-methyl-5-(2,2,2-trifluoroethoxy)pyridine as a dark oil that was used in the next step without further purification; MS (Electrospray): m/z 192.1 (M+H). To a solution of 2-methyl-5-(2,2,2-trifluoroethoxy)pyridine (30.0 g, 157 mmol) in chloroform (350 mL) was added mCPBA (50.0 g, 212 mmol, 73% purity) and the mixture was stirred at room temperature. During addition of mCPBA, the reaction turned from a deep brown color to pale red and some heat was evolved so the reaction flask with immersed in a room temperature water bath. After stirring for 1.5 h, the reaction was washed with a saturated sodium bicarbonate solution (500 mL) and the organic layer was dried over MgSO4, filtered, and concentrated to give 2-methyl-5-(2,2,2-trifluoroethoxy) pyridine-N-oxide as a yellow solid that was used directly in the next step without further purification; MS (Electrospray): m/z 208.1 (M+H). A solution of 2-methyl-5-(2,2,2-trifluoroethoxy)pyridine-N-oxide (32.5 g, 157 mmol) in acetic anhydride (100 mL) was heated at 100° C. for 1 h. LC/MS analysis of the reaction mixture indicated that all starting material was consumed. The mixture was concentrated to ~⅓ volume and diluted with methanol (150 mL). Potassium carbonate (130 g, 941 mmol) was then added very slowly to the vigorously stirred mixture (Caution: extensive gas evolution). LC/MS analysis after 30 min indicated the presence of only the desired alcohol. Water (200 mL) was added to the mixture and the remaining methanol was removed on the rotary evaporator. The remaining aqueous solution was extracted with EtOAc (2×200 mL) and the organic layer was dried over MgSO$_4$, filtered and concentrated. The crude residue was purified by silica gel chromatography (5-95% EtOAc/Hexanes) to give (5-(2,2,2-trifluoroethoxy)pyridin-2-yl)methanol (21 g, 64%) as a yellowish oil; $^1$H NMR (400 MHz, CDCl$_3$) δ 8.31 (d, J=2.8 Hz, 1H), 7.24-7.32 (m, 2H), 4.74 (s, 2H), 4.41 (q, J=8.0 Hz, 2H), 3.50 (br s, 1H); MS (Electrospray): 7/z 208.1 (M+H). To a solution of (5-(2,2,2-trifluoroethoxy)pyridin-2-yl)methanol (21.0 g, 101 mmol) in dichloromethane (200 mL) was added a 15% aqueous KBr solution (20 mL) followed by a saturated bicarbonate solution (85 mL). The biphasic mixture was cooled in an ice bath and TEMPO (792 mg, 5.07 mmol) was added. After stirring for 10 min. commercial bleach (100 mL, ~6.15% NaOCl, 115 mmol)) was added dropwise over 30 min. LC/MS of the organic layer indicated mostly desired aldehyde but some remaining alcohol. An additional 15 mL of bleach was added dropwise to bring the reaction to completion. The mixture was poured into a separatory funnel and the organic layer was separated directly into a flask for the next reaction; MS (Electrospray): m/z 206.1 (M+H). To a dichloromethane solution of 5-(2,2,2-trifluoroethoxy)pyridin-2-carboxaldehyde (19 g, 93 mmol) was added CuSO$_4$ (37.1 g, 233 mmol) followed by (R)-2-methyl-2-propanesulfinamide (11.3 g, 93 mmol) and the mixture was stirred for 14 h at room temperature. The reaction mixture was filtered through Celite and concentrated. The crude material was purified by silica gel chromatography (0-75% EtOAc/Hexanes) to give (R)-2-methyl-N-[(5-(2,2,2-trifluoroethoxy)pyridin-2-yl)methylene]propane-2-sulfinamide (19 g, 66%) as a flaky solid; $^1$H NMR (400 MHz, CDCl$_3$) δ 8.66 (s, 1H), 8.47 (d, J=2.8 Hz, 1H), 8.03 (d, J=8.8 Hz, 1H), 7.35 (dd, J=2.8 Hz and 8.8 Hz, 1H), 4.48 (q, J=8.0 Hz, 2H), 1.28 (s, 9H); MS (Electrospray): m/z 309.2 (M+H). To a -78° C. cooled solution of (R)-2-methyl-N-[(5-(2,2,2-trifluoroethoxy)pyridin-2-yl)methylene]propane-2-sulfinamide (12.4 g, 40.2 mmol) in dichloromethane (200 mL) was added methylmagnesium bromide (1.4M, 60 mL, 84 mmol). The Grignard reagent was added at a rate such that the internal reaction temperature was never warmer than -75° C. After complete addition the mixture was stirred for 1 h then warmed to room temperature and quenched with a saturated ammonium chloride solution. The organic layer was separated and the aqueous layer was extracted once with EtOAc. The combined organic layer was dried over MgSO$_4$, filtered, and concentrated to give a crude oil. $^1$H-NMR indicated a ~16:1 diastereomeric ratio of products that were separated by silica gel chromatography (50-100% EtOAc/hexanes) to give (R)-2-methyl-N-[(1R)-(5-(2,2,2-trifluoroethoxy)pyridin-2-yl)ethyl]propane-2-sulfinamide (12 g, 92%) as a pale yellow oil; $^1$H NMR (400 MHz, CDCl$_3$) δ 8.29 (d, J=2.8 Hz, 1H), 7.23-7.29 (m, 2H), 4.55-4.59 (m, 2H), 4.39 (q, J=8.0 Hz, 2H), 1.49 (d, J=6.4 Hz, 3H), 1.25 (s, 9H); MS (Electrospray): m/z 325.3 (M+H). To a solution of (R)-2-methyl-N-[(1R)-(5-(2,2,2-trifluoroethoxy)pyridin-2-yl)ethyl]propane-2-sulfinamide (11.8 g, 36.4 mmol) in MeOH (40 mL) was added HCl in ether (2M, 50 mL, 100 mmol). After stirring for 15 min at room temperature, the mixture was concentrated to give a yellow oil. The oil was then swished with ether to generate a white solid that was filtered and dried under high vacuum to give (R)-1-[5-(2,2,2-trifluoroethoxy)pyridin-2-yl]ethylamine as the bis-hydrochloride salt; MS (Electrospray): m/z 221.1 (M+H). To a suspension of (R)-1-[5-(2,2,2-trifluoroethoxy)pyridin-2-yl]ethylamine bis-HCl (9.0 g, 31 mmol), 4-isopropylphenylacetic acid (6.0 g, 34 mmol), EDC (7.0 g, 37 mmol), and 1-hydroxy-7-azabenzotriazole (5.0 g, 37 mmol) in DMF (50 mL) was added diisopropylethylamine (21.5 mL, 123 mmol). After stirring for 2 h at room temperature, the mixture was slowly added to vigorously stirred water (500 mL) to generate a white precipitate that was filtered and dried. The resulting solid was recrystallized from hexane (~3 g solid/200 mL hexane) to give 2-(4-isopropylphenyl)-N-[(1R)-1-(5-(2,2,2-trifluoroethoxy)pyridin-2-yl)ethyl]acetamide (9.7 g, 83%) as a white solid; $^1$H NMR (400 MHz, CDCl$_3$) δ 8.20 (d, J=2.8 Hz, 1H), 7.16-7.22 (m, 6H), 6.62 (d, J=7.2 Hz, 1H), 5.07-5.14 (m, 1H), 4.37 (q, J=8.0 Hz, 2H), 3.55 (s, 2H), 2.87-2.93 (m, 1H), 1.39 (d, J=6.8 Hz, 3H), 1.25 (d, J=7.2 Hz, 6H); MS (Electrospray): m/z 381.3 (M+H).

EXAMPLE 17

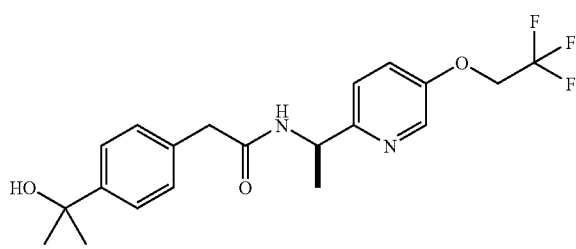

2-[4-(1-hydroxy-1-methylethyl)phenyl]-N-[(1R)-1-(5-(2,2,2-trifluoroethoxy)pyridin-2-yl)ethyl]acetamide To a suspension of [4-(1-hydroxy-1methylethyl)phenyl] acetic acid (266 mg, 1.37 mmol), (1R)-1-(5-(2,2,2-trifluoroethoxy)pyridin-2-yl)ethylamine bis-hydrochloride (400 mg, 1.37 mmol), EDC (315 mg, 1.64 mmol), and 1-hydroxy-7-azabenzotriazole (224 mg, 1.64 mmol) in DMF (20 mL) was added N,N-diisopropylethylamine (741 uL, 4.25 mmol). The reaction mixture was stirred at room temperature overnight, then concentrated to ~5 mL and diluted with CH$_2$Cl$_2$ (50 mL). The solution was washed with water (50 mL) and the aqueous layer was extracted with CH$_2$Cl$_2$ (2×30 mL). The combined organic layer was washed with water (50 mL), dried over MgSO$_4$, concentrated and purified by normal phase chromatography (15-100% EtOAc/Hexanes) to give 270 mg (50%) of 2-[4-(1-hydroxy-1-methylethyl)phenyl]-N-{(1R)-1-[5-(2,2,2-trifluoroethoxy)pyridin-2-yl]ethyl}acetamide as a white solid. $^1$H NMR (CDCl$_3$, 400 MHz) δ 8.20 (d, J=2.75 Hz, 1H), 7.45 (m, 2H), 7.22 (m, 4H), 6.68 (d, J=7.33 Hz, 1H), 5.11 (quint. J=6.96 Hz, 1H), 4.38 (q, J=8.00 Hz, 2H), 3.57 (s, 2H), 1.59 (s, 6H), 1.40 (d, J=6.77 Hz, 3H); MS (Electrospray): m/z 397.3 (M+H).

EXAMPLE 18

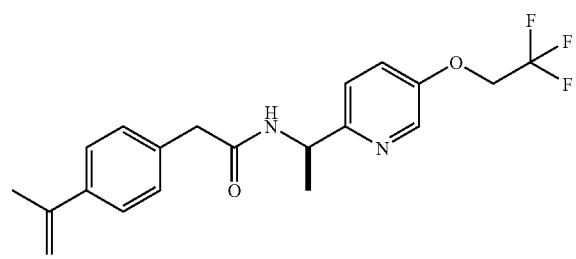

2-(4-isopropenylphenyl)-N-[(1R)-1-(5-(2,2,2-trifluoroethoxy)pyridin-2-yl)ethyl]acetamide A mixture of 2-[4-(1-hydroxy-1-methylethyl)phenyl]-N-{(1R)-1-[5-(2,2,2-trifluoroethoxy)pyridin-2-yl]ethyl}acetamide (400 mg, 1.01 mmol) and p-toluenesulfonic acid monohydrate (38.4 mg, 0.202 mmol) in toluene (4.5 mL) was heated at 100° C. in a sealed tube for 6 h. The mixture was cooled to room temperature, diluted with CH$_2$Cl$_2$ (40 mL) and washed with water (2×50 mL). The organic layer was dried over MgSO$_4$, concentrated and purified by normal phase chromatography (20-100% EtOAc/Hexanes) to give 316 mg (83%) of 2-(4-isopropenylphenyl)-N-{(1R)-1-[5-(2,2,2-trifluoroethoxy)pyridin-2-yl]ethyl}acetamide as a white solid. $^1$H NMR (CDCl$_3$, 400 MHz) δ 8.21 (d, J=2.35 Hz, 1H), 7.45 (m, 2H), 7.20 (m, 4H), 6.64 (d, J=7.32 Hz, 1H), 5.38 (s, 1H), 5.11 (m, 1H), 5.09 (s, 1H), 4.37 (q, J=7.94 Hz, 2H), 3.58 (s, 2H), 2.15 (s, 3H), 1-39 (d, J=6.77 Hz, 3H); MS (Electrospray): m/z 379.5 (M+H).

EXAMPLE 19

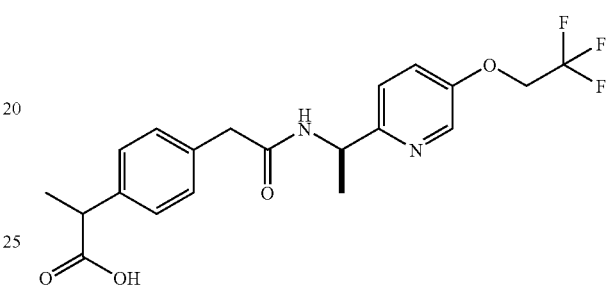

2-{4-[2-oxo-2-(((1R)-1-[5-(2,2,2-trifluoroethoxy)pyridine-2-yl]ethyl)amino)ethyl]phenyl}-propionic acid A suspension of 2-(4-bromomethyl)phenylpropionic acid (2.0 g, 8.2 mmol) and potassium cyanide (1.6 g, 24.7 mmol) in EtOH (10 mL) and water (2 mL) was heated at 80° C. in a sealed tube for 1 h. The mixture was cooled to room temperature, diluted with water (10 mL) and the EtOH was removed under reduced pressure. The remaining aqueous mixture was extracted once with EtOAc then acidified carefully with 2N HCl until pH~3 is reached. The aqueous layer was extracted with EtOAc and the combined organic layer was dried over MgSO$_4$, filtered, and concentrated to give 2-[4-(cyanomethyl)phenyl]propionic acid in ~90% purity. This material was used directly in the next step. A mixture of 2-[4-(cyanomethyl)phenyl]propionic acid (1.4 g, 7.4 mmol) in MeOH (8 mL) and aqueous NaOH(5N, 8 mL, 40 mmol) was heated at 85° C. in a sealed tube for 1.5 h. The mixture was cooled to room temperature, the MeOH was removed under reduced pressure, and the remaining aqueous was extracted with once ether. The aqueous layer was acidified with 2N HCl until pH~2 to generate a precipitate that was filtered and dried under vacuum to afford 2-[4-(carboxymethyl)phenyl]propionic acid (1.1 g, 71%) as an off-white solid; $^1$H NMR (400 MHz, DMSO-d$_6$) δ 12.27 (br s, 1H), 7.15-7.22 (m, 4H), 3.61 (q, J=6.8 Hz, 1H), 3.50 (s, 2H), 1.30 (d, J=7.2 Hz, 3H); MS (Electrospray): m/z 163.1 (M-CO$_2$H). To a suspension of (R)-1-[5-(2,2,2-trifluoroethoxy)pyridine-2-yl]ethanamine bis-HCl (0.39 g, 1.3 mmol), 2-[4-(carboxymethyl)phenyl] propionic acid (0.35 g, 1.7 mmol), EDC (0.35 g, 1.8 mmol), and 1-hydroxy-7-azabenzotriazole (0.25 g, 1.8 mmol) in DMF (5 mL) was added diisopropylethylamine (1.2 mL, 6.7 mmol). After stirring for 2 h at room temperature, the mixture was diluted with water (20 mL) and extracted with dichloromethane. The organic layer was dried over MgSO$_4$, filtered, and concentrated to give a crude oil that was purified by preparative reversed-phase HPLC to give 2-{4-[2-oxo-2-

(((1R)-1-[5-(2,2,2-trifluoroethoxy)-pyridine-2-yl]ethyl)amino)ethyl]phenyl}propionic acid mono-TFA salt as a foam; $^1$H NMR (400 MHz, DMSO-$d_6$) δ 8.50 (d, J=7.6 Hz, 1H), 8.33 (d, J=2.8 Hz, 1H), 7.49 (dd, J=2.8 and 8.8 Hz, 1H), 7.28 (d, J=8.8 Hz, 1H), 7.19 (s, 4H), 4.88-4.93 (m, 1H), 4.85 (q, J=8.8 Hz, 2H), 3.62 (q, J=7.2 Hz, 1H), 3.44 (s, 2H), 1.35 (d, J=8.0 Hz, 3H), 1.33 (d, J=7.6 Hz, 3H); MS (Electrospray): m/z 411.4 (M$^+$H).

EXAMPLE 20

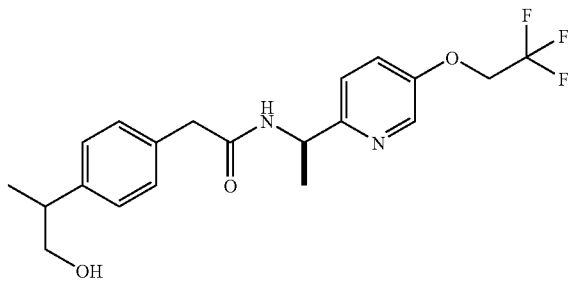

2-[4-(2-hydroxy-1-methylethyl)phenyl]-N-[(1R)-1-(5-(2,2,2-trifluoroethoxy)pyridin-2-yl)ethyl]acetamide A microwave vial was charged with 2-(4-isopropenylphenyl)-N-{(1R)-1-[5-(2,2,2-trifluoroethoxy)pyridin-2-yl]ethyl}acetamide (300 mg, 0.793 mmol) and THF (500 uL). The solution was cooled to 0° C. and borane tetrahydrofuran complex (1.19 mL, 1.19 mmol) was added via syringe. The reaction was warmed to room temperature over 1.5 h., then NaOH (5M, 634 uL, 3.17 mmol) was added dropwise, followed by the slow addition of hydrogen peroxide (30 wt. % in water, 991 uL, 8.72 mmol). After stirring for 30 min, the mixture was diluted with CH$_2$Cl$_2$ (30 mL) and water (30 mL), and the layers were separated. The aqueous layer was washed with CH$_2$Cl$_2$ (2×15 mL) and the combined organic layer was dried over MgSO$_4$, filtered, and concentrated. The resulting crude material was purified by normal phase chromatography (20-100% EtOAc/Hexanes) to give 133 mg (42%) of 2-[4-(2-hydroxy-1-methylethyl)phenyl]-N-{(1R)-1-[5-(2,2,2-trifluoroethoxy)pyridin-2-yl]ethyl}acetamide as a colorless oil. $^1$H NMR (CDCl$_3$, 400 MHz) δ 8.20 (d, J=2.57 Hz, 1H), 7.21 (m, 6H), 6.69 (d, J=6.96 Hz, 1H), 5.10 (quint. J=6.96 Hz, 1H), 4.38 (q, J=8.00, 2H), 3.71 (m, 2H), 3.57 (s, 2H), 2.96 (m, 1H), 1.40 (d, J=6.67 Hz, 3H), 1.28 (d, J=6.96 Hz, 3H); MS (Electrospray): m/z 397.4 (M+H). The two diastereomers were separable by chiral HPLC under the following conditions: Column: ChiralPak AD (4.6 mm×250 mm, 10 u), Solvent: Hex/EtOH/MeOH (85/7.5/7.5), 1 mL/L diethylamine, Flow rate: 1 mL/min, Retention times: 11.3 and 12.8 min

EXAMPLE 21

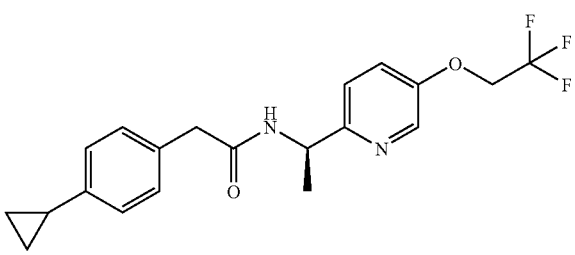

2-(4-Cyclopropylphenyl)-N-((1R)-1-{5-[(2,2,2-trifluoroethyl)oxo]pyridin-2-yl}ethylacetamide To a 1 l round-bottom flask equipped with a magnetic stir bar were added ethyl 4-bromophenylacetate (25.00 g, 103.0 mmol), cyclopropyl boronic acid (11.48 g, 134.0 mmol), tricyclohexyl phosphine (2.880 g, 10.28 mmol) and K$_3$PO$_4$ (76.00 g, 360.0 mmol) into 420 ml of toluene/H$_2$O (20:1) mixed solvent. Under nitrogen, palladium(II) acetate (1.154 g, 5.140 mmol) was added. The resulting mixture was stirred at 100° C. for 16 h, and then cooled to room temperature. It was diluted with EtOAc (200 ml) and water (400 ml), and the two layers were separated. The aqueous layer was extracted with EtOAc (200 ml). The combined organic layers were washed with water (400 ml) and brine, dried over anhydrous Na$_2$SO$_4$, filtered. The filtrate was concentrated in vacuum to give 19.00 g of yellow-brown oil as the crude product. Purification by flash chromatography (SiO$_2$, 5-18% ethyl acetate in hexanes, gradient) gave the title compound as a light yellow oil (16.20 g, 77.0%). $^1$H NMR (CDCl$_3$, 400 MHz) δ 7.164 (d, J=8.25 Hz, 2H); 7.021 (m, 2H); 4.133 (q, J=7.14 Hz, 2H); 3.556 (s, 2H); 1.867 (m, 1H); 1.242 (t, J=7.14 Hz, 3H); 0.936 (m, 2H); 0.669 (m, 2H); MS (Electrospray): m/z 205.1 (M+H). To a solution of ethyl 4-cyclophenylacetate (16.20 g, 79.00 mmol) in methanol (100.0 ml) was added drop wise 1.0 N LiOH water solution (100.0 ml, 100.0 mmol). The resulting mixture was stirred at room temperature for 16 h. The solvent was evaporated under reduced pressure. To the remained solution was titrated with 1.0 N HCl drop wise while stirring to pH→2. A white precipitate was collected by filtration and washed with distilled water. Dried under vacuum to afford the title compound as a white solid (13.80 g, 99.0%). $^1$H NMR (CDCl$_3$, 400 MHz) δ 7.149 (d, J=8.25 Hz, 2H); 7.022 (dd, L=1.74 Hz, J=8.24 Hz, 2H); 3.581 (s, 2H); 1.864 (m, 1H); 0.935 (m, 2H); 0.666 (m, 2H); MS (Electrospray): m/z 177.1 (M+H). To a 100 ml round bottom flask equipped with a magnetic stir bar were added 4-cyclopropyl-phenylacetic acid (1.040 g, 5.902 mmol), (1R)-1-{5-[(2,2,2-trifluoroethyl)oxo]pyridin-2-yl}ethylamine dihydrochloride (1.730 g, 5.902 mmol), 1-(3-dimethylaminopropyl)-3-ethyl-carbodiimide hydrochloride (1.131 g, 5.902 mmol), 1-hydroxy-7-azabenzotriazole (0.803 g, 5.902 mmol) and triethylamine (1.645 ml, 11.80 mmol) into 20.0 ml of CH$_2$Cl$_2$. The resulting solution was stirred at room temperature for 3 hours. The reaction mixture was diluted with water and the two layers were separated. The aqueous layer was extracted with CH$_2$Cl$_2$. The combined organic layers were washed with brine, dried over anhydrous Na$_2$SO$_4$ and filtered. The filtrate was concentrated in vacuum. Purification by flash chromatography (10-50% EtOAc/Hexanes) gave 2-(4-Cyclopropylphenyl)-N-((1R)-1-{5-[(2,2,2-trifluoroethyl)oxo]pyridin-2-yl}ethyl)acetamide as a white solid (2.000 g, 90%). $^1$H NMR (CDCl$_3$, 400 MHz) δ 8.210 (d, J=2.74 Hz, 1H); 7.195 (d, J=2.75 Hz, 1H); 7.172 (s, 1H); 7.147 (m, 2H); 7.040 (m, 2H); 6.590 (d, J=7.33 Hz, 1H); 5.103 (dq, J=7.15 Hz, 1H); 4.374 (dd, J=7.88 Hz, J=8.05 Hz, 2H); 3.534 (dd, J=1.10 Hz, J=15.93 Hz, 2H); 1.886 (m, 1H); 1.380 (d, J=6.77 Hz, 3H); 0.960 (m, 2H); 0.683 (m, 2H); MS (Electrospray): m/z 379.1 (M+H).

EXAMPLE 22

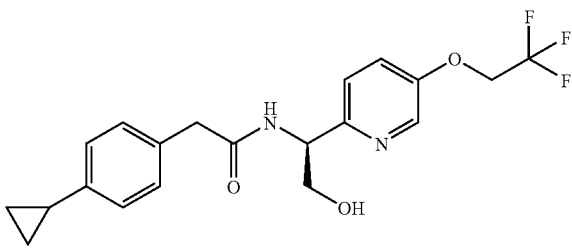

2-(4-cyclopropylphenyl)-N-{(1S)-2-hydroxy-1-[5-(2,2,2-trifluoroethoxypyridin-2-yl]ethyl}acetamide To a mixture of 2-methyl-N-{(1E)-[5-(2,2,2-trifluoroethoxy)pyridin-2-yl]methylidene}propane-2-sulfinamide (10.0 g, 32.4 mmol) and tetrahydrofuran (150 ml) at −78° C. was added dropwise 1.0M vinylmagnesium bromide in tetrahydrofuran (58.4 ml, 58.4 mmol), maintaining temperature during addition below −70° C. Reaction was stirred at −78° C. for an hour. To complete reaction, an additional amount of 1.0M vinylmagnesium bromide (19.4 ml, 19.4 mmol) was required. The reaction was then quenched by pouring mixture into a cold solution of saturated $NH_4Cl$ (800 ml) and ethyl acetate (600 ml) with vigorous stirring at 0° C. Layers were separated and organic extracts were combined, dried over $Na_2SO_4$, filtered and concentrated in vacuum. The resulting brown oil was purified by flash chromatography ($Si_2O$, 25-100% ethyl acetate in hexanes, gradient) to give 2-{(1R)-1-[(tert-butylthio)amino]prop-2-enyl}-5-(2,2,2-trifluoroethoxy)pyridine as a white solid (8.10 g, 73.5%). $^1$H NMR (400 MHz, $CDCl_3$) δ 8.30 (d, J=2.8 Hz, 1H), 7.28 (m, 2H), 5.92-5.83 (m, 1H), 5.34 (dd, J=16 Hz and 33 Hz, 2H), 5.01 (m, 1H), 4.99 (bs, 1H), 4.39 (q, J=8.0 Hz, 2H), 1.28 (s, 9H); MS (Electrospray): m/z 337.1 (+H).

Ozone was bubbled through a mixture of (R)-2-methyl-N-[(5-(2,2,2-trifluoroethoxy)pyridine-2-yl)methylene]propane-2-sulfinamide (8.10 g, 24.1 mmol) in a 1:1 mixture of dichloromethane and methanol (96 ml) at −78° C. until no starting material was observed by LC/MS. Nitrogen was bubbled through the reaction for fifteen minutes. To the solution was added in portions sodium borohydride (3.64 g, 96.0 mmol) over ten minutes. The reaction was allowed to warm to room temperature, stirred for 16 hours and then concentrated in vacuum. The resulting residue was washed with brine (2×60 ml) and extracted with ethyl acetate (2×75 ml). The organic extracts were combined, dried over $Na_2SO_4$, filtered and concentrated to give an oil. Purification by flash chromatography ($SiO_2$, 50-100% ethyl acetate in hexanes, followed by 0-10% methanol in ethyl acetate, gradient) gave N-{(1S)-2-hydroxy-1-[5-(2,2,2-trifluoroethoxy)pyridin-2-yl]ethyl}-2-methylpropane-2-sulfinamide as a white solid (5.10 g, 61.6%); $^1$H NMR (400 MHz, $CDCl_3$) δ 8.28 (d, J=2.8 Hz, 1H), 7.42 (d, J=8.4 Hz, 1H), 7.28 (dd, J=2.8 Hz and 8.4 Hz, 1H), 4.62-4.60 (m, 1H), 4.53-4.48 (m, 1H), 4.39 (q, J=8.0 Hz, 2H), 3.91-3.88 (m, 2H), 3.22 (m, 1H), 1.27 (s, 9H); MS (Electrospray): m/z 341.1 (M$^+$H).

To a solution of N-{(1S)-2-hydroxy-1-[5-(2,2,2-trifluoroethoxy)pyridin-2-yl]ethyl}-2-methylpropane-2-sulfinamide (3.84 g, 11.3 mmol) and methanol (50 ml) was added 2.0N HCl in ether (45.1 ml, 90 mmol). The reaction was stirred for an hour and concentrated to give (2S)-2-amino-2-[5-(2,2,2-trifluoroethoxy)pyridin-2-yl]ethanol dihydrochloride as a white foam (3.49 g, 100%). MS (Electrospray): m/z 237.1 (M$^+$H). To a 100 ml round bottom flask equipped with a magnetic stir bar were added 4-cyclopropylphenylacetic acid (1.79 g, 10.2 mmol), (2S)-2-amino-2-[5-(2,2,2-trifluoroethoxy)pyridin-2-yl]ethanol dihydrochloride (3.14 g, 10.2 mmol), 1-(3-dimethylaminopropyl)-3-ethylcarbodiimide hydrochloride (2.34 g, 12.2 mmol), 1-hydroxy-7-azabenzotriazole (1.66 g, 12.2 mmol) and triethylamine (4.25 ml, 30.5 mmol) into 68 ml of dimethylformamide. The resulting solution was stirred at room temperature for 16 hours. The reaction mixture was washed with brine (3×50 ml) and extracted with ethyl acetate (3×70 ml). The combined organic layers were dried over anhydrous $Na_2SO_4$ and filtered. The filtrate was concentrated in vacuum to give an oil. Purification by flash chromatography ($SiO_2$, 50-100% EtOAc/Hexanes, gradient) gave 2-(4-cyclopropylphenyl)-N-{(1S)-2-hydroxy-1-[5-(2,2,2-trifluoroethoxy)pyridin-2-yl]ethyl}acetamide as a light yellow solid (3.00 g, 75%); $^1$H NMR (400 MHz, $CD_3OD$) δ 8.28 (d, J=2.4 Hz, 1H), 7.42 (dd, J=2.4 Hz and 6.8 Hz, 1H), 7.29 (d, J=7.2 Hz, 1H), 7.16 (d, J=6.4 Hz, 2H), 7.01 (d, J=6.4 Hz, 2H), 5.07-4.99 (m, 1H), 4.63 (q, J=6.4 Hz, 2H), 3.82-3.79 (m, 2H), 3.54 (s, 2H), 1.89-1.84 (m, 1H), 0.92 (m, 2H), 0.64 (m, 2H); MS (Electrospray): m/z 395.2 (M$^+$H).

EXAMPLE 23

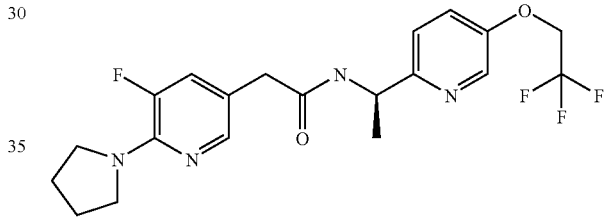

2-(5-fluoro-6-pyrrolidin-1-ylpyridin-3-yl)-N-{(1R)-1-[5-(2,2,2-trifluoroethoxy)pyridin-2-yl]ethyl}acetamide A solution of 2,3-difluoro-5-iodo pyridine (J. Org. Chem. 2005, 70, 3039) (13 g, 37.8 mmol), Pd(PPh$_3$)$_4$ (0.5 g) and Et$_3$N (25 g, 0.25 mol) in MeOH (200 ml) was mixed in a sealed autoclave. After the air in the autoclave was replaced with CO, the pressure was adjusted to 0.3 Mpa, and the reaction mixture was stirred at 65° C. overnight. After cooling to room temperature, the mixture was filtered by suction, the filtrate was concentrated under vacuum, and the residue was purified by column to afford methyl 5-fluoro-6-methoxynicotinate as a white solid (4 g, 57.5%). $^1$H-NMR (400 MHz, CDCl$_3$) δ 8.60 (d, J=2 Hz, 1H, Ar—H), 7.56 (dd, J=10.4 Hz, J$_2$=2 Hz, 1H, Ar—H), 4.09 (s, 3H, —OCH$_3$), 3.92 (s, 3H, —COOCH$_3$)

A mixture of methyl 5-fluoro-6-methoxynicotinate (3.5 g, 18.9 mmol) and KOH (4.2 g, 61.5 mmol) in MeOH (70 ml) was stirred at room temperature for 5 h. After concentration, the residue was dissolved in water, and the obtained solution was washed with ether. The aqueous phase was acidified to pH=1 with dilute hydrochloric acid, and extracted with ether, and the combined organic layers were washed with brine, dried over Na$_2$SO$_4$ and concentrated under vacuum to afford 5-fluoro-6-methoxynicotinic acid (3.2 g, 98%) as a white solid. To a dry-ice cooled solution of 5-fluoro-6-methoxynicotinic acid (3.5 g, 20.5 mmol) and Et₃N (2.3 g, 22.8 mmol) in dry THF (50 ml), was added isobutyl chloroformate (3.1 g, 22.7 mmol) slowly to keep the reaction temperature below −20° C. After the mixture was stirred for 1 h at the same temperature, to it ice-water was added, and the resulting mixture was extracted with ether, and the combined organic layers were washed with brine, dried over Na₂SO₄ and concentrated under vacuum to afford 5.5 g of (5-fluoro-6-methoxypyridin-3-yl)carbonyl isobutyl carbonate as a yellow oil (98%). ¹H-NMR (400 MHz, CDCl₃) δ 8.65 (d, J=2 Hz, 1H, Ar—H), 7.90 (dd, J₁=10 Hz, J2=2 Hz, 1H, Ar—H), 4.11 (s, 3H, —OCH₃), 3.73 (m, 2H, —OCH₂), 2.09 (m, 1H, —CH), 0.98 (m, 6H, —CH₃). A mixture of (5-fluoro-6-methoxypyridin-3-yl)carbonyl isobutyl carbonate (3.7 g, 13.6 mmol) and CH₂N₂-ether (30 mmol) was stirred for 5 h at −40° C. then overnight at room temperature. The reaction was quenched by the addition of water, and the resulting mixture was extracted with ether, and the combined organic layers were washed with brine, dried over Na₂SO₄ and concentrated under vacuum. The residue was purified by column to afford 3 g of 2-diazo-1-(5-fluoro-6-methoxypyridin-3-yl)ethanone (90%). ¹H-NMR (400 MHz, CDCl₃) δ 8.29 (d, J=2 Hz, 1H, Ar—H), 7.79 (dd, J₁=10.4 Hz, J₂=2 Hz, 1H, Ar—H), 5.85 (s, —CH), 4.09 (s, 3H, —OCH₃). A mixture of 2-diazo-1-(5-fluoro-6-methoxypyridin-3-yl)ethanone (6 g, 30.8 mmol) in EtOH (100 ml) was heated to 40° C., then to it was added AgOAc (2 g, 12 mmol) and the resulting mixture was stirred at 70° C. for 2 h. After filtration, the filter cake was washed with THF. The filtrate was concentrated under vacuum, and the residue was purified by column to afford 2.5 g of ethyl (5-fluoro-6-methoxypyridin-3-yl)acetate as a solid (38.5%). ¹H-NMR (400 MHz, CDCl₃) δ 7.86 (d, J=1.6 Hz, 1H, Ar—H), 7.33 (dd, J=10 Hz, J₂=2 Hz, 1H, Ar—H), 4.16 (q, J=7.8 Hz, 2H, —CH₂CH₃), 4.00 (s, 3H, —OCH₃), 3.54 (s, 2H, Ar—CH₂), 1.26 (t, J=7.8 Hz, 3H, —CH₃). A mixture of ethyl (5-fluoro-6-methoxypyridin-3-yl)acetate (2.5 g, 11.7 mol), PCl₅ (5 g, 24 mmol) and DMF (0.5 ml) in POCl₃ (20 ml) was stirred overnight at 80° C. After concentration to remove the excess POCl₃, the residue was poured into ice-water (100 ml), and the solution was neutralized to pH=7 with diluted aq. NaOH, and extracted with ether. The combined organic layers were washed with brine, dried over Na₂SO₄ and concentrated under vacuum, the residue was purified by column to afford 1.5 g of ethyl (6-chloro-5-fluoropyridin-3-yl)acetate as an oil (60%). ¹H-NMR (400 MHz, CDCl₃) δ 8.12 (d, J=1.6 Hz, 1H, Ar—H), 7.50 (dd, J₁=8.4 Hz, J₂=2 Hz, 1H, Ar—H), 4.19 (q, J=8.8 Hz, 2H, —CH₂CH₃), 3.63 (s, 3H, —OCH₃), 1.27 (t, J=8.8 Hz, 3H, —CH₃). A solution of ethyl (6-chloro-5-fluoropyridin-3-yl)acetate (1.5 g, 6.9 mmol) in conc. HCl (30 ml) was stirred at 120° C. for 5 h. After concentration, the residue was poured into water (50 ml), and the resulting mixture was extracted with ether. The combined organic layers was washed with brine, dried over Na₂SO₄ and concentrated under vacuum to afford 0.8 of (6-chloro-5-fluoropyridin-3-yl)acetic acid (61.2%). ¹H-NMR (300 MHz, CDCl₃) δ 8.15 (d, J=1.5 Hz, 1H, Ar—H), 7.51 (dd, J=8.4 Hz, J₂=1.8 Hz, 1H, Ar—H), 3.70 (s, 3H, —OCH₃). A mixture of (6-chloro-5-fluoropyridin-3-yl)acetic acid (2 g, 10.6 mmol) and pyrrolidine (2.2 g, 31.7 mmol) in dioxane (50 ml) was stirred at 110° C. overnight. After concentration, the residue was purified by prep. HPLC to afford 1.2 g (20%) of (5-fluoro-6-pyrrolidin-1-ylpyridin-3-yl)acetic acid TFA salt as a white solid. ¹H-NMR (400 MHz CDCl₃) δ 10.11 (br, 3H, COOH), 7.77 (s, 1H, Ar—H), 7.54 (d, J=13.2 Hz, 1H, Ar—H), 3.80 (m, 4H, CH₂—CH₂), 3.49 (m, Ar—CH₂), 2.09 (m, 4H, CH₂—CH₂). To a 15 ml round bottom flask equipped with a magnetic stir bar were added (5-fluoro-6-pyrrolidin-1-ylpyridin-3-yl)acetic acid (45.9 mg, 0.21 mmol), (R)-1-[5-(2,2,2-trifluoroethoxy)pyridine-2-yl]ethylamine bis-hydrochloride salt (60.0 mg, 0.21 mmol), 1-(3-dimethylaminopropyl)-3-ethylcarbodiimide hydrochloride (47.1 mg, 0.25 mmol), 1-hydroxy-7-azabenzotriazole (33.4 mg, 0.25 mmol) and triethylamine (0.09 ml, 0.61 mmol) into 2.0 ml of dimethylformamide. The resulting mixture was stirred at room temperature for 16 hours. Reaction mixture was directly purified by preparative reversed-phase HPLC to give 2-(5-fluoro-6-pyrrolidin-1-ylpyridin-3-yl)-N-{(1R)-1-[5-(2,2,2-trifluoroethoxy)pyridin-2-yl]ethyl}acetamide bis-TFA salt as an oil (53.0 mg, 39.2%); ¹H NMR (400 MHz, CD₃OD) δ 8.42 (s, 1H), 7.79 (dd, J=2.8 Hz and 8.8 Hz, 1H), 7.73 (dd, J=1.6 Hz and 14 Hz, 1H), 7.62 (d, J=8.8 Hz, 1H), 7.29 (d, J=0.8 Hz, 1H), 5.04 (q, J=6.8 Hz, 1H), 4.71 (q, J=8.4 Hz, 2H), 3.74 (m, 4H), 3.56 (s, 2H), 2.11-2.05 (m, 4H), 1.50 (d, J=6.8 Hz, 3H); MS (Electrospray): m/z 427.1 (M⁺H).

EXAMPLE 24

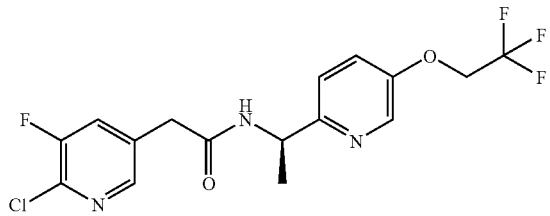

2-(6-chloro-5-fluoropyridine-3-yl)-N-{(1R)-1-[5-(2,2,2-trifluoroethoxy)pyridin-2-yl]ethyl}acetamide To a 50 ml round bottom flask equipped with a magnetic stir bar were added 2-(6-chloro-5-fluoropyridine-3-yl)acetic acid (190.0 mg, 1.000 mmol), (1R)-1-{5-[(2,2,2-trifluoroethyl)oxo]pyridin-2-yl}ethylamine dihydrochloride (293.0 mg, 1.000 mmol), 1-(3-dimethylaminopropyl)-3-ethylcarbodiimide hydrochloride (192.0 mg, 1.000 mmol), 1-hydroxy-7-azabenzotriazole (136.0 mg, 1.000 mmol) and triethylamine (0.2790 ml, 2.000 mmol) into 10.0 ml of CH₂Cl₂. The resulting solution was stirred at room temperature for 3 hours. The reaction mixture was diluted with water and the two layers were separated. The aqueous layer was extracted with CH₂Cl₂. The combined organic layers were washed with brine, dried over anhydrous Na₂SO₄ and filtered. The filtrate was concentrated in vacuum. The residue was dissolved into CH2Cl2 (15 ml). Hexanes was added while stirring until slightly cloudy. A white crystal gradually crystallized on the wall of the flask. The mixture was allowed to sit overnight. The solvent was decanted and the crystal was washed with hexanes (3×10 ml). Dried under vacuum to give 2-(6-chloro-5-fluoropyridine-3-yl)-N-{(1R)-1-[5-(2,2,2-trifluoroethoxy)pyridin-2-yl]ethyl}acetamide as a white solid (286 mg, 73.0%). ¹H NMR (CDCl₃, 400 MHz) δ 8.263 (d, J=2.65 Hz, 1H); 8.122 (d, J=1.56 Hz, 1H); 7.547 (dd, J=1.88 Hz, J=8.75 Hz, 1H); 7.256 (dd, J=2.84 Hz, J=8.51 Hz, 1H); 7.199 (d, J=8.52 Hz, 1H); 6.960 (d, J=6.31 Hz, 1H); 5.095 (dq, J=6.77

Hz, 1H); 4.387 (dd, J=7.97 Hz, J=15.93 Hz, 2H); 3.571 (s, 2H); 1.438 (d, J=6.68 Hz, 3H); MS (Electrospray): m/z 492.0 (M+H).

EXAMPLE 25

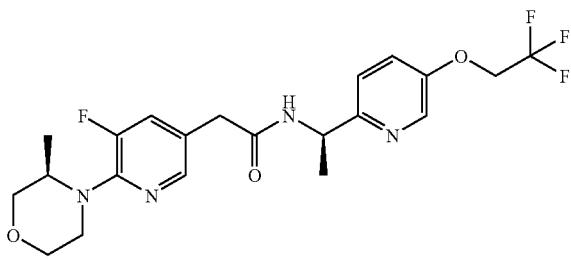

2-{5-fluoro-6-[(3R)-3-methylmorpholin-4-yl]pyridin-3-yl}-N-{(1R)-1-[5-(2,2,2-trifluoroethoxy)pyridin-2-yl]ethyl}acetamide To a sealed microwave reaction vessel containing 2-(6-chloro-5-fluoropyridine-3-yl)-N-{(1R)-1-[5-(2,2,2-trifluoroethoxy)pyridin-2-yl]ethyl}acetamide (39.20 mg, 0.1000 mmol), (3R)-3-methylmorpholine hydrochloride (16.40 mg, 0.1200 mmol), rac-2,2'-Bis(diphenylphosphino)-1,1'-binaphthyl (6.230 mg, 10.00 µmol), Sodium tert-butoxide (25.00 mg, 0.2600 mmol), and Pd$_2$(dba)$_3$ (4.580 mg, 5.000 µmol) was added 1.0 ml of toluene. The reaction mixture was microwave radiated at 120° C. for 15.0 min. It was cooled to room temperature and diluted with CH$_2$Cl$_2$ (2.0 ml). The suspension was filtered, washed with CH$_2$Cl$_2$ (3×2.0 ml), and the filtrate was concentrated under reduced pressure. The residue was purified using reverse phase HPLC to give the titled compound (6.400 mg, 14.0% yield) 2-{5-fluoro-6-[(3R)-3-methylmorpholin-4-yl]pyridin-3-yl}-N-{(1R)-1-[5-(2,2,2-trifluoroethoxy)pyridin-2-yl]ethyl}acetamide. $^1$H NMR (CDCl$_3$, 400 MHz) 8.419 (d, J=2.75 Hz, 1H); 8.270 (d, J=7.14 Hz, 1H); 7.917 (s, 1H); 7.627 (dd, J=2.84 Hz, J=8.70 Hz, 1H); 7.557 (d, J=8.79 Hz, 1H); 7.361 (dd, J=0.65 Hz, J=13.74 Hz, 1H); 5.161 (dq, J=7.14 Hz, 1H); 4.508 (m, 2H); 4.159 (m, 1H); 3.961 (d, J=11.53 Hz, 1H); 3.831 (dd, J=3.03 Hz, J=11.45 Hz, 1H); 3.690 (m, 2H); 3.537 (m, 2H); 3.485 (s, 2H); 1.559 (d, J=7.14 Hz, 3H); 1.286 (d, J=6.78 Hz, 3H); MS (Electrospray): m/z 457.2 (M+H).

EXAMPLE 26

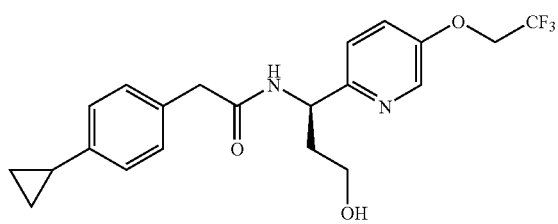

2-(4-cyclopropylphenyl)-N-{(1R)-3-hydroxy-1-[5-(2,2,2-trifluoroethoxypyridin-2-yl]propyl}acetamide To a −78° C. cooled solution of (R)-2-methyl-N-[(5-(2,2,2-trifluoroethoxy)pyridin-2-yl)methylene]propane-2-sulfinamide (25.3 g, 82 mmol) in THF (1000 mL) was added allylmagnesium chloride (2.0M in THF, 59.5 mL, 119 mmol). The Grignard reagent was added at a rate such that the internal reaction temperature was never warmer than −70° C. After complete addition of the Grignard reagent, the mixture was quenched with a saturated ammonium chloride solution and allowed to warm to room temperature. The mixture was diluted with water and EtOAc, and the layers were separated. The aqueous layer was extracted once with EtOAc. The combined organic layer was dried over MgSO$_4$, filtered, and concentrated to give a crude oil. $^1$H-NMR indicated a ~3:1 diastereomeric ratio of products that were separated by silica gel chromatography (10-100% EtOAc/hexanes) to give 2-methyl-N-{(1R)-1-[5-(2,2,2-trifluoroethoxy)pyridin-2-yl]but-3-en-1-yl}propane-2-sulfinamide (19.4 g, 67%) as a yellow oil; $^1$H NMR (400 MHz, CDCl$_3$) δ 8.30 (d, J=2.7 Hz, 1H), 7.07-7.25 (m, 2H), 5.64-5.74 (m, 1H), 5.01-5.30 (m, 2H), 4.60 (d, J=7.3 Hz, 1H), 4.46 (q, J=7.0 Hz, 1H), 4.38 (q, J=7.9 Hz, 2H), 2.56-2.61 (m, 2H), 1.25 (s, 9H); MS (Electrospray): m/z 350.8 (M. A solution of 2-methyl-N-{(1R)-1-[5-(2,2,2-trifluoroethoxy)pyridin-2-yl]but-3-en-1-yl}propane-2-sulfinamide (11.6 g, 33.0 mmol) in methanol (300 mL) and CH$_2$Cl$_2$ (300 mL) was cooled to −78° C. Ozone was bubbled into the reaction mixture until the solution turned pale blue (30 minutes). The ozone source was then removed and NaBH$_4$ (6.24 g, 165 mmol) was added. The reaction mixture was allowed to warm to room temperature overnight. Water (200 mL) was added and the layers were separated. The aqueous layer was extracted with CH$_2$Cl$_2$ (2×150 mL) and the combined organic was dried over MgSO$_4$, concentrated and purified by silica gel chromatography (40-100% EtOAc/hexanes) to give N-{(1R)-3-hydroxy-1-[5-(2,2,2-trifluoroethoxy)pyridine-2-yl]propyl}-2-methylpropane-2-sulfinamide (8.9 g, 78%) as a brown solid; $^1$H NMR (400 MHz, CDCl$_3$) δ 8.30 (d, J=2.9 Hz, 1H), 7.11-7.34 (m, 2H), 4.57-4.69 (m, 2H), 4.39 (q, J=7.9 Hz, 2H), 3.67-3.80 (m, 2H), 2.46 (t, J=5.3 Hz, 1H), 2.04 (q, J=6.0 Hz, 2H), 1.26 (s, 9H); MS (Electrospray): m/z 354.8 (M$^+$H). To a solution of N-{(1R)-3-hydroxy-1-[5-(2,2,2-trifluoroethoxy)pyridine-2-yl]propyl}-2-methylpropane-2-sulfinamide (1 g, 2.8 mmol) in MeOH (20 mL) was added HCl in ether (2M, 3.1 mL, 6.2 mmol). After stirring for 2 hours at room temperature, the mixture was concentrated to give a yellow oil. The yellow oil was foamed under high vacuum and triturated with ethyl ether (100 mL) to give (3R)-3-amino-3-[5-(2,2,2-trifluoroethoxy)pyridin-2-yl]propan-1-ol as the bis-hydrochloride salt; MS (Electrospray): m/z 250.9 (M$^+$H). To a suspension of (3R)-3-amino-3-[5-(2,2,2-trifluoroethoxy)pyridin-2-yl]propan-1-ol bis-HCl (0.91 g, 2.8 mmol), 4-cyclopropylphenylacetic acid (0.50 g, 2.8 mmol), EDC (0.65 g, 3.4 mmol), and 1-hydroxy-7-azabenzotriazole (0.46 g, 3.4 mmol) in DCM (40 mL) was added diisopropylethylamine (2.85 mL, 16.3 mmol). After stirring overnight at room temperature, the mixture was washed with water (2×50 mL). The organic layer was dried over MgSO$_4$, filtered, concentrated and purified by silica gel chromatography (20-100% EtOAc/hexanes) to give 2-(4-cyclopropylphenyl)-N-{(1R)-3-hydroxy-1-[5-(2,2,2-trifluoroethoxy)pyridin-2-yl]propyl}acetamide (0.87 g, 76%) as a colorless, waxy solid; $^1$H NMR (400 MHz, CDCl$_3$) δ 8.20 (d, J=2.8 Hz, 1H), 7.04-7.26 (m, 6H), 5.18-5.24 (m, 1H), 4.39 (q, J=7.9 Hz, 2H), 4.03-4.06 (m, 1H), 3.50-3.65 (m, 4H), 1.86-2.01 (m, 2H), 1.52-1.60 (m, 1H), 0.94-0.99 (m, 2H), 0.67-0.71 (m, 2H); MS (Electrospray): m/z 408.9 (M$^+$H).

EXAMPLE 27

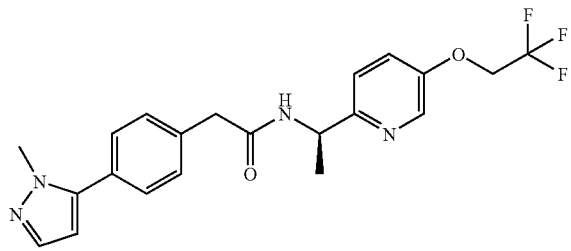

2-[4-(1-methyl-1H-pyrazol-5-yl)phenyl]-N-{(1R)-1-[5-(2,2,2-trifluoroethoxy)pyridin-2-yl]ethyl}acetamide To a 5° C. solution of 5.00 mL (60.9 mmol) n-methylpyrazole in 100 ml THF was added dropwise 381 mL (60.9 mmol) 1.6M n-BuLi in hexanes. The reaction mixture was warmed to room temperature, and after 1 hr at room temperature, the reaction mixture was cooled to −78° C. 18.4 mL (79.0 mmol) isopropyl borate was added. After 1.00 h at −78° C., the reaction mixture was quenched with 12.0 mL of 2N HCl. The resulting solution was concentrated in vacuo and azotroped with toluene. The resulting crude material was dissolved in 11 mL THF. 6.57 g (55.6 mmol) pincol and 1.00 g of molecular sieves were added. After 24.0 hr at room temperature, the reaction mixture was filtered and concentrated. The resulting residue was dissolved in 100 mL hexanes, washed twice with water, dried over NaSO4, filtered, and concentrated in vacuo to afford 5.90 g (51%) 1-methyl-5-(4,4,5,5-tetramethyl-1,3,2-dioxaborolan-2-yl)-1H-pyrazole. 1H NMR (CD$_3$OD, 400 MHz) 7.45 (d, 1H, J=1.92); 7.67 (d, 2H, J=1.92 Hz); 4.04 (s, 3H); 1.35 (s, 12H). ESMS+1 for $C_{10}H_{17}BN_2O_2$: 209.1. To a sealed vessel containing 9.20 g (19.8 mmol) 2-(4-iodophenyl)-N-{(1R)-1-[5-(2,2,2-trifluoroethoxy)pyridin-2-yl]ethyl}acetamide, 4.95 g (23.8 mmol) 1-methyl-5-(4,4,5,5-tetramethyl-1,3,2-dioxaborolan-2-yl)-1H-pyrazole, 0.133 g (0.476 mmol) tricyclohexylphosphine, and 0.181 g (0.198 mmol) Pd$_2$(dba)$_3$ was added 52.8 mL dioxane and 26.5 mL of 1.27M K$_3$PO$_4$. After 12.0 h at 100° C., the reaction mixture was cooled to room temperature and extracted three times with CH$_2$Cl$_2$ and washed with brine. The organic layer was dried over NaSO4, filtered and concentrated in vacuo. Purification by flash chromatography (1×14 cm silica gel, linear gradient 50-100% EtOAc:hexane). The resulting solid was recrystallized from n-butylchloride to afford 5.00 g (60%) 2-[4-(1-methyl-1H-pyrazol-5-yl)phenyl]-N-{(1R)-1-[5-(2,2,2-trifluoroethoxy)pyridin-2-yl]ethyl}acetamide. $^1$H NMR (CDCl$_3$, 400 MHz) 8.23 (d, 1H, J=2.74 Hz); 7.51 (d, 1H, J=1.83 Hz); 7.38 (m, 4H); 7.22 (m, 2H); 6.79 (br d, 1H, J=7.15 Hz); 6.30 (d, 1H, J=2.01 Hz); 5.13 (m, 1H); 4.38 (q, 2H, J=8.05 Hz); 3.90 (s, 3H); 3.63 (s, 2H); 1.43 (d, 3H, J=6.78). HRMS (ES) exact mass calcd for $C_{21}H_{21}F_3N_4O_2$: 419.1682, Found: 419.1690.

EXAMPLE 28

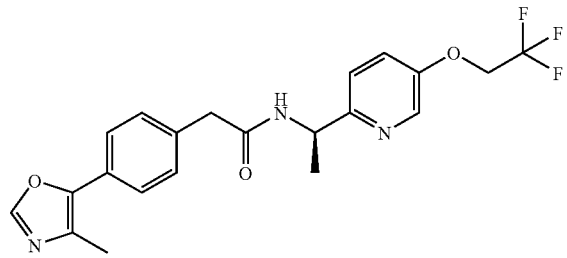

2-[4-(4-methyl-1,3-oxazol-5-yl)phenyl]-N-{(1R)-1-[5-(2,2,2-trifluoroethoxy)pyridin-2-yl]ethyl}acetamide To a solution of 3.00 g (14.0 mmol) 4-bromophenyl acetic acid in 25.0 ml DMF was added 3.60 g (27.9 mmol) 4-methyl-1,3-oxazole-5-carboxylic acid, 6.80 g (20.9 mmol) cesium carbonate, 4.1 g (14.0 mmol) tetrabutyl ammonium chloride monohydrate, and 0.400 g (0.700 mmol) bis(tri-t-butylphosphine)palladium(0). After 3.00 h at 140° C., the reaction mixture was, diluted with CH$_2$Cl$_2$, washed with 10% citric acid, washed twice with water, and washed with brine. The organic layer was dried over NaSO$_4$, filtered and concentrated in vacuo. Purification by preparative HPLC (5→95% CH$_3$CN/H$_2$O over 20 min, 0.05% added TFA, C18 50×150 mm) afforded 0.730 g (24%) [4-(4-methyl-1,3-oxazol-5-yl)phenyl]acetic acid. $^1$H NMR (CD$_3$OD, 400 MHz) δ 8.14 (s, 1H); 7.61 (d, 2H, J=8.32 Hz); 7.41 (d, 2H, J=8.33 Hz); 3.65 (s, 2H); 2.41 (s, 3H). ESMS+1 for $C_{12}H_{11}NO_3$: 218.1. To a solution of 0.725 g (3.34 mmol) [4-(4-methyl-1,3-oxazol-5-yl)phenyl]acetic acid in 7.00 ml CH$_2$Cl$_2$ was added 0.978 g (3.34 mmol) 2-[(1R)-1-ammonioethyl]-5-(2,2,2-trifluoroethoxy)pyridinium dichloride, 0.591 g (4.34 mmol) HOAT, 0.832 g (4.34 mmol) EDC, and 1.75 mL (10.0 mmol) DIEA. After 24.0 h at room temperature, the reaction mixture was diluted with CH$_2$Cl$_2$, washed three times with water, and washed with brine. The organic layer was dried over NaSO$_4$, filtered and concentrated in vacuo. Purification by flash chromatography (1×14 cm silica gel, linear gradient 20-100% EtOAc:hexane) afforded 0.720 g (51.4%) 2-[4-(4-methyl-1,3-oxazol-5-yl)phenyl]-N-{(1R)-1-[5-(2,2,2-trifluoroethoxy)pyridin-2-yl]ethyl}acetamide. $^1$H NMR (CDCl$_3$, 400 MHz) δ 8.22 (d, 1H, J=2.38 Hz); 7.83 (s, 1H); 7.59 (dd, 2H, J=1.83 Hz, 6.59 Hz); 7.36 (d, 2H, J=8.42 Hz); 7.22 (m, 2H); 6.72 (br d, 1H, J=7.51 Hz); 5.12 (m, 1H); 4.38 (q, 2H, J=8.06 Hz); 3.62 (s, 2H); 2.45 (s, 3H); 1.41 (d, 3H, J=6.78). HRMS (ES) exact mass calcd for $C_{21}H_{20}F_3N_3O_3$: 420.1540, Found: 420.1530.

EXAMPLE 29

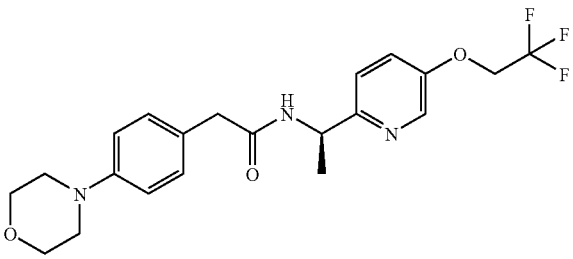

2-(4-morpholin-4-ylphenyl)-N-{(1R)-1-[5-(2,2,2-trifluoroethoxy)pyridin-2-yl]ethyl}acetamide To a sealed microwave reaction vessel containing ethyl 4-bromophenylacetate (1.220 g, 5.019 mmol), morphine (0.5250 ml, 6.002 mmol), 2-(dicyclohexylphosphino)-2'-(N,N-dimethylamino)biphenyl (154.0 mg, 0.3760 mmol), $K_3PO_4$ (1.491 g, 7.026 mmol), and $Pd_2(dba)_3$ (230.0 mg, 0.2510 mmol) was added 3.0 ml of ethylene glycol dimethyl ether. The reaction mixture was microwave radiated at 120° C. for 20.0 min. It was cooled to room temperature and diluted with $CH_2Cl_2$ (20.0 ml). The suspension was filtered, washed with $CH_2Cl_2$ (3×10.0 ml), and the filtrate was washed with water and brine. The organic layer was dried over anhydrous $Na_2SO_4$— filtered. The filtrate was concentrated. The residue was purified by flash chromatography ($SiO_2$, 5-40% ethyl acetate in hexanes, gradient) gave the title compound as a light yellow oil (470.0 mg, 37%). $^1$H NMR ($CDCl_3$, 400 MHz) δ 7.193 (m, 2H); 6.872 (m, 2H); 4.272 (q, J=7.14 Hz, 2H); 3.853 (m, 2H); 3.533 (s, 2H); 3.140 (m, 2H); 1.247 (t, J=7.14 Hz, 3H); MS (Electrospray): m/z 250.1 (M+H). To a solution of ethyl 4-(morphin-4-yl)phenylacetate (450.0 mg, 1.805 mmol) in Methanol (5.0 ml) was added drop wise 1.0 N LiOH water solution (2.707 ml, 2.707 mmol). The resulting mixture was stirred at room temperature for 3 h. The solvent was evaporated under reduced pressure. The residue was suspended into $CH_2Cl_2$ (20.0 ml). To the suspension was added drop wise conc. HCl until most of the white solid was dissolved. The solution was dried over anhydrous $Na_2SO_4$, filtered. The filtrate was concentrated. Dried under vacuum to afford the title compound 4-(Morphin-4-yl)phenylacetic acid as a white solid (360.0 mg, 90%). $^1$H NMR ($CD_3OD$, 400 MHz) δ 7.61 (d, J=8.61 Hz, 2H); 7.517 (d, J=8.60 Hz, 2H); 4.140 (t, J=4.67 Hz, 4H); 3.713 (s, 2H); 3.699 (t, J=19.60 Hz, 4H); MS (Electrospray): m/z 222.1 (M+H). 2-(4-morpholin-4-ylphenyl)-N-{(1R)-1-[5-(2,2,2-trifluoroethoxy)pyridin-2-yl]ethyl}acetamide is prepared as described in Example 28. $^1$H NMR ($CDCl_3$, 400 MHz) δ 8.214 (d, J=2.75 Hz, 1H); 7.208 (dd, J=2.75 Hz, J=8.60 Hz, 1H); 7.171 (d, J=8.60 Hz, 1H); 7.170 (d, J=8.43 Hz, 2M); 6.884 (m, 2H); 6.575 (d, J=7.33 Hz, 1H); 5.109 (dq, J=7.14 Hz, 1H); 4.376 (dd, J=7.97 Hz, J=15.97 Hz, 2H); 3.869 (t, J=4.76 Hz, 4H); 3.510 (dd, J=15.93 Hz, J=18.13 Hz, 2H); 3.156 (t, J=4.76 Hz, 4H); 1.379 (d, J=6.78 Hz, 3H); MS (Electrospray): m/z 424.1 (M+H).

EXAMPLE 30

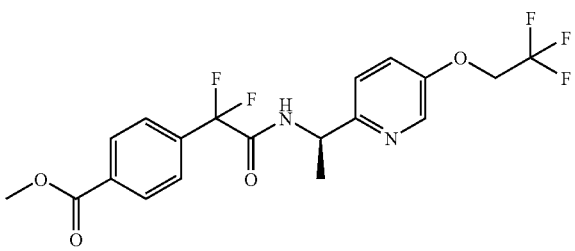

Methyl 4-[1,1-difluoro-2-oxo-2-({(1R)-1-[5-(2,2,2-trifluoroethoxy)pyridin-2-yl]ethyl}amino)ethyl]benzoate To a solution of 0.400 g (1.72 mmol) difluoro[4-(methoxycarbonyl)phenyl]acetic acid in 3.50 ml $CH_2Cl_2$ was added 0.560 g (1.90 mmol) 2-[(1R)-1-ammonioethyl]-5-(2,2,2-trifluoroethoxy)pyridinium dichloride, 0.308 g (2.26 mmol) HOAT, 0.433 g (2.26 mmol) EDC, and 0.91 mL (5.21 mmol) DIEA. After 24.0 h at room temperature, the reaction mixture was diluted with $CH_2Cl_2$, washed three times with water, and washed with brine. The organic layer was dried over $NaSO_4$, filtered and concentrated in vacuo. Purification by flash chromatography (1×14 cm silica gel, linear gradient 0-30% EtOAc:hexane) afforded 0.485 g (65%) Methyl 4-[1,1-difluoro-2-oxo-2-({(1R)-1-[5-(2,2,2-trifluoroethoxy)pyridin-2-yl]ethyl]-amino)ethyl]-benzoate. $^1$H NMR ($CDCl_3$, 400 MHz) 8.32 (d, 1H, J=2.84 Hz); 8.10 (d, 2H, J=8.05 Hz); 7.93 (br d, 1H, J=5.95 Hz); 7.71 (d, 2H, J=8.25 Hz); 7.28 (d, 1H, J=2.75 Hz); 7.23 (d, 1H, J=17.12 Hz); 5.19 (m, 1H); 4.41 (q, 2H, J=7.87 Hz); 3.93 (d, 3H, J=0.55 Hz); 1.49 (d, 3H, J=6.68). ESMS+1 for $C_{19}H_{17}F_5N_2O_4$: 433.1.

EXAMPLE 31

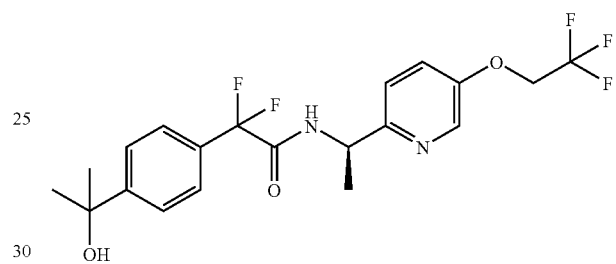

2,2-difluoro-2-[4-(1-hydroxy-1-methylethyl)phenyl]-N-{(1R)-1-[5-(2,2,2-trifluoroethoxy)-pyridin-2-yl]ethyl}acetamide To a solution of 0.370 g (0.856 mmol) Methyl 4-[1,1-difluoro-2-oxo-2-({(1R)-1-[5-(2,2,2-trifluoroethoxy)pyridin-2-yl]ethyl}amino)ethyl]benzoate in 2.00 ml THF was added 1.28 mL (3.85 mmol) 3.0M methyl magnesium bromide in ether. After 20.0 min at room temperature, the reaction mixture was quenched with saturated $NH_4Cl$, extracted twice with $CH_2Cl_2$, and washed with brine. The organic layer was dried over $NaSO_4$, filtered and concentrated in vacuo. Purification by flash chromatography (1×14 cm silica gel, linear gradient 0-10% MeOH:$CH_2Cl_2$) afforded 0.284 g (77%) 2,2-difluoro-2-[4-(1-hydroxy-1-methylethyl)phenyl]-N-{(1R)-1-[5-(2,2,2-trifluoroethoxy)pyridin-2-yl]ethyl}acetamide. $^1$H NMR ($CDCl_3$, 400 MHz) 8.32 (d, 1H, J=2.84 Hz); 7.88 (br d, 1H, J=6.23 Hz); 7.57 (q, 4H, J=8.61 Hz); 7.26 (d, 1H, J=8.52 Hz); 7.21 (d, 1H, J=8.51 Hz); 5.11 (m, 1H); 4.41 (q, 1H, J=7.97); 1.58 (s, 6H); 1.49 (d, 3H, J=6.78). ESMS+1 for $C_{20}H_{21}F_5N_2O_3$: 433.1.

EXAMPLE 32

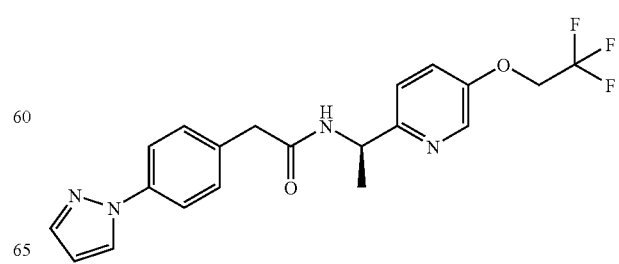

2-[4-(1H-pyrazol-1-yl)phenyl]-N-{(1R)-1-[5-(2,2,2-trifluoroethoxypyridin-2-yl]ethyl}acetamide To a 50 ml round bottom flask equipped with a magnetic stir bar were added 4-iodophenylacetic acid (1.048 g, 4.000 mmol), (1R)-1-{5-[(2,2,2-trifluoroethyl)oxo]pyridin-2-yl}ethylamine dihydrochloride (1.172 g, 4.000 mmol), 1-(3-dimethylaminopropyl)-3-ethylcarbodiimide hydrochloride (0.767 g, 4.000 mmol), 1-hydroxy-7-azabenzotriazole (0.544 g, 4.000 mmol) and triethylamine (1.115 ml, 8.000 mmol) into 10.0 ml of CH$_2$Cl$_2$. The resulting solution was stirred at room temperature for 3 hours. The reaction mixture was diluted with water and the two layers were separated. The aqueous layer was extracted with CH$_2$Cl$_2$. The combined organic layers were washed with brine, dried over anhydrous Na$_2$SO$_4$ and filtered. The filtrate was concentrated in vacuum. The residue was dissolved into CH$_2$Cl$_2$ (20 ml). Hexanes was added while stirring until slightly cloudy. A white crystal gradually crystallized on the wall of the flask. The mixture was allowed to sit overnight. The solvent was decanted and the crystal was washed with hexanes (3×10 ml). Dried under vacuum to give 2-(4-iodophenyl)-N-((1R)-1-{5-[(2,2,2-trifluoroethyl)oxo]pyridin-2-yl}ethyl)acetamide as a white solid (1.700 g, 92%). $^1$H NMR (CDCl$_3$, 400 MHz) (8.226 (d, J=2.75 Hz, 1H); 7.657 (d, J=8.33 Hz, 2H); 7.223 (dd, J=2.89 Hz, J=8.57 Hz, 1H); 7.169 (d, J=8.51 Hz, 2H); 7.031 (d, J=8.15 Hz, 2H); 6.736 (d, J=6.87 Hz, 1H); 5.091 (dq, J=7.01 Hz, 1H); 4.387 (dd, J=7.97 Hz, J=15.93 Hz, 2H); 3.513 (s, 2H); 1.400 (d, J=6.77 Hz, 3H); MS (Electrospray): m/z 465.0 (M+H). To a sealed microwave reaction vessel containing 2-(4-iodophenyl)-N-{(1R)-1-[5-(2,2,2-trifluoroethoxy)pyridin-2-yl]ethyl}acetamide (116.0 mg, 0.2500 mmol), pyrazole (26.00 mg, 0.3750 mmol), salicylaldoxime (7.000 mg, 0.05000 mmol), Cs$_2$CO$_3$ (130.0 mg, 0.4000 mmol), and Cu$_2$O (2.000 mg, 0.01200 mmol) was added 3.0 mL of CH$_3$CN. The reaction mixture was microwave radiated at 150° C. for 20.0 min. It was cooled to room temperature and diluted with CH$_2$Cl$_2$ (2.0 ml). The suspension was filtered, washed with CH$_2$Cl$_2$ (3×2.0 ml), and the filtrate was concentrated under reduced pressure. The residue was purified using reverse phase HPLC to give the titled compound (65.00 mg, 64% yield) 2-[4-(pyrazol-1-yl)phenyl]-N-{(1R)-1-[5-(2,2,2-trifluoroethoxy)pyridin-2-yl]ethyl}acetamide. $^1$H NMR (CDCl$_3$, 400 MHz) 8.209 (d, J=2.56 Hz, 1H); 7.920 (d, J=2.38 Hz, 1H); 7.727 (d, J=2.47 Hz, 1H); 7.673 (m, 2H); 7.368 (m, 2H); 7.217 (dd, J=2.84 Hz, J=8.51 Hz, 1H); 7.160 (d, J=8.24 Hz, 1H); 6.721 (d, J=7.14 Hz, 1H); 6.475 (dd, J=2.02 Hz, J=2.38 Hz, 1H); 5.114 (dq, J=6.96 Hz, 1H); 4.373 (dd, J=8.06 Hz, J=15.93 Hz, 2H); 3.617 (s, 21); 1.400 (d, J=6.78 Hz, 311); MS (Electrospray): m/z 405.1 (M+H).

TABLE 1

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| *(structure shown)* | 2-(4-tert-butylphenyl)-N-[(1R)-1-(5-methoxypyridin-2-yl)ethyl]-acetamide | 327.2 |
| *(structure shown)* | 2-(4-tert-butylphenyl)-N-[(1S)-2,2,2-trifluoro-1-(5-methoxypyridin-2-yl)ethyl]acetamide | 381.2 |
| *(structure shown)* | 2-(4-tert-butylphenyl)-N-[(1R)-1-(5-chloropyridin-2-yl)ethyl]acetamide | 331.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 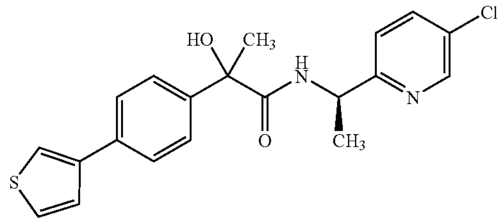 | N-[(1R)-1-(5-chloropyridin-2-yl)ethyl]-2-hydroxy-2-[4-(3-thienyl)phenyl]-propanamide | 386 |
| 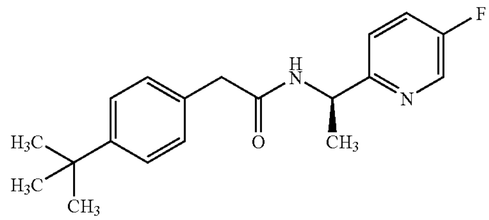 | 2-(4-tert-butylphenyl)-N-[(1R)-1-(5-fluoropyridin-2-yl)ethyl]acetamide | 315.1 |
| 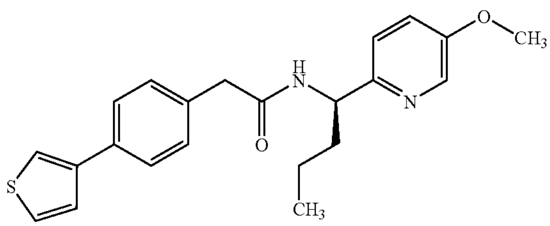 | N-[(1R)-1-(5-methoxypyridin-2-yl)butyl]-2-[4-(3-thienyl)phenyl]-acetamide | 381.1 |
| 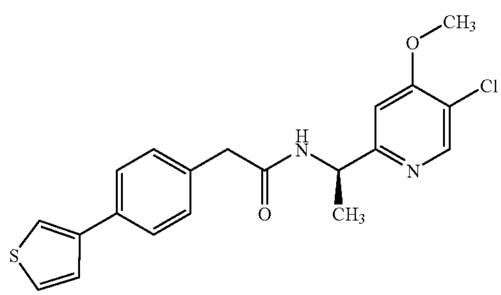 | N-[(1R)-1-(5-chloro-4-methoxypyridin-2-yl)ethyl]-2-[4-(3-thienyl)phenyl]acetamide | 387 |
| 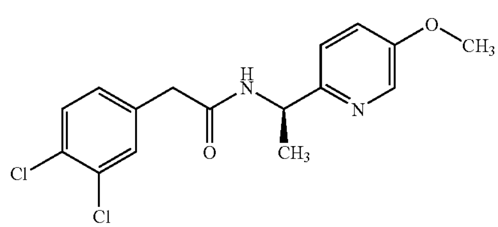 | 2-(3,4-dichlorophenyl)-N-[(1R)-1-(5-methoxypyridin-2-yl)ethyl]acetamide | 339.2 |
| 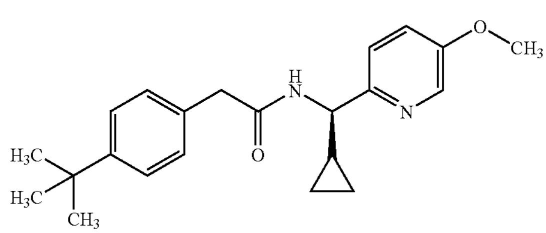 | 2-(4-tert-butylphenyl)-N-[(R)-cyclopropyl(5-methoxypyridin-2-yl)methyl]acetamide | 353.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 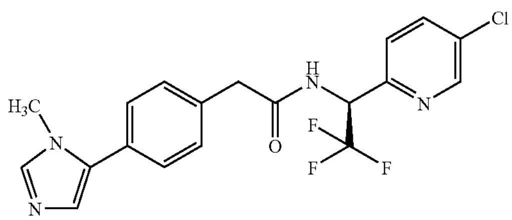 | N-[(1S)-1-(5-chloropyridin-2-yl)-2,2,2-trifluoroethyl]-2-[4-(1-methyl-1H-imidazol-5-yl)phenyl]acetamide | 409 |
| 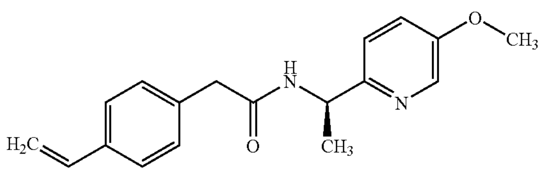 | 2-(4-vinylphenyl)-N-[(1R)-1-(5-methoxypyridin-2-yl)ethyl]acetamide | 297.1 |
| 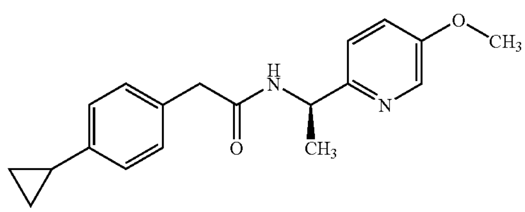 | 2-(4-cyclopropylphenyl)-N-[(1R)-1-(5-methoxypyridin-2-yl)ethyl]acetamide | 311.1 |
| 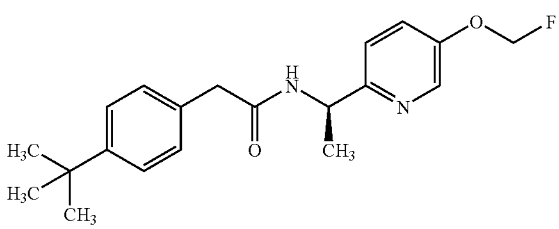 | 2-(4-tert-butylphenyl)-N-{(1R)-1-[5-(fluoromethoxy)pyridin-2-yl]ethyl}acetamide | 345.2 |
| 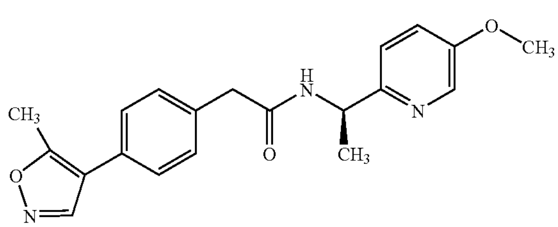 | N-[(1R)-1-(5-methoxypyridin-2-yl)ethyl]-2-[4-(5-methylisoxazol-4-yl)phenyl]acetamide | 352.1 |
| 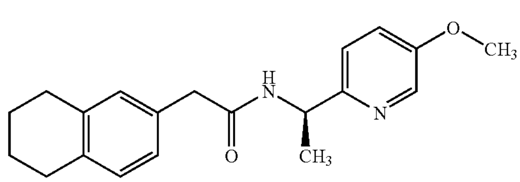 | N-[(1R)-1-(5-methoxypyridin-2-yl)ethyl]-2-(5,6,7,8-tetrahydronaphthalen-2-yl)acetamide | 325.1 |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| Structure | Name | M + 1 |
|---|---|---|
| 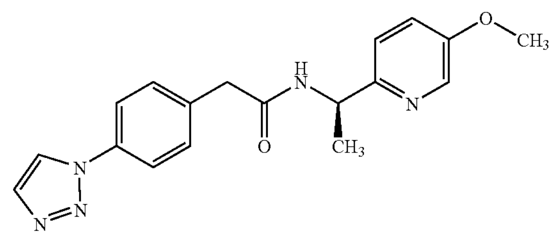 | N-[(1R)-1-(5-methoxypyridin-2-yl)ethyl]-2-[4-(1H-1,2,3-triazol-1-yl)phenyl]acetamide | 338.3 |
| 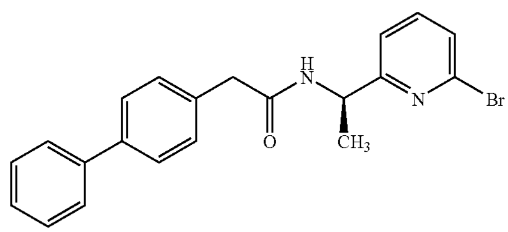 | 2-biphenyl-4-yl-N-[(1R)-1-(6-bromopyridin-2-yl)ethyl]acetamide | 396.1 |
| 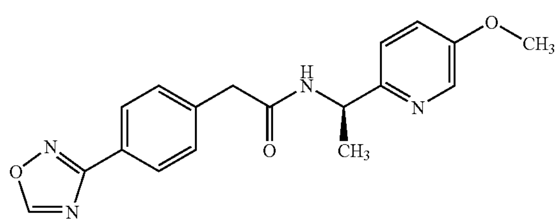 | N-[(1R)-1-(5-methoxypyridin-2-yl)ethyl]-2-[4-(1,2,4-oxadiazol-3-yl)phenyl]acetamide | 339.1 |
| 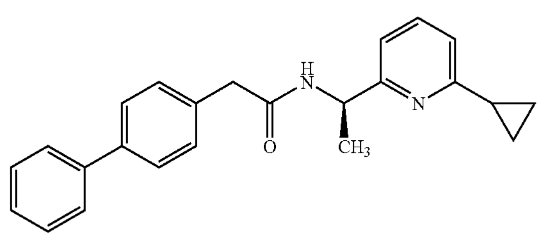 | 2-biphenyl-4-yl-N-[(1R)-1-(6-cyclopropylpyridin-2-yl)ethyl]acetamide | 357.1 |
| 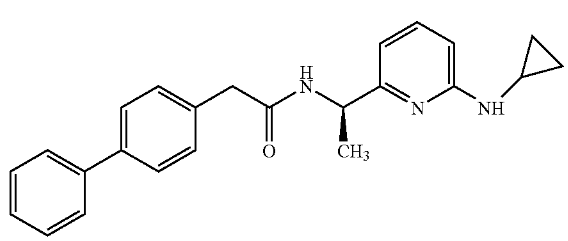 | 2-biphenyl-4-yl-N-{(1R)-1-[6-(cyclopropylamino)pyridin-2-yl]ethyl}acetamide | 372.1 |
| 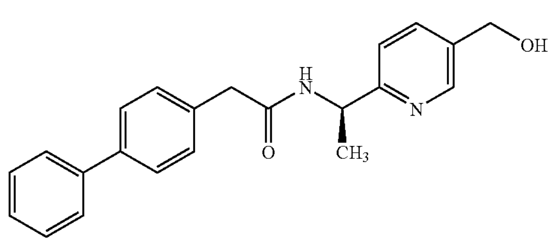 | 2-biphenyl-4-yl-N-{(1R)-1-[5-(hydroxymethyl)pyridin-2-yl]ethyl}acetamide | 347.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 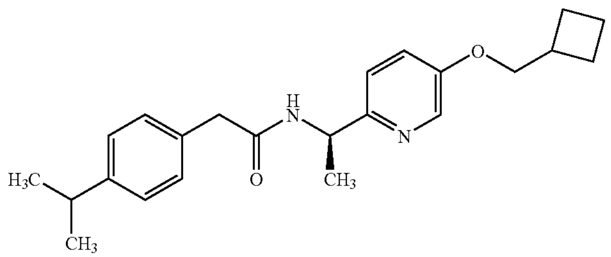 | N-{(1R)-1-[5-(cyclobutyl-methoxy)pyridin-2-yl]ethyl}-2-(4-isopropylphenyl)acetamide | 367.4 |
| 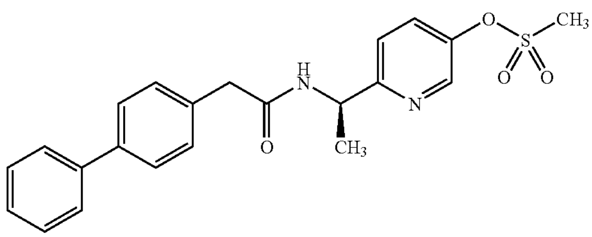 | 6-{(1R)-1-[(2-biphenyl-4-ylacetyl)amino]ethyl}pyridin-3-yl methanesulfonate | 411.1 |
| 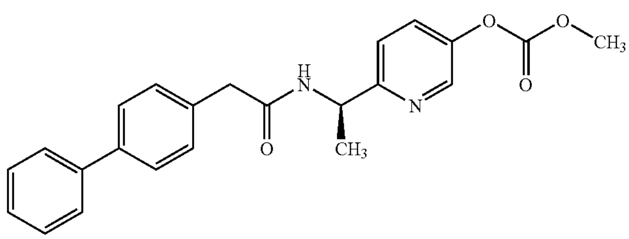 | 6-{(1R)-1-[(biphenyl-4-ylacetyl)amino]ethyl}pyridin-3-yl methyl carbonate | 391.1 |
| 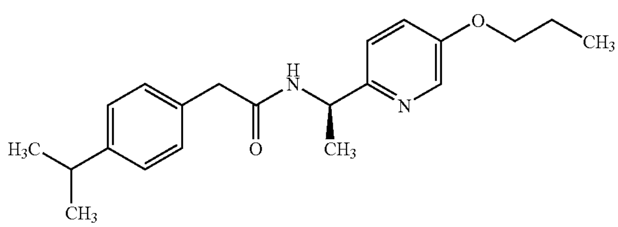 | 2-(4-isopropylphenyl)-N-[(1R)-1-(5-propoxypyridin-2-yl)ethyl]acetamide | 341.3 |
| 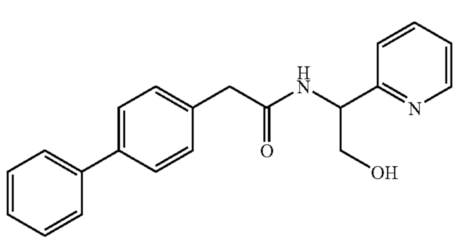 | 2-biphenyl-4-yl-N-(2-hydroxy-1-pyridin-2-ylethyl)acetamide | 333.3 |
| 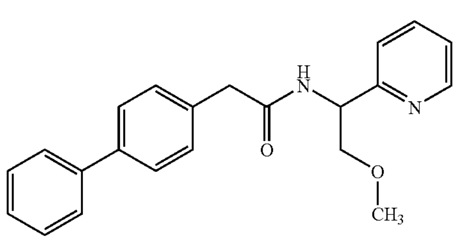 | 2-biphenyl-4-yl-N-(2-methoxy-1-pyridin-2-ylethyl)acetamide | 347.3 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 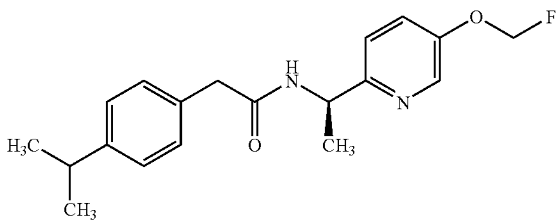 | 2-(4-isopropylphenyl)-N-[(1R)-1-(5-fluoromethoxypyridin-2-yl)ethyl]acetamide | 331.1 |
| 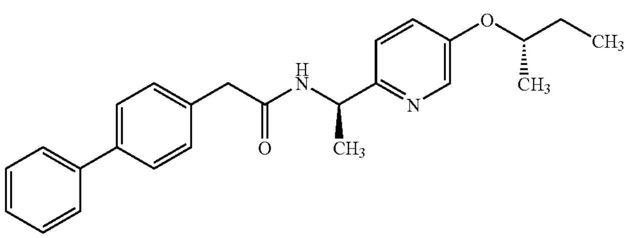 | 2-biphenyl-4-yl-N-[(1R)-1-(5-{[(1S)-1-methylpropyl]oxy}pyridin-2-yl)ethyl]acetamide | 389.2 |
| 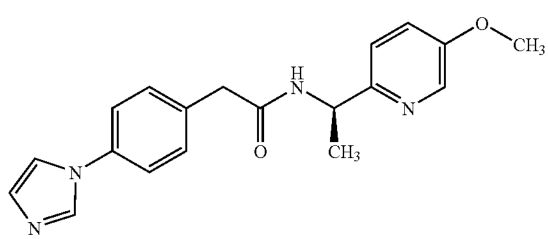 | 2-[4-(1H-imidazol-1-yl)phenyl]-N-[(1R)-1-(5-methoxypyridin-2-yl)ethyl]acetamide | 337.3 |
| 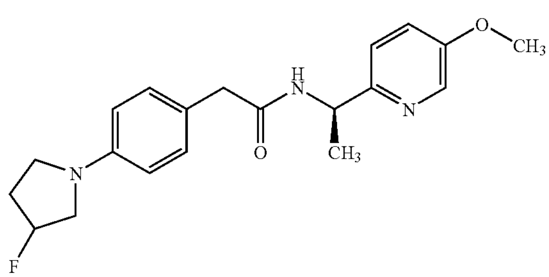 | 2-[4-(3-fluoropyrrolidin-1-yl)phenyl]-N-[(1R)-1-(5-methoxypyridin-2-yl)ethyl]acetamide | 358.3 |
| 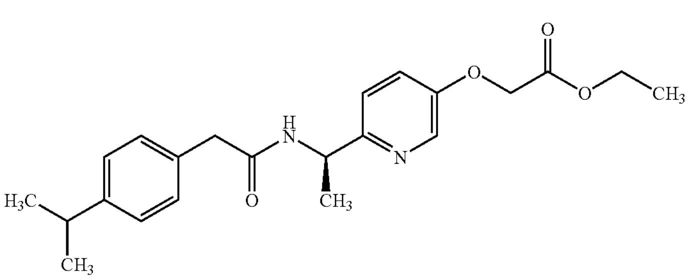 | ethyl {[6-((1R)-1-{[(4-isopropylphenyl)acetyl]amino}ethyl)pyridin-3-yl]oxy}acetate | 385.3 |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| Structure | Name | M + 1 |
|---|---|---|
| 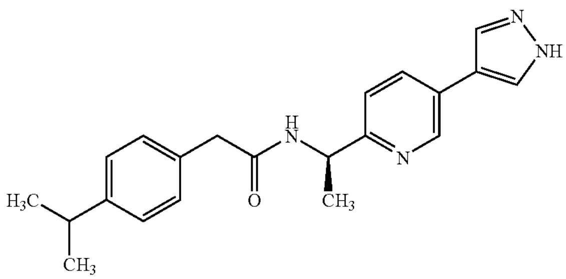 | 2-(4-isopropylphenyl)-N-{(1R)-1-[5-(1H-pyrazol-4-yl)pyridin-2-yl]ethyl}acetamide | 349.1 |
| 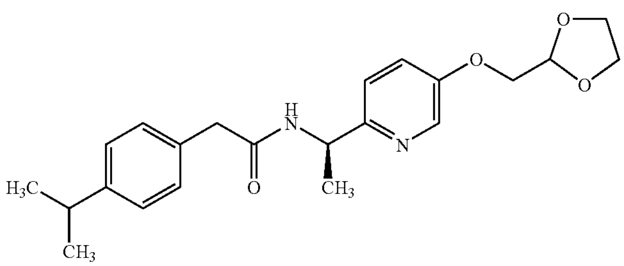 | N-{(1R)-1-{5-(1,3-dioxolan-2-ylmethoxy)pyridin-2-yl]ethyl}-2-(4-isopropylphenyl)acetamide | 385.4 |
| 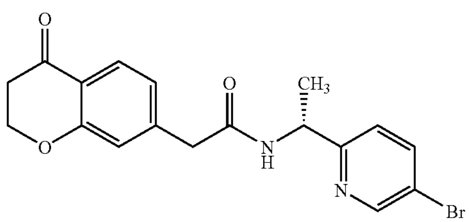 | N-[(1R)-1-(5-bromopyridin-2-yl)ethyl]-2-(4-oxo-3,4-dihydro-2H-chromen-7-yl)acetamide | 389 |
| 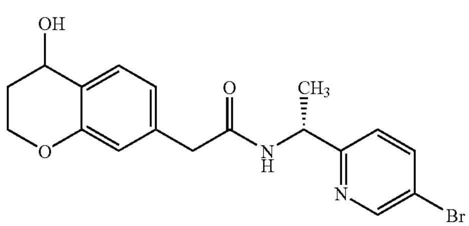 | N-[(1R)-1-(5-bromopyridin-2-yl)ethyl]-2-(4-hydroxy-3,4-dihydro-2H-chromen-7-yl)acetamide | 391 |
| 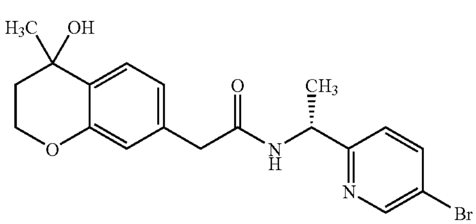 | N-[(1R)-1-(5-bromopyridin-2-yl)ethyl]-2-(4-hydroxy-4-methyl-3,4-dihydro-2H-chromen-7-yl)acetamide | 405 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 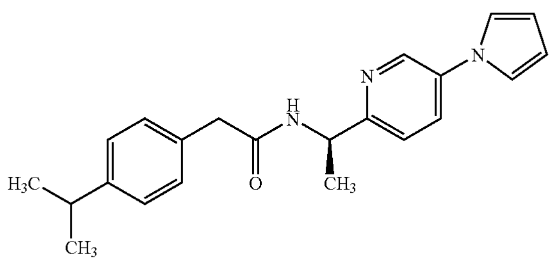 | 2-(4-isopropylphenyl)-N-{(1R)-1-[5-(1H-pyrrol-1-yl)pyridin-2-yl]ethyl}acetamide | 348.1 |
| 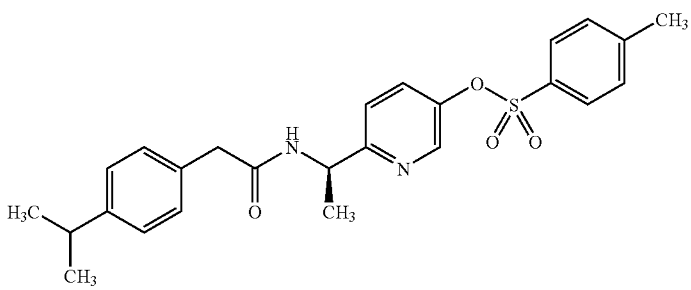 | 6-((1R)-1-{[2-(4-isopropylphenyl)-acetyl]amino}ethyl)pyridin-3-yl 4-methylbenzenesulfonate | 453.5 |
| 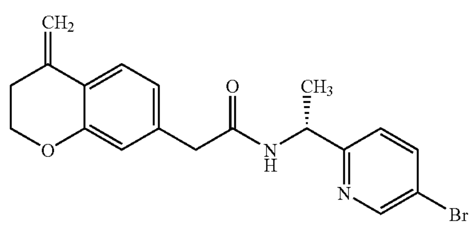 | N-[(1R)-1-(5-bromopyridin-2-yl)ethyl]-2-(4-methylene-3,4-dihydro-2H-chromen-7-yl)acetamide | 387 |
| 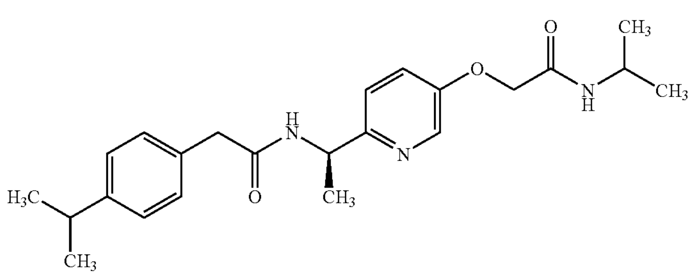 | N-((1R)-1-{5-[2-(isopropylamino)-2-oxoethoxy]pyridin-2-yl}ethyl)-2-(4-isopropylphenyl)acetamide | 398.4 |
| | N-[(1R)-1-(5-tert-butoxypyridin-2-yl)ethyl]-2-(4-isopropylphenyl)acetamide | 355.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 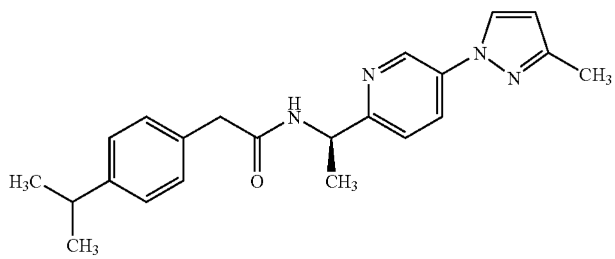 | 2-(4-isopropylphenyl)-N-{(1R)-1-[5-(3-methyl-1H-pyrazol-1-yl)pyridin-2-yl]ethyl}acetamide | 363.2 |
| 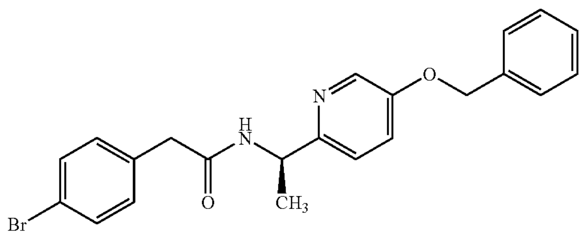 | N-{(1R)-1-[5-(benzyloxy)pyridin-2-yl]ethyl}-2-(4-bromophenyl)acetamide | 426.1 |
| | N-{(1R)-1-[5-(benzyloxy)pyridin-2-yl]ethyl}-2-[4-(1H-pyrrol-1-yl)phenyl]acetamide | 412.2 |
| 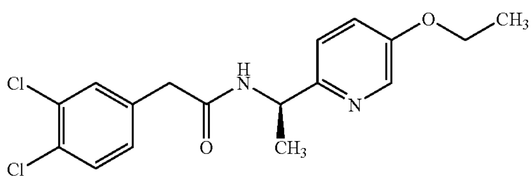 | 2-(3,4-dichlorophenyl)-N-[(1R)-1-(5-propylpyridin-2-yl)ethyl]acetamide | 351 |
| 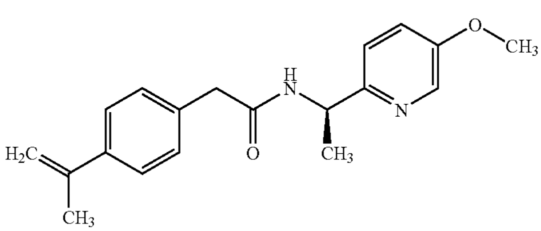 | 2-(4-isopropenylphenyl)-N-[(1R)-1-(5-methoxypyridin-2-yl)ethyl]acetamide | 311.3 |
| 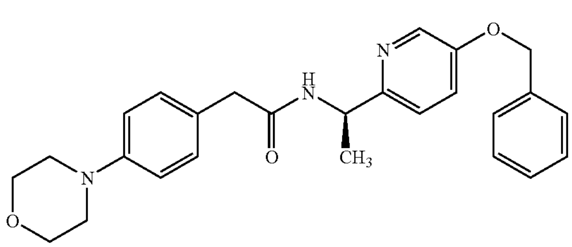 | N-{(1R)-1-[5-(benzyloxy)pyridin-2-yl]ethyl}-2-(4-morpholin-4-ylphenyl)acetamide | 432.2 |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| Structure | Name | M + 1 |
|---|---|---|
| 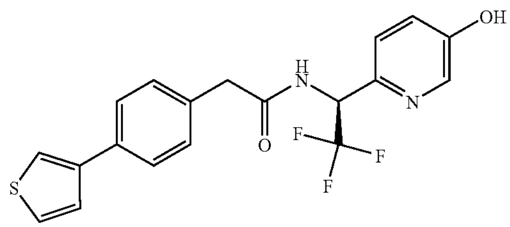 | 2-[4-(3-thienyl)phenyl]-N-{(1S)-2,2,2-trifluoro-1-(5-hydroxypyridin-2-yl)ethyl]acetamide | 393.0 |
| 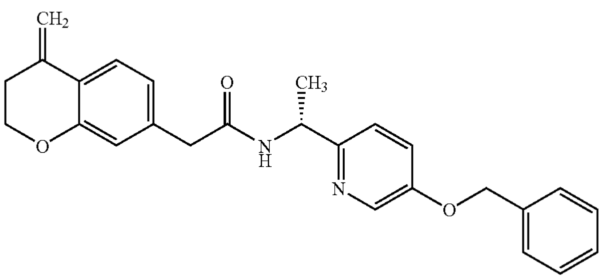 | N-[(1R)-1-(5-benzyloxypyridin-2-yl)ethyl]-2-(4-methylene-3,4-dihydro-2H-chromen-7-yl)acetamide | 415.2 |
| 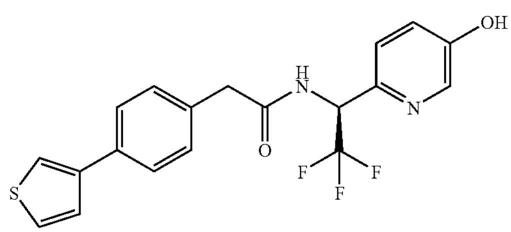 | 2-[4-(3-thienyl)phenyl]-N-[(1S)-2,2,2-trifluoro-1-(5-hydroxypyridin-2-yl)ethyl]acetamide | 393.1 |
| 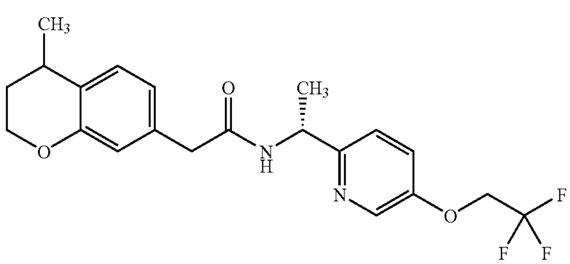 | 2-(4-methyl-3,4-dihydro-2H-chromen-7-yl)-N-{(1R)-1-[5-(2,2,2-trifluoroethoxy)pyridin-2-yl]ethyl}acetamide | 409.1 |
| 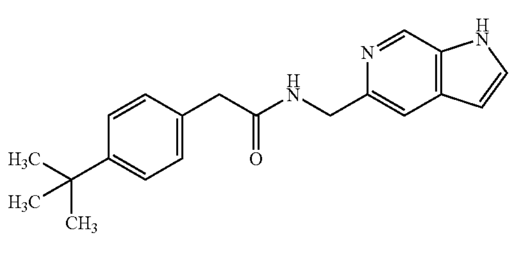 | 2-(4-tert-butylphenyl)-N-(1H-pyrrolo[2,3-c]pyridin-5-ylmethyl)acetamide | 322.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 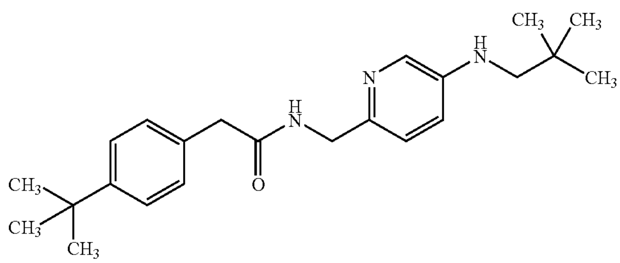 | 2-(4-tert-butylphenyl)-N-({5-[(3,3-dimethylpropyl)amino]pyridin-2-yl}methyl)acetamide | 368.3 |
| 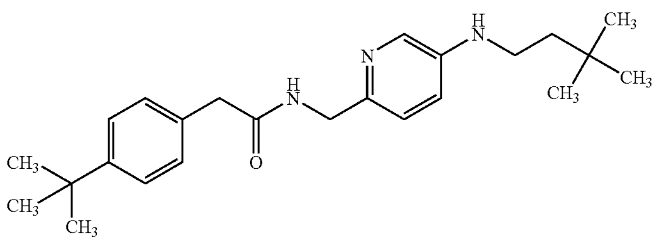 | 2-(4-tert-butylphenyl)-N-({5-[(3,3-dimethylbutyl)amino]pyridin-2-yl}methyl)acetamide | 382.3 |
| 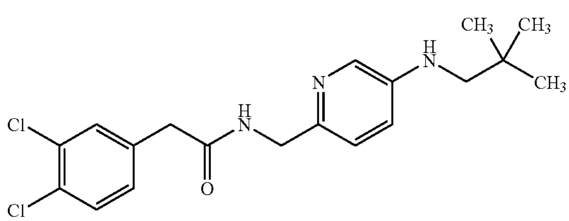 | 2-(3,4-dichlorophenyl)-N-({5-[(2,2-dimethylpropyl)amino]pyridin-2-yl}methyl)acetamide | 380.1 |
| 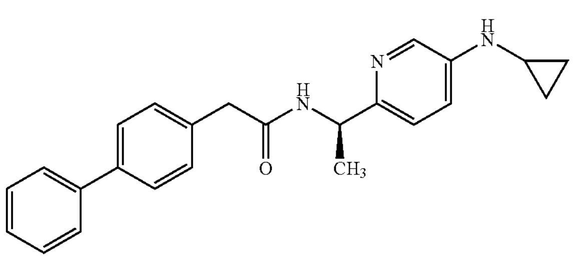 | 2-biphenyl-4-yl-N-{(1R)-1-[5-(cyclopropylamino)pyridin-2-yl]ethyl}acetamide | 372.3 |
| 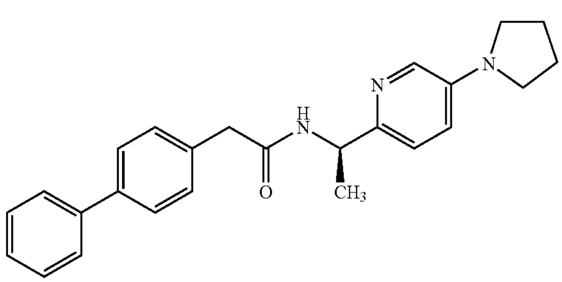 | 2-biphenyl-4-yl-N-[(1R)-1-(5-pyrrolidin-1-ylpyridin-2-yl)ethyl]acetamide | 386.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 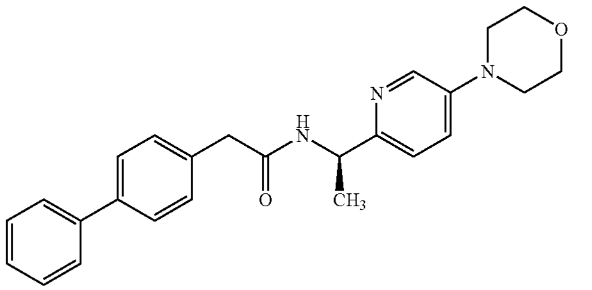 | 2-biphenyl-4-yl-N-[(1R)-1-(5-morpholin-4-ylpyridin-2-yl)ethyl]acetamide | 402.2 |
| 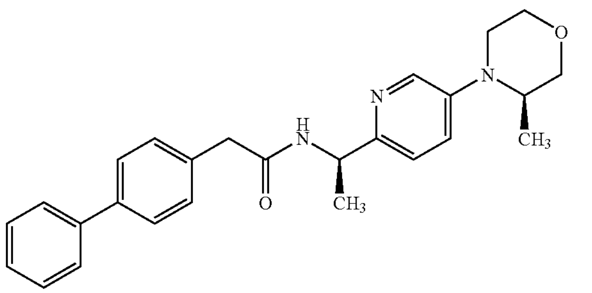 | 2-biphenyl-4-yl-N-((1R)-1-{5-[(3R)-3-methylmorpholin-4-yl]pyridin-2-yl}ethyl)acetamide | 416.2 |
| 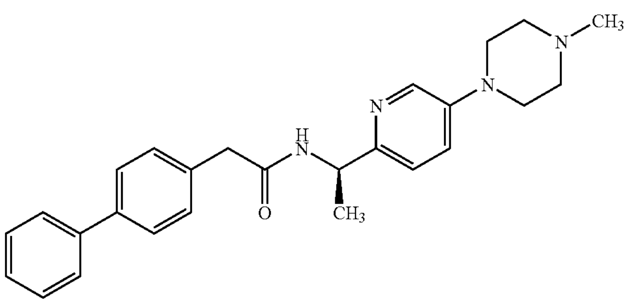 | 2-biphenyl-4-yl-N-{(1R)-1-[5-(4-methylpiperazin-1-yl)pyridin-2-yl]ethyl}acetamide | 415.3 |
| 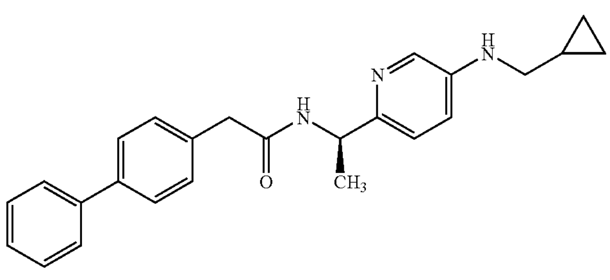 | 2-biphenyl-4-yl-N-{(1R)-1-[5-(cyclopropylmethylamino)pyridin-2-yl]ethyl}acetamide | 386.2 |
| 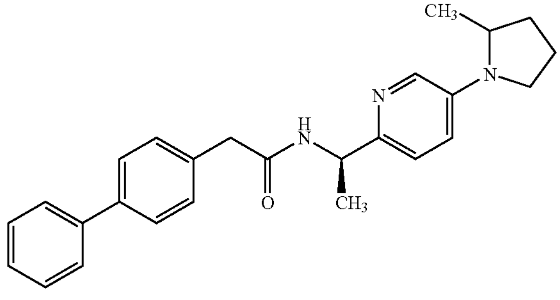 | 2-biphenyl-4-yl-N-{(1R)-1-[5-(2-methylpyrolidin-1-yl)pyridin-2-yl]ethyl}acetamide | 400.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 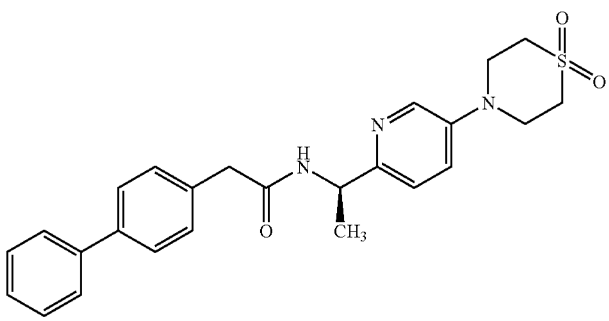 | 2-biphenyl-4-yl-N-{(1R)-1-[5-(1,1-dioxidothiomorpholin-4-yl)pyridin-2-yl]ethyl}acetamide | 450.2 |
| 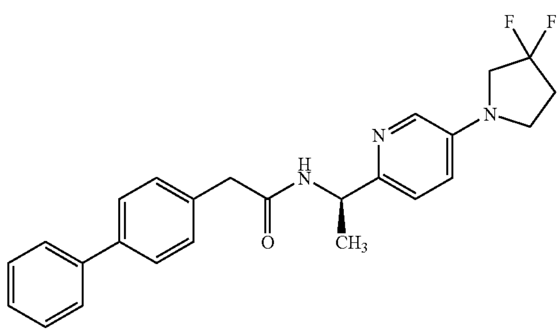 | 2-biphenyl-4-yl-N-{(1R)-1-[5-(3,3di-fluoropyrrolidin-1-yl)pyridin-2-yl]ethyl}acetamide | 422.2 |
| 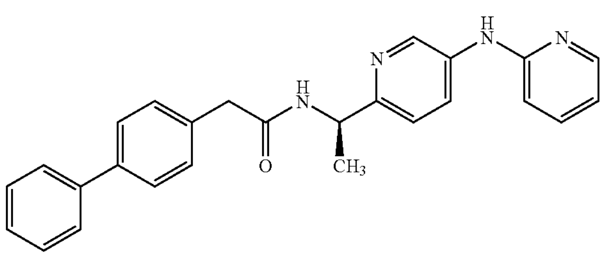 | 2-biphenyl-4-yl-N-{(1R)-1-[5-(pyridin-2-ylamino)pyridin-2-yl]ethyl}acetamide | 409.2 |
| 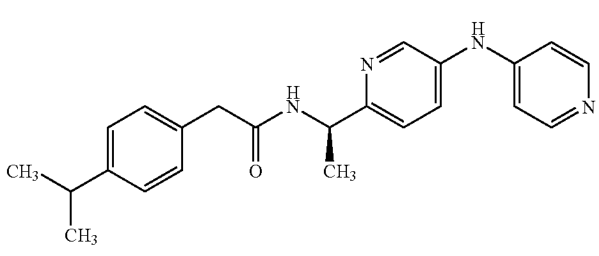 | 2-(4-isopropylphenyl)-N-{(1R)-1-[5-pyridin-4-ylamino)pyridin-2-yl]ethyl}acetamide | 375.2 |
| 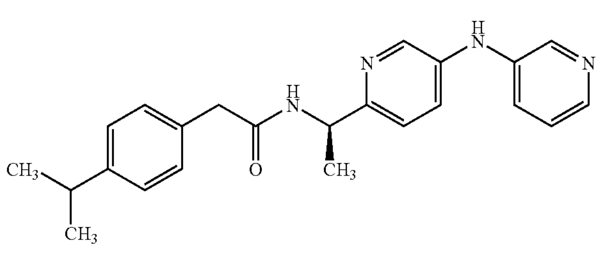 | 2-(4-isopropylphenyl)-N-{(1R)-1-[5-(pyridin-3-ylamino)pyridin-2-yl]ethyl}acetamide | 375.2 |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| Structure | Name | M + 1 |
|---|---|---|
| 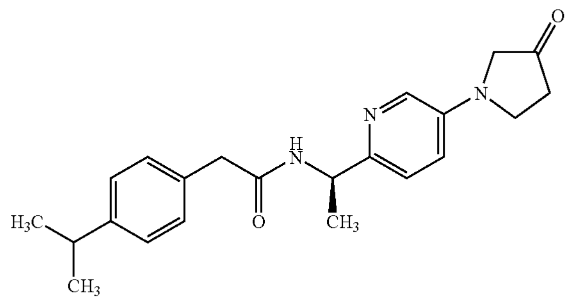 | 2-(4-isopropylphenyl)-N-{(1R)-1-[5-3-oxopyrrolidin-1-yl)pyridin-2-yl]ethyl}acetamide | 366.1 |
| 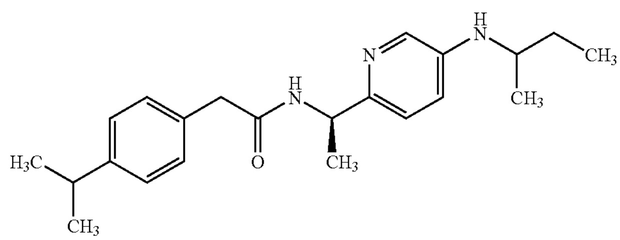 | N-{(1R)-1-[5-(sec-butylamino)pyridin-2-yl]ethyl}-2-(4-isopropylphenyl)acetamide | 354.2 |
| 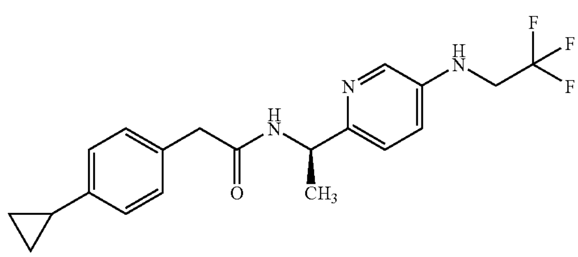 | 2-(4-cyclopropylphenyl)-N-((1R)-1-{5-[(2,2,2-trifluoroethyl)amino]pyridin-2-yl}ethyl)acetamide | 378.1 |
| 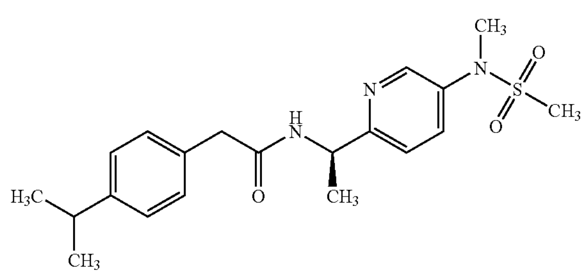 | 2-(4-isopropylphenyl)-N-((1R)-1-{5-[methyl(methylsulfonyl)amino]pyridin-2-yl}ethyl)acetamide | 390 |
| 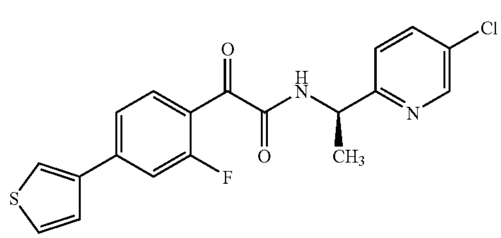 | N-[(1R)-1-(5-chloropyridin-2-yl)ethyl]-2-[2-fluoro-4-(3-thienyl)phenyl]-2-oxoacetamide | 389.0 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 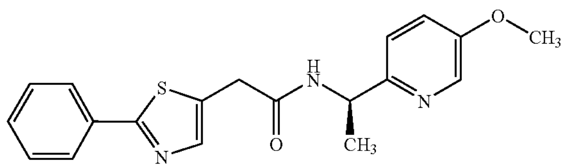 | N-[(1R)-1-(5-methoxypyridin-2-yl)ethyl]-2-(2-phenyl-1,3-thiazol-5-yl)acetamide | 354.1 |
| 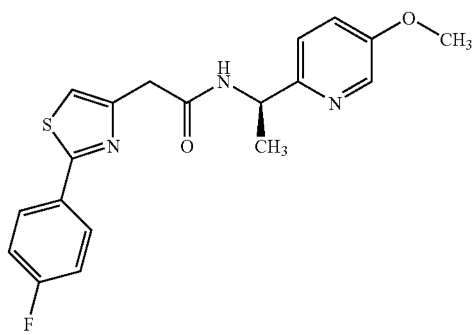 | 2-[2-(4-fluorophenyl)-1,3-thiazol-4-yl]-N-[(1R)-1-(5-methoxypyridin-2-yl)ethyl]acetamide | 372 |
| 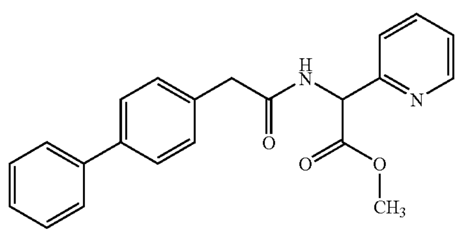 | methyl [(biphenyl-4-ylacetyl)amino]-(pyridin-2-yl)acetate | 361.3 |
| 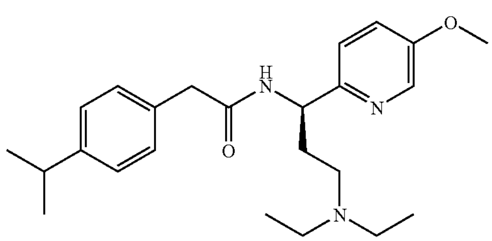 | N-[(1R)-3-(diethylamino)-1-(5-methoxypyridin-2-yl)propyl]-2-(4-isopropylphenyl)acetamide | 398.5 |
| 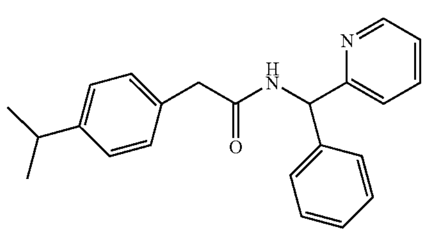 | 2-(4-isopropylphenyl)-N-[phenyl(pyridin-2-yl)methyl]acetamide | 345.1 |
| 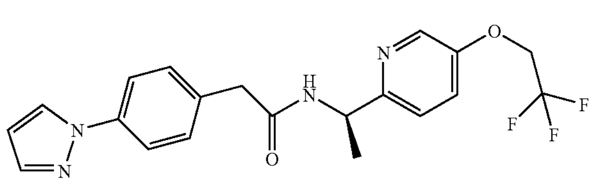 | 2-[4-(1H-pyrazol-1-yl)phenyl]-N-{(1R)-1-[5-(2,2,2-trifluoroethoxy)pyridin-2-yl]ethyl}acetamide | 405.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 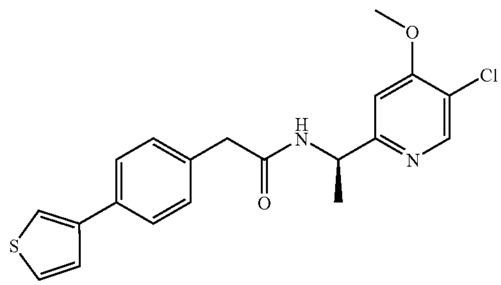 | N-[(1R)-1-(5-chloro-4-methoxypyridin-2-yl)ethyl]-2-[4-(3-thienyl)phenyl]acetamide | 387.0 |
| 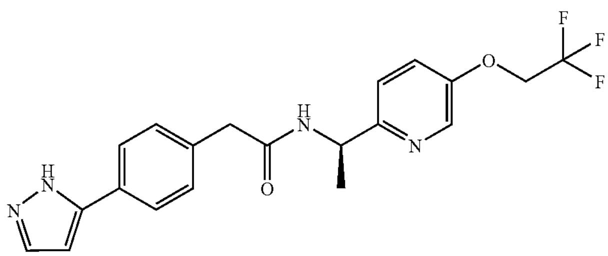 | 2-[4-(1H-pyrazol-5-yl)phenyl]-N-{(1R)-1-[5-(2,2,2-trifluoroethoxy)pyridin-2-yl]ethyl}acetamide | 405.1 |
| 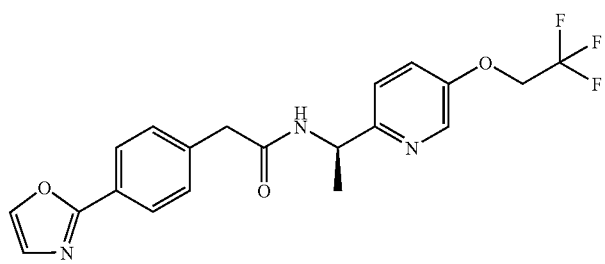 | 2-[4-(1,3-oxazol-2-yl)phenyl]-N-{(1R)-1-[5-(2,2,2-trifluoroethoxy)pyridin-2-yl]ethyl}acetamide | 406.1 |
| 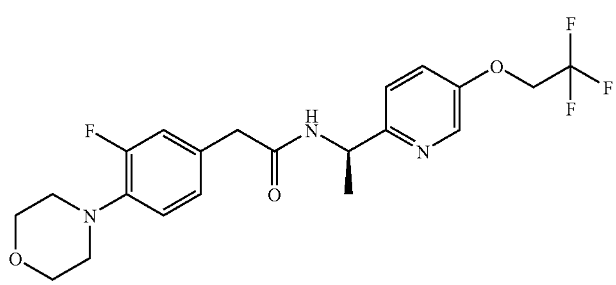 | 2-(3-fluoro-4-morpholin-4-ylphenyl)-N-{(1R)-1-[5-(2,2,2-trifluoroethoxy)pyridin-2-yl]ethyl}acetamide | 442.1 |
| 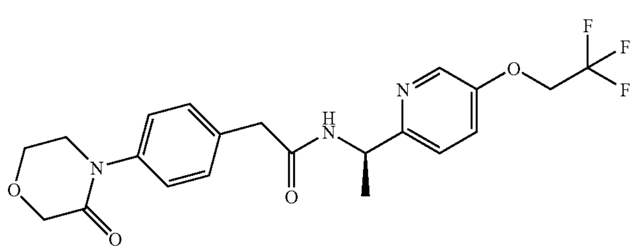 | N-{(1R)-1-[5-(2,2-difluoropropoxy)pyridin-2-yl]ethyl}-2-[4-(3-oxomorpholin-4-yl)phenyl]acetamide | 438.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 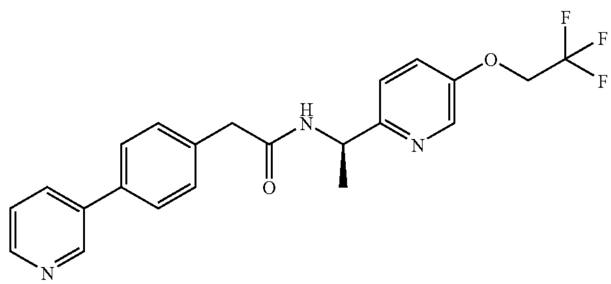 | 2-(4-pyridin-3-ylphenyl)-N-{(1R)-1-[5-(2,2,2-trifluoroethoxy)pyridin-2-yl]ethyl}acetamide | 416.1 |
| 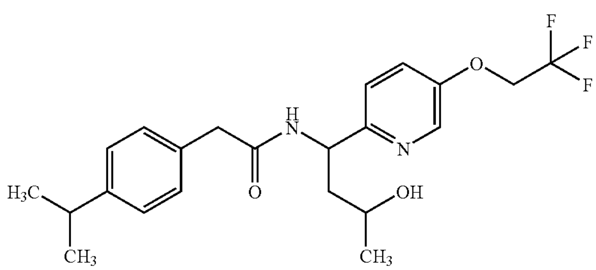 | N-{3-hydroxy-1-[5-(2,2,2-trifluoroethoxy)pyridin-2-yl]butyl}-2-(4-isopropylphenyl)acetamide | 425.5 |
| 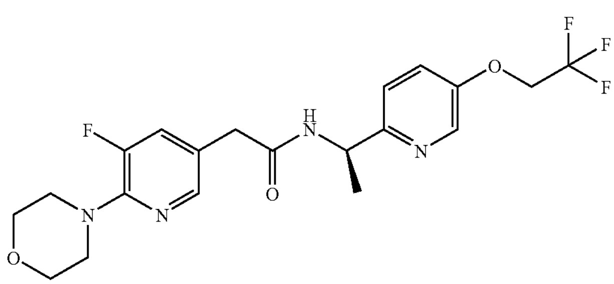 | 2-(5-fluoro-6-morpholin-4-ylpyridin-3-yl)-N-{(1R)-1-[5-(2,2,2-trifluoroethoxy)pyridin-2-yl]ethyl}acetamide | 443.1 |
| 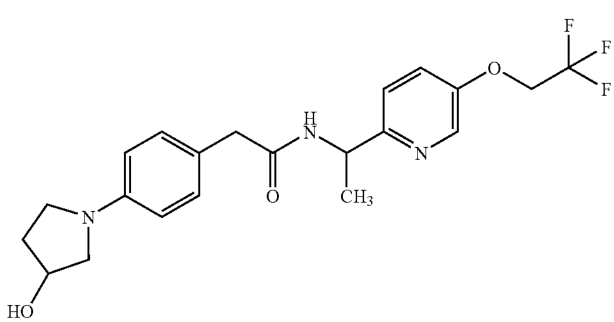 | 2-[4-(3-hydroxypyrrolidin-1-yl)phenyl]-N-{1-[5-(2,2,2-trifluoroethoxy)pyridin-2-yl]ethyl}acetamide | 424.4 |
| 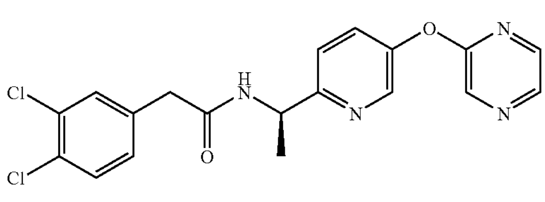 | 2-(3,4-dichlorophenyl)-N-{(1R)-1-[5-(pyrazin-2-yloxy)pyridin-2-yl]ethyl}acetamide | 403 |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| Structure | Name | M + 1 |
|---|---|---|
| 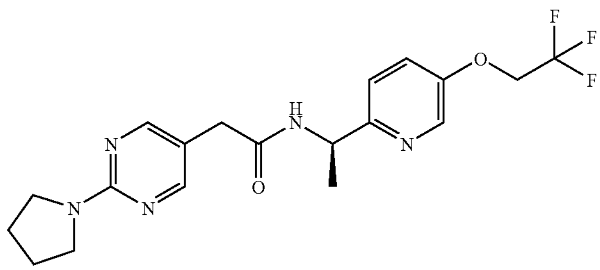 | 2-(2-pyrrolidin-1-ylpyrimidin-5-yl)-N-{(1R)-1-[5-(2,2,2-trifluoroethoxy)pyridin-2-yl]ethyl}acetamide | 410.4 |
| 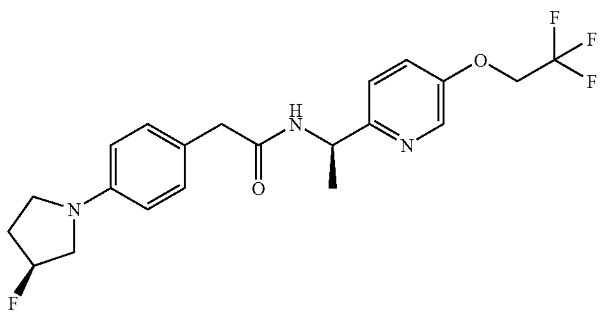 | 2-{4-[(3S)-3-fluoropyrrolidin-1-yl]phenyl}-N-{(1R)-1-{5-(2,2,2-trifluoroethoxy)pyridin-2-yl]ethyl}acetamide | 426.4 |
| 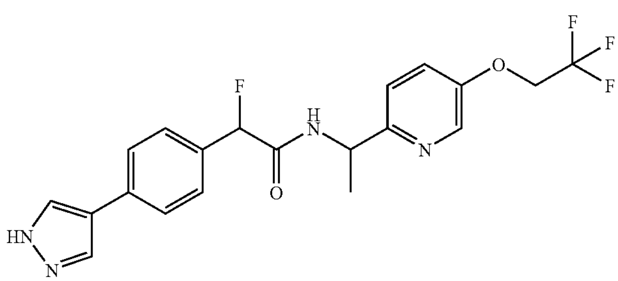 | 2-fluoro-2-[4-(1H-pyrazol-4-yl)phenyl]-N-{1-[5-(2,2,2-trifluoroethoxy)pyridin-2-yl]ethyl}acetamide | 423.1 |
| 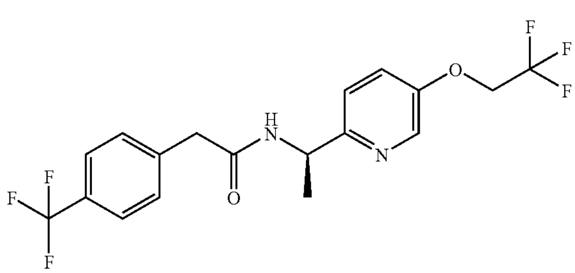 | N-{(1R)-1-[5-(2,2,2-trifluoroethoxy)pyridin-2-yl]ethyl}-2-[4-(trifluoromethyl)phenyl]acetamide | 407.4 |
| 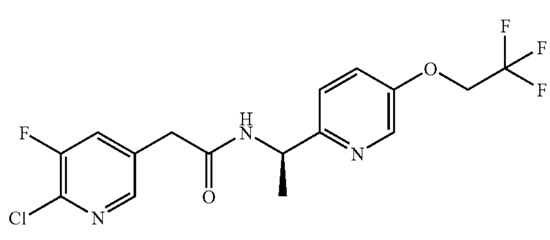 | 2-(6-chloro-5-fluoropyridin-3-yl)-N-{(1R)-1-[5-(2,2,2-trifluoroethoxy)pyridin-2-yl]ethyl}acetamide | 392.3 |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| Structure | Name | M + 1 |
|---|---|---|
| 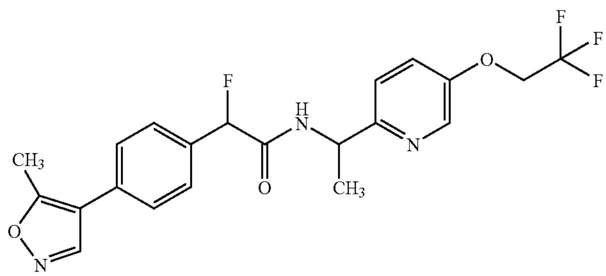 | 2-fluoro-2-[4-(5-methylisoxazol-4-yl)phenyl]-N-{1-[5-(2,2,2-trifluoroethoxy)pyridin-2-yl]ethyl}acetamide | 438.1 |
| 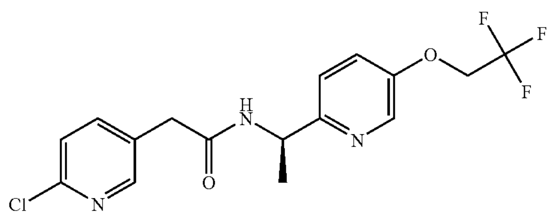 | 2-(6-chloropyridin-3-yl)-N-{(1R)-1-[5-(2,2,2-trifluoroethoxy)pyridin-2-yl]ethyl}acetamide | 374.1 |
| 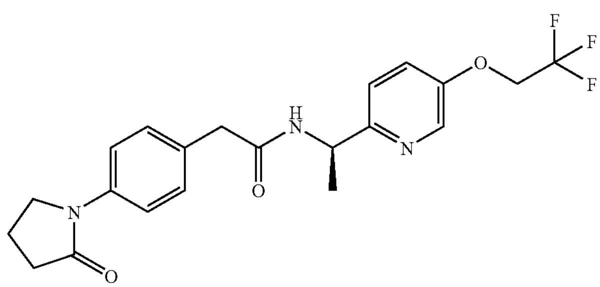 | 2-[4-(2-oxopyrrolidin-1-yl)phenyl]-N-{(1R)-1-[5-(2,2,2-trifluoroethoxy)pyridin-2-yl]ethyl}acetamide | 422.5 |
| 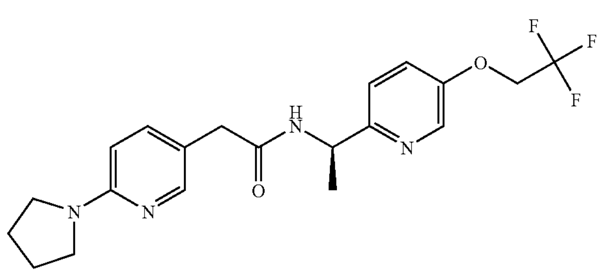 | 2-(6-pyrrolidin-1-ylpyridin-3-yl)-N-{(1R)-1-[5-(2,2,2-trifluoroethoxy)pyridin-2-yl]ethyl}acetamide | 409.2 |
| 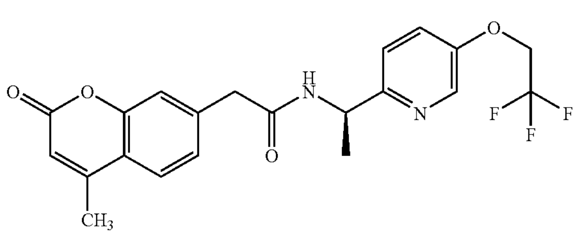 | 2-(4-methyl-2-oxo-2H-chromen-7-yl)-N-{(1R)-1-[5-(2,2,2-trifluoroethoxy)pyridin-2-yl]ethyl}acetamide | 421.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 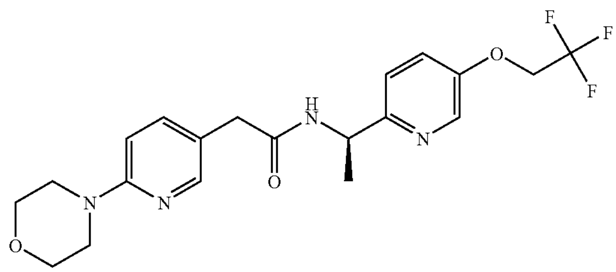 | 2-(6-morpholin-4-ylpyridin-3-yl)-N-{(1R)-1-[5-(2,2,2-trifluoroethoxy)pyridin-2-yl]ethyl}acetamide | 425.1 |
| 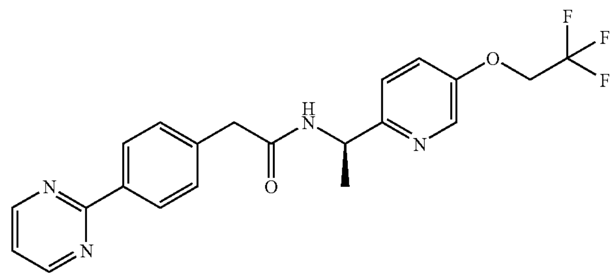 | 2-(4-pyrimidin-2-ylphenyl)-N-{(1R)-1-[5-(2,2,2-trifluoroethoxy)pyridin-2-yl]ethyl}acetamide | 417.1 |
| 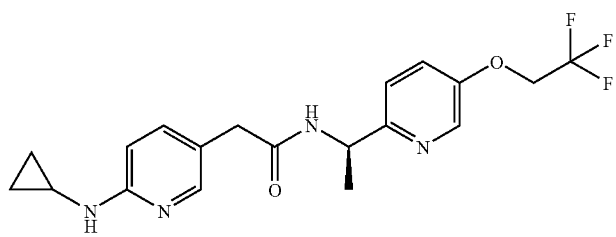 | 2-[6-(cyclopropylamino)pyridin-3-yl]-N-{(1R)-1-[5-(2,2,2-trifluoroethoxy)pyridin-2-yl]ethyl}acetamide | 395.1 |
| 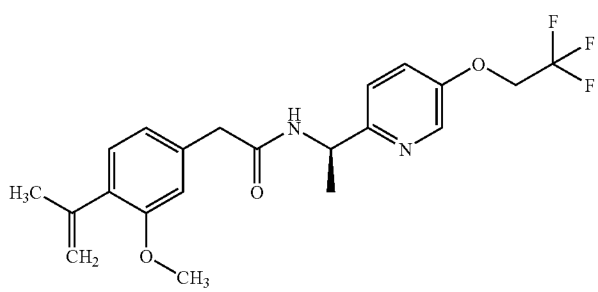 | 2-(4-isopropenyl-3-methoxyphenyl)-N-{(1R)-1-[5-(2,2,2-trifluoroethoxy)pyridin-2-yl]ethyl}acetamide | 409.1 |
| 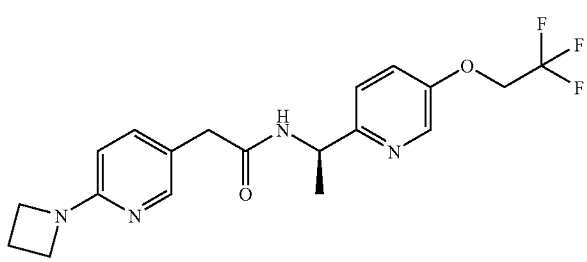 | 2-(6-azetidin-1-ylpyridin-3-yl)-N-{(1R)-1-[5-(2,2,2-trifluoroethoxy)pyridin-2-yl]ethyl}acetamide | 395.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 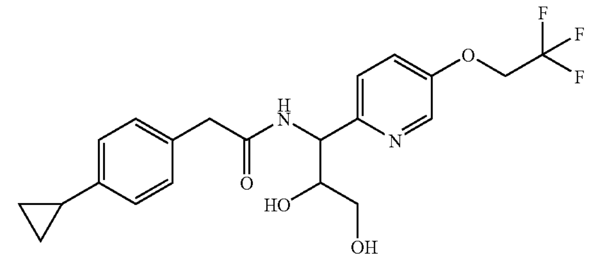 | 2-(4-cyclopropylphenyl)-N-{2,3-dihydroxy-1-[5-(2,2,2-trifluoroethoxy)pyridin-2-yl]propyl}acetamide | 425.1 |
| 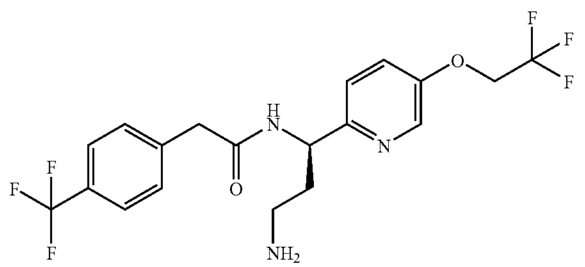 | N-{(1R)-3-amino-1-[5-(2,2,2-trifluoroethoxy)pyridin-2-yl]propyl}-2-[4-(trifluoromethyl)phenyl]acetamide | 436 |
| 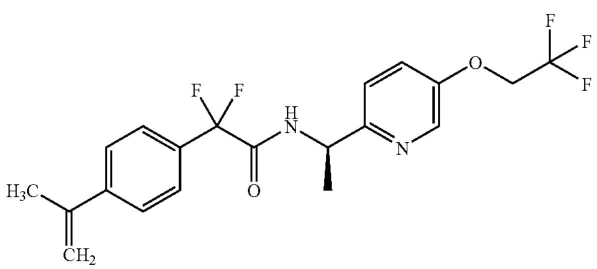 | 2,2-difluoro-2-(4-isopropenylphenyl)-N-{(1R)-1-[5-(2,2,2-trifluoroethoxy)pyridin-2-yl]ethyl}acetamide | 415.1 |
| 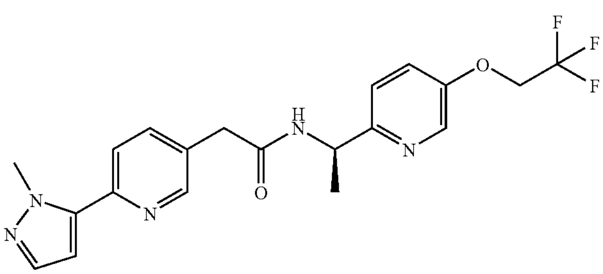 | 2-[6-(1-methyl-1H-pyrazol-5-yl)pyridin-3-yl]-N-{(1R)-1-[5-(2,2,2-trifluoroethoxy)pyridin-2-yl]ethyl}acetamide | 420.1 |
| 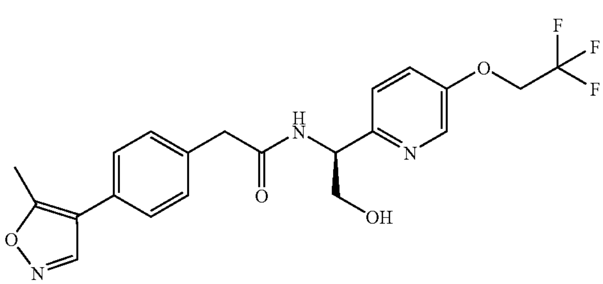 | N-{(1S)-2-hydroxy-1-[5-(2,2,2-trifluoroethoxy)pyridin-2-yl]ethyl}-2-[4-(5-methylisoxazol-4-yl)phenyl]acetamide | 436.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 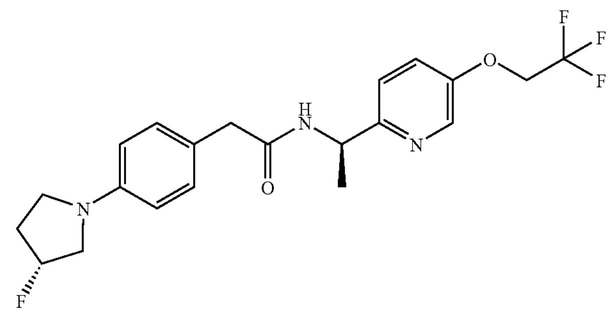 | 2-{4-[(3R)-3-fluoropyrrolidin-1-yl]phenyl}-N-{(1R)-1-[5-(2,2,2-trifluoroethoxy)pyridin-2-yl]ethyl) acetamide | 426.1 |
| 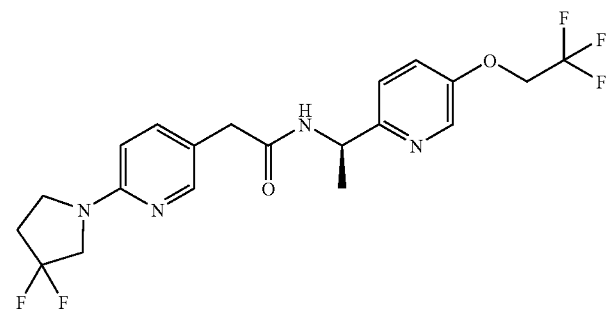 | 2-[6-(3,3-difluoropyrrolidin-1-yl)pyridin-3-yl]-N-{(1R)-1-[5-(2,2,2-trifluoroethoxy)pyridin-2-yl]ethyl}acetamide | 445.1 |
| 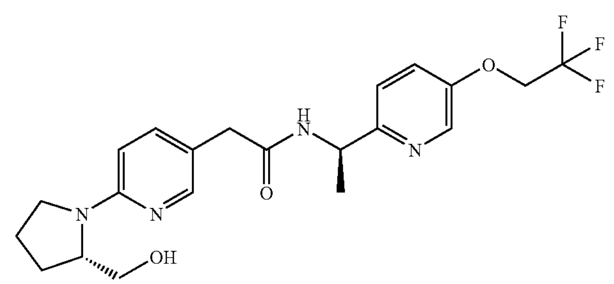 | 2-{6-[(2S)-2-(hydroxymethyl)pyrrolidin-1-yl]pyridin-3-yl}-N-{(1R)-1-[5-(2,2,2-trifluoroethoxy)pyridin-2-yl]ethyl}acetamide | 439.3 |
| 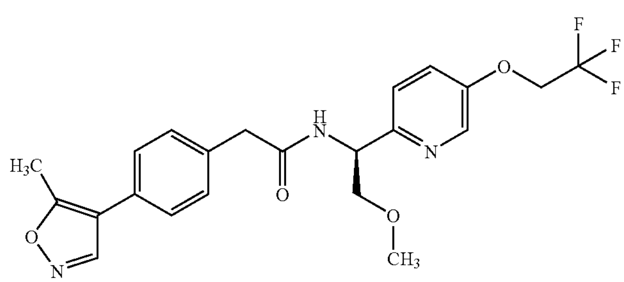 | N-{(1S)-2-methoxy-1-[5-(2,2,2-trifluoroethoxy)pyridin-2-yl]ethyl}-2-[4-(5-methylisoxazol-4-yl)phenyl]acetamide | 450.1 |
| 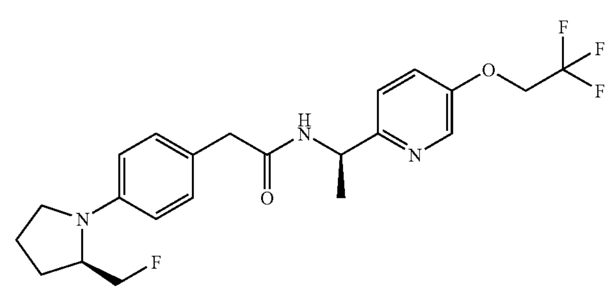 | 2-{4-[(2R)-2-(fluoromethyl)pyrrolidin-1-yl]phenyl}-N-{(1R)-1-[5-(2,2,2-trifluoroethoxy)pyridin-2-yl]ethyl)acetamide | 440.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 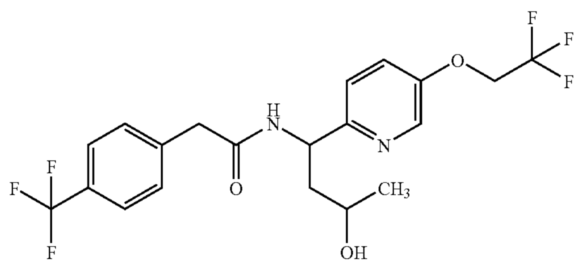 | N-{3-hydroxy-1-[5-(2,2,2-trifluoroethoxy)pyridin-2-yl]butyl}-2-[4-(trifluoromethyl)phenyl]acetamide | 451 |
| 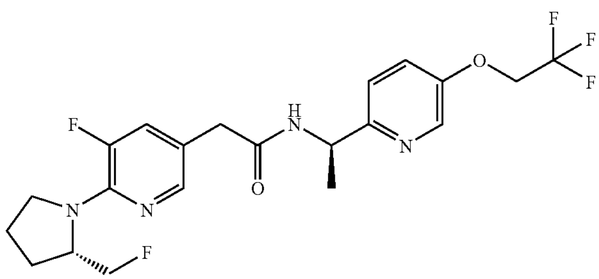 | 2-{5-fluoro-6-[(2S)-2-(fluoromethyl)pyrrolidin-1-yl]pyridin-3-yl}-N-{(1R)-1-[5-(2,2,2-trifluoroethoxy)pyridin-2-yl]ethyl}acetamide | 459.1 |
| 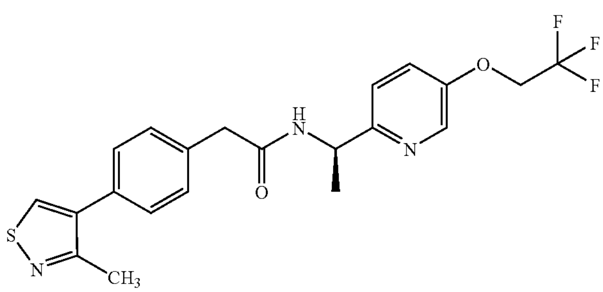 | 2-[4-(3-methylisothiazol-4-yl)phenyl]-N-{(1R)-1-[5-(2,2,2-trifluoroethoxy)pyridin-2-yl]ethyl}acetamide | 436.1 |
| 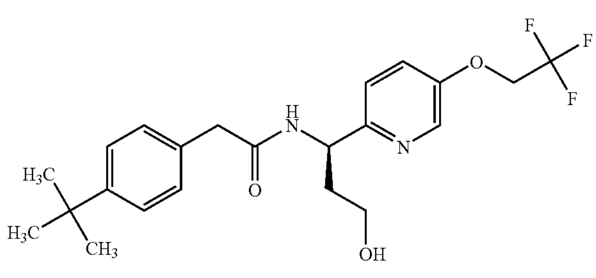 | 2-(4-tert-butylphenyl)-N-{(1R)-3-hydroxy-1-[5-(2,2,2-trifluoroethoxy)pyridin-2-yl]propyl}acetamide | 424.9 |
| 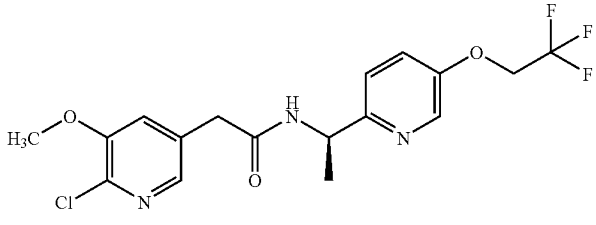 | 2-(6-chloro-5-methoxypyridin-3-yl)-N-{(1R)-1-[5-(2,2,2-trifluoroethoxy)pyridin-2-yl]ethyl}acetamide | 403.9 |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| Structure | Name | M + 1 |
|---|---|---|
| 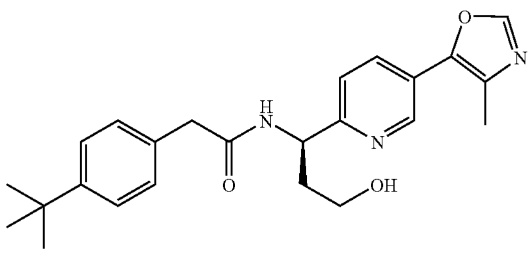 | 2-(4-tert-butylphenyl)-N-{(1R)-3-hydroxy-1-[5-(4-methyl-1,3-oxazol-5-yl)pyridin-2-yl]propyl}acetamide | 408.2 |
| 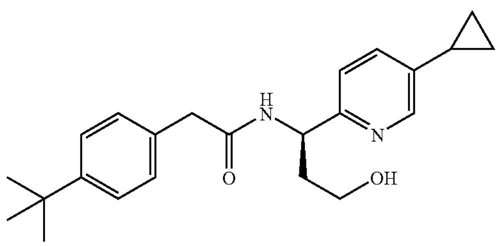 | 2-(4-tert-butylphenyl)-N-[(1R)-1-(5-cyclopropylpyridin-2-yl)-3-hydxoxypropyl]acetamide | 367.2 |
| 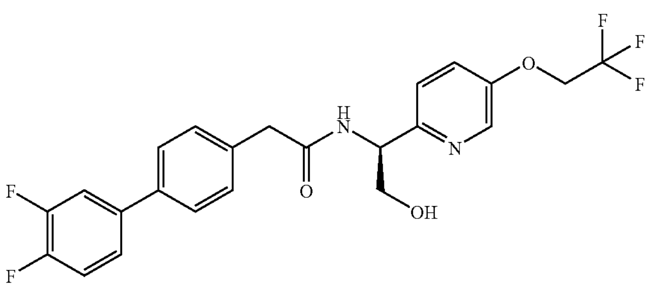 | 2-(3',4'-difluorobiphenyl-4-yl)-N-{(1S)-2-hydroxy-1-[5-(2,2,2-trifluoroethoxy)pyridin-2-yl]ethyl}acetamide | 467.1 |
| 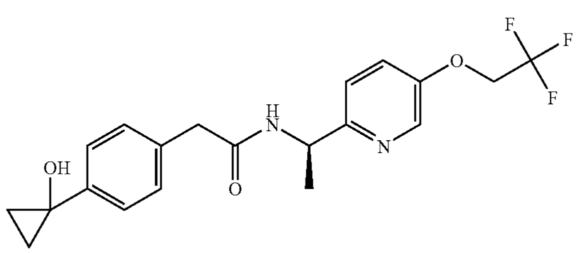 | 2-[4-{1-hydroxycyclopropyl)phenyl]-N-{(1R)-1-[5-(2,2,2-trifluoroethoxy)pyridin-2-yl]ethyl}acetamide | 395.0 |
| 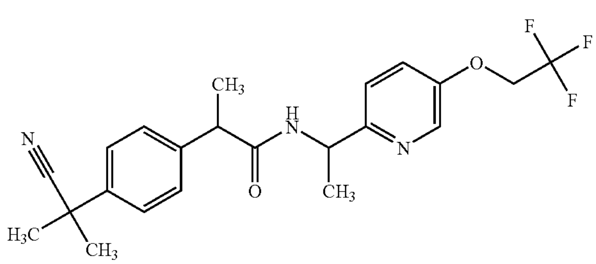 | 2-[4-(1-cyano-1-methylethyl)phenyl]-N-{1-[5-(2,2,2-trifluoroethoxy)pyridin-2-yl]ethyl}propanamide | 420 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 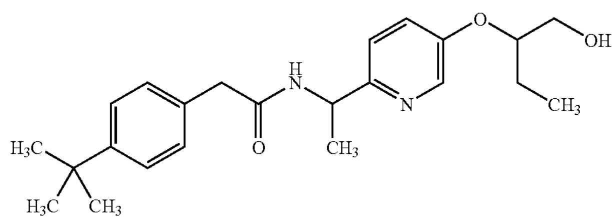 | 2-(4-tert-butylphenyl)-N-(1-{5-[1-(hydroxymethyl)propoxy]pyridin-2-yl}ethyl)acetamide | 385.2 |
| 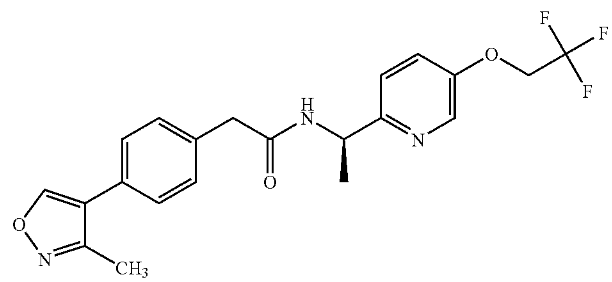 | 2-[4-(3-methylisoxazol-4-yl)phenyl]-N-{(1R)-1-[5-(2,2,2-trifluoroethoxy)pyridin-2-yl]ethyl}acetamide | 420.1 |
| 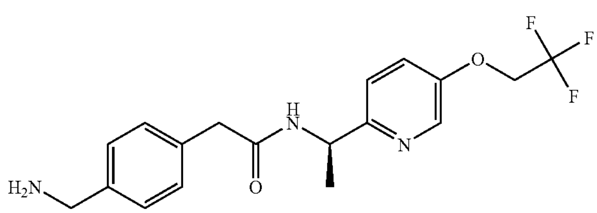 | 2-[4-(aminomethyl)phenyl]-N-{(1R)-1-[5-(2,2,2-trifluoroethoxy)pyridin-2-yl]ethyl}acetamide | 367.9 |
| 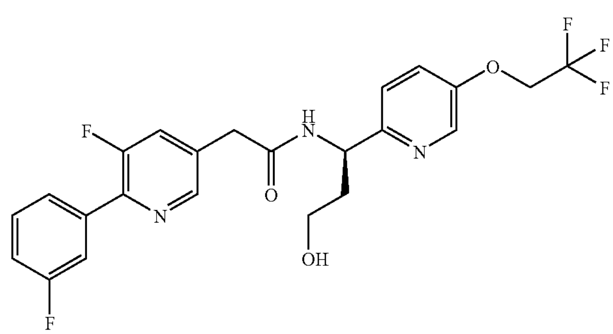 | 2-[5-fluoro-6-(3-fluorophenyl)pyridin-3-yl]-N-{(1R)-3-hydroxy-1-{5-(2,2,2-trifluoroethoxy)pyridin-2-yl]propyl}acetamide | 481.8 |
| 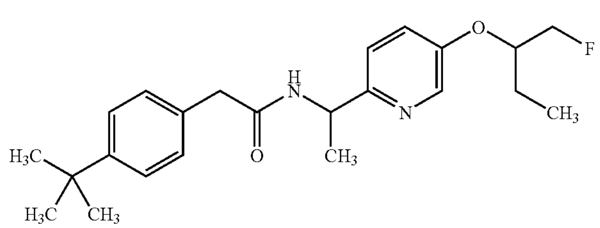 | 2-(4-tert-butylphenyl)-N-(1-{5-[1-(fluoromethyl)propoxy]pyridin-2-yl}ethyl)acetamide | 387.2 |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| Structure | Name | M + 1 |
|---|---|---|
| 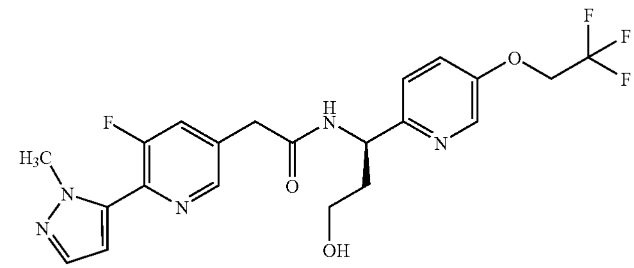 | 2-[5-fluoro-6-(1-methyl-1H-pyrazol-5-yl)pyridin-3-yl]-N-{(1R)-3-hydroxy-1-[5-(2,2,2-trifluoroethoxy)pyridin-2-yl]propyl}acetamide | 468 |
| 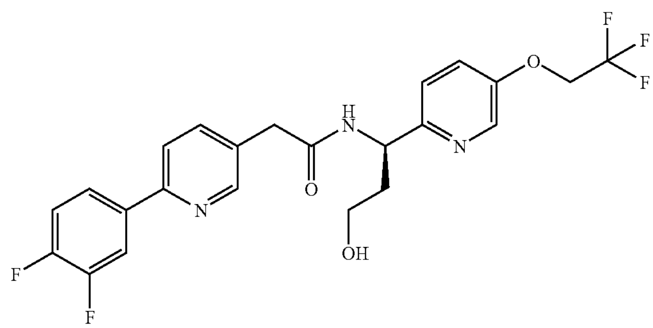 | 2-[6-(3,4-difluorophenyl)pyridin-3-yl]-N-{(1R)-3-hydroxy-1-[5-(2,2,2-trifluoroethoxy)pyridin-2-yl]propyl}acetamide | 481.9 |
| 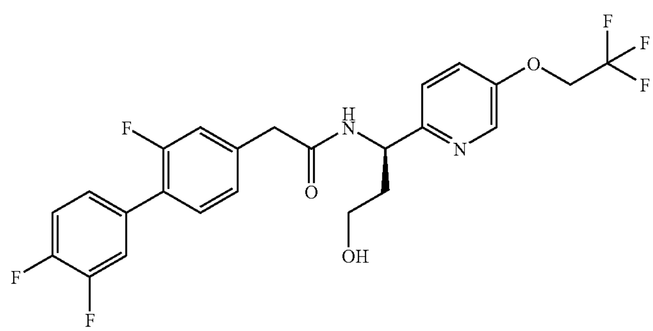 | N-{(1R)-3-hydroxy-1-{5-(2,2,2-trifluoroethoxy)pyridin-2-yl]propyl}-2-(2,3',4'-trifluorobiphenyl-4-yl)acetamide | 499 |
| 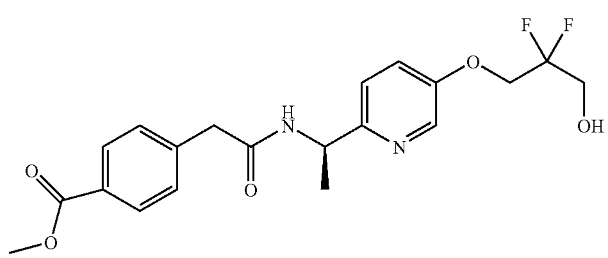 | methyl 4-[2-({(1R)-1-{5-(2,2-difluoro-3-hydroxypropoxy)pyridin-2-yl]ethyl}amino)-1,1-difluoro-2-oxoethyl]benzoate | 445.1 |
| 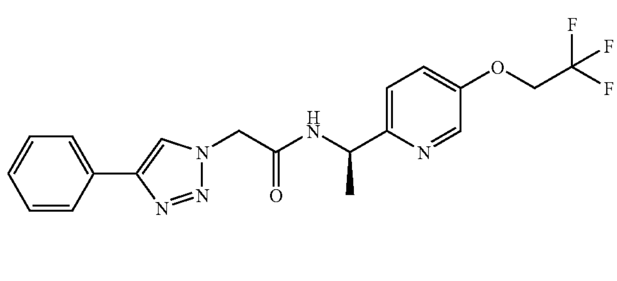 | 2-(4-phenyl-1H-1,2,3-triazol-1-yl)-N-{(1R)-1-[5-(2,2,2-trifluoroethoxy)pyridin-2-yl]ethyl}acetamide | 406.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 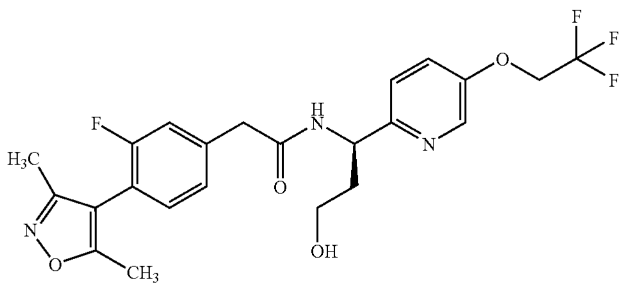 | 2-[4-(3,5-dimethylisoxazol-4-yl)-3-fluorophenyl]-N-{(1R)-3-hydroxy-1-[5-(2,2,2-trifluoroethoxy)pyridin-2-yl]propyl}acetamide | 481.9 |
| 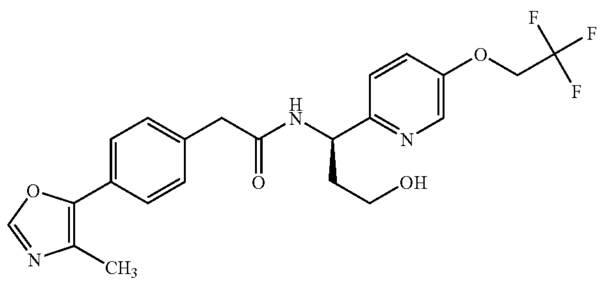 | N-{(1R)-3-hydroxy-1-[5-(2,2,2-trifluoroethoxy)pyridin-2-yl]propyl}-2-[4-(4-methyl-1,3-oxazol-5-yl)phenyl]acetamide | 449.9 |
| 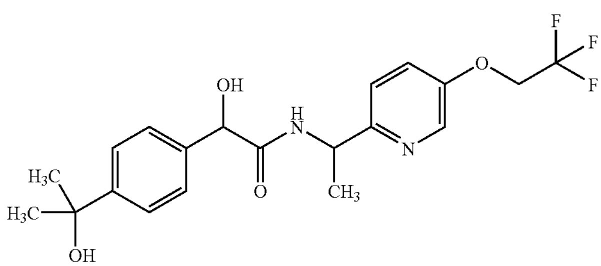 | 2-hydroxy-2-[4-(1-hydroxy-1-methylethyl)phenyl]-N-{1-{5-(2,2,2-trifluoroethoxy)pyridin-2-yl]ethyl}acetamide | 413.1 |
| 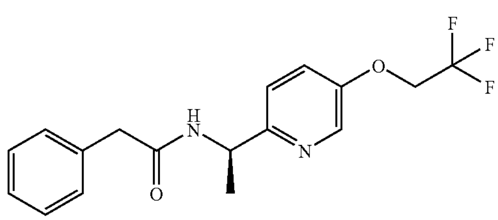 | 2-phenyl-N-{(1R)-1-[5-(2,2,2-trifluoroethoxy)pyridin-2-yl]ethyl}acetamide | 338.9 |
| 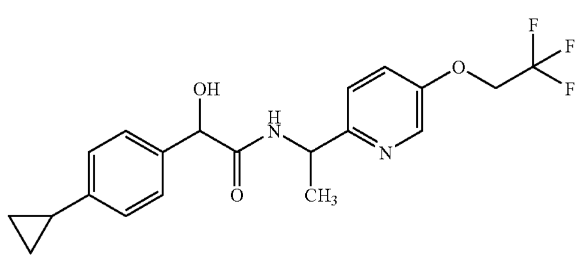 | 2-(4-cyclopropylphenyl)-2-hydroxy-N-{1-[5-(2,2,2-trifluoroethoxy)pyridin-2-yl]ethyl}acetamide | 395.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 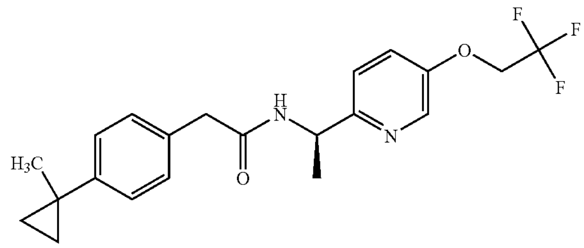 | 2-[4-(1-methylcyclopropyl)phenyl]-N-{(1R)-1-{5-(2,2,2-trifluoroethoxy)pyridin-2-yl]ethyl}acetamide | 392.8 |
| 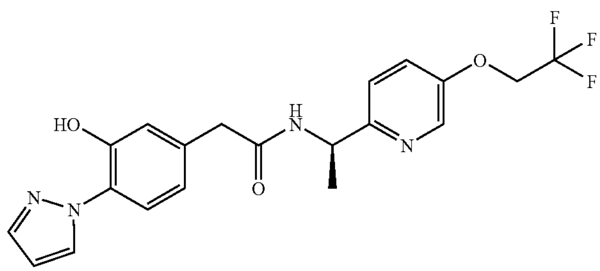 | 2-[3-hydroxy-4-(1H-pyrazol-1-yl)phenyl]-N-{(1R)-1-[5-(2,2,2-trifluoroethoxy)pyridin-2-yl]ethyl}acetamide | 421.1 |
| | 2-[3-methoxy-4-(1H-pyrazol-1-yl)phenyl]-N-{(1R)-1-[5-(2,2,2-trifluoroethoxy)pyridin-2-yl]ethyl}acetamide | 435.2 |
| 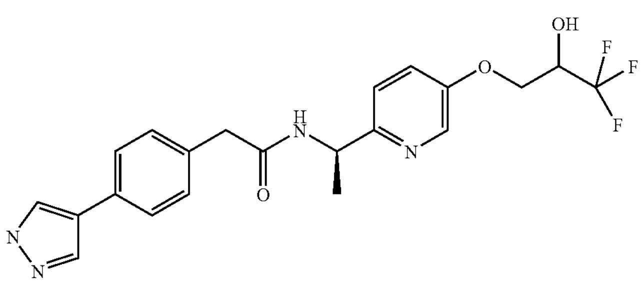 | 2-(4-(1H-pyrazol-4-yl)phenyl]-N-{(1R)-1-[5-(3,3,3-trifluoro-2-hydroxypropoxy)pyridin-2-yl]ethyl}acetamide | 435.1 |
| 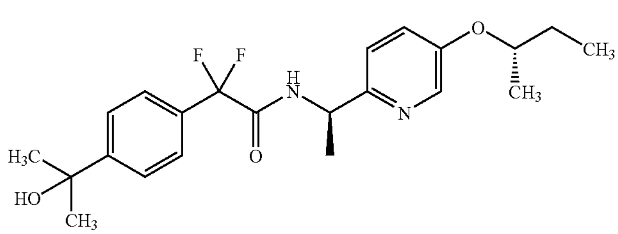 | 2,2-difluoro-2-[4-(1-hydroxy-1-methylethyl)phenyl]-N-[(1R)-1-(5-{[(1S)-1-methylpropyl]oxy}pyridin-2-yl)ethyl]acetamide | 407.3 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula:

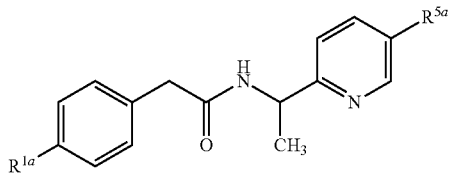

wherein:

$R^{1a}$ is selected from the group consisting of:
(1) halogen,
(2) phenyl, which is unsubstituted or substituted with halogen, hydroxyl, $C_{1-6}$alkyl, —O—$C_{1-6}$alkyl, $C_{3-6}$cycloalkyl, or —$NO_2$,
(3) —O-phenyl, which is unsubstituted or substituted with halogen, hydroxyl, $C_{1-6}$alkyl, —O—$C_{1-6}$alkyl,
(4) $C_{1-6}$alkyl, which is unsubstituted or substituted with halogen, hydroxyl or phenyl,
(5) $C_{3-6}$cycloalkyl, which is unsubstituted or substituted with halogen, hydroxyl or phenyl, and
(6) $C_{2-4}$alkenyl, which is unsubstituted or substituted with $C_{3-6}$cycloalkyl or phenyl;

$R^{5a}$ is independently selected from the group consisting of:
(1) hydrogen,
(2) fluoro,
(3) chloro,
(4) bromo,
(5) hydroxyl,
(6) —$CH_3$,
(7) —$CH_2OH$,
(8) —$CH_2CH_3$,
(9) —$CH=CH_2$,
(10) —$CH_2CH_2CH_3$,
(11) -cyclopropyl,
(12) —$OCH_3$,
(13) —$OCH_2F$,
(14) —$OCH_2$-cyclopropyl,
(15) —$OCH_2$-phenyl,
(16) —$OCH_2CH_3$,
(17) —$OCH_2CF_3$,
(18) —$OCH_2CH_2CH_3$,
(19) —$OCH_2(C=O)OCH_2CH_3$,
(20) —$OCH_2(C=O)NHCH_2CH_3$,
(21) —$OSO_2CH_3$, and
(22) —$O(C=O)OCH_3$;
or a pharmaceutically acceptable salt thereof.

2. The compound of claim 1 of the formula:

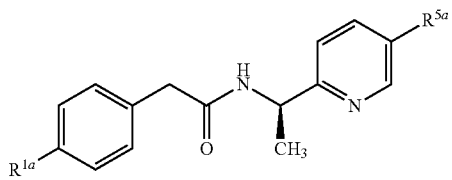

or a pharmaceutically acceptable salt thereof.

3. The compound of claim 1 wherein $R^{1a}$ is phenyl which is unsubstituted or substituted with one or more halogen.
4. The compound of claim 1 wherein $R^{1a}$ is $C_{1-6}$alkyl.
5. The compound of claim 1 wherein $R^{1a}$ is isopropyl or tert-butyl.
6. The compound of claim 1 wherein $R^{1a}$ is isopropyl.
7. The compound of claim 1 wherein $R^{1a}$ is cyclopropyl.
8. The compound of claim 1 wherein $R^{5a}$ is —$OCH_2CF_3$.
9. A compound which is selected from the group consisting of:

N-[(1R)-1-(5-bromopyridin-2-yl)ethyl]-2-(4-isopropylphenyl)acetamide;
2-(1,1'-biphenyl-4-yl)-N-[(1R)-1-(5-methoxypyridin-2-yl)ethyl]acetamide;
2-(1,1'-biphenyl-4-yl)-N-[(1R)-1-(5-hydroxypyridin-2-yl)ethyl]acetamide;
2-(1,1'-biphenyl-4-yl)-N-[(1R)-1-(5-propoxypyridin-2-yl)ethyl]acetamide;
2-(4-isopropylphenyl)-N-[(1R)-1-(5-methoxypyridin-2-yl)ethyl]acetamide;
N-[(1R)-1-(5-hydroxypyridine-2-yl)ethyl]-2-(4-isopropylphenyl)acetamide;
2-(4-isopropylphenyl)-N-[(1R)-1-(5-(2,2,2-trifluoroethoxy)pyridin-2-yl)ethyl]acetamide;
2-[4-(1-hydroxy-1-methylethyl)phenyl]-N-[(1R)-1-(5-(2,2,2-trifluoroethoxy)pyridin-2-yl)ethyl]acetamide;
2-(4-isopropenylphenyl)-N-[(1R)-1-(5-(2,2,2-trifluoroethoxy)pyridin-2-yl)ethyl]acetamide;
2-[4-(2-hydroxy-1-methylethyl)phenyl]-N-[(1R)-1-(5-(2,2,2-trifluoroethoxy)pyridin-2-yl)ethyl]acetamide;
2-(4-Cyclopropylphenyl)-N-((1R)-1-{5-[(2,2,2-trifluoroethyl)oxo]pyridin-2-yl}ethyl)acetamide;
2-(4-tert-butylphenyl)-N-[(1R)-1-(5-methoxypyridin-2-yl)ethyl]-acetamide;
2-(4-tert-butylphenyl)-N-[(1R)-1-(5-chloropyridin-2-yl)ethyl]acetamide;
2-(4-tert-butylphenyl)-N-[(1R)-1-(5-fluoropyridin-2-yl)ethyl]acetamide;
2-(4-vinylphenyl)-N-[(1R)-1-(5-methoxypyridin-2-yl)ethyl]acetamide;
2-(4-cyclopropylphenyl)-N-[(1R)-1-(5-methoxypyridin-2-yl)ethyl]acetamide;
2-(4-tert-butylphenyl)-N-{(1R)-1-[5-(fluoromethoxy)pyridin-2-yl]ethyl}acetamide;
2-biphenyl-4-yl-N-{(1R)-1-[5-(hydroxymethyl)pyridin-2-yl]ethyl}acetamide;
6-{(1R)-1-[(2-biphenyl-4-ylacetyl)amino]ethyl}pyridin-3-yl methanesulfonate;
6-{(1R)-1-[(biphenyl-4-ylacetyl)amino]ethyl}pyridin-3-yl methyl carbonate;
2-(4-isopropylphenyl)-N-[(1R)-1-(5-propoxypyridin-2-yl)ethyl]acetamide;
2-(4-isopropylphenyl)-N-[(1R)-1-(5-fluoromethoxypyridin-2-yl)ethyl]acetamide;

ethyl {[6-((1R)-1-{[(4-isopropylphenyl)acetyl]amino}ethyl)pyridin-3-yl]oxy}acetate N-{(1R)-1-[5-(benzyloxy)pyridin-2-yl]ethyl}-2-(4-bromophenyl)acetamide;

2-(4-isopropenylphenyl)-N-[(1R)-1-(5-methoxypyridin-2-yl)ethyl]acetamide;

N-{(1R)-1-[5-(2,2,2-trifluoroethoxy)pyridin-2-yl]ethyl}-2-[4-(trifluoromethyl)phenyl]acetamide;

2-[4-(1-hydroxycyclopropyl)phenyl]-N-{(1R)-1-[5-(2,2,2-trifluoroethoxy)pyridin-2-yl]ethyl}acetamide;

2-phenyl-N-{(1R)-1-[5-(2,2,2-trifluoroethoxy)pyridin-2-yl]ethyl}acetamide;

2-[4-(1-methylcyclopropyl)phenyl]-N-{(1R)-1-[5-(2,2,2-trifluoroethoxy)pyridin-2-yl]ethyl}acetamide;

2,2-difluoro-2-[4-(1-hydroxy-1-methylethyl)phenyl]-N-[(1R)-1-(5-{[(1S)-1-methylpropyl]oxy}pyridin-2-yl)ethyl]acetamide;

or a pharmaceutically acceptable salt thereof.

10. A compound which is selected from the group consisting of:

2-(4-isopropylphenyl)-N-[(1R)-1-(5-(2,2,2-trifluoroethoxy)pyridin-2-yl)ethyl]acetamide;

or a pharmaceutically acceptable salt thereof.

11. The compound of claim 10 which is 2-(4-isopropylphenyl)-N-[(1R)-1-(5-(2,2,2-trifluoroethoxy)pyridin-2-yl)ethyl]acetamide.

12. A pharmaceutical composition which comprises an inert carrier and a compound of claim 1 or a pharmaceutically acceptable salt thereof.

13. A pharmaceutical composition which comprises an inert carrier and a compound of claim 9 or a pharmaceutically acceptable salt thereof.

14. A pharmaceutical composition which comprises an inert carrier and a compound of claim 10 or a pharmaceutically acceptable salt thereof.

15. A pharmaceutical composition which comprises an inert carrier and a compound of claim 11 or a pharmaceutically acceptable salt thereof.

* * * * *